US007442378B2

(12) United States Patent
Browning et al.

(10) Patent No.: US 7,442,378 B2
(45) Date of Patent: Oct. 28, 2008

(54) ATTENUATED CIRCOVIRUS

(75) Inventors: Glenn Francis Browning, Melbourne (AU); Kelly Ann Tivendale, Melbourne (AU); Peter Christopher Scott, Melbourne (AU); Hayley Kay Brown, Boxhill North (AU); Brendan Scott Crabb, Melbourne (AU); Michelle Alma Peters, West Lafayette, IN (US)

(73) Assignee: The University of Melbourne, Parkville (AU)

( * ) Notice: Subject to any disclaimer, the term of this patent is extended or adjusted under 35 U.S.C. 154(b) by 316 days.

(21) Appl. No.: 10/480,565

(22) PCT Filed: Jun. 14, 2002

(86) PCT No.: PCT/AU02/00787

§ 371 (c)(1), (2), (4) Date: Aug. 13, 2004

(87) PCT Pub. No.: WO02/102999

PCT Pub. Date: Dec. 27, 2002

(65) Prior Publication Data

US 2006/0257424 A1 Nov. 16, 2006

(30) Foreign Application Priority Data

Jun. 14, 2001 (AU) .................................... PR 5674

(51) Int. Cl.

*A61K 39/38* (2006.01)
*A61K 39/12* (2006.01)
*A61K 39/175* (2006.01)

(52) U.S. Cl. ............... 424/204.1; 424/186.1; 424/184.1

(58) Field of Classification Search ....................... None
See application file for complete search history.

(56) References Cited

U.S. PATENT DOCUMENTS

| | | | | |
|---|---|---|---|---|
| 5,965,139 A * | 10/1999 | Schat et al. | .............. | 424/199.1 |
| 5,981,502 A | 11/1999 | Noteborn et al. | | |

FOREIGN PATENT DOCUMENTS

| | | |
|---|---|---|
| EP | 0483 911 A2 | 5/1992 |
| WO | WO 95/03414 | 2/1995 |
| WO | WO 96/01116 | 1/1996 |
| WO | WO 96/03507 | 2/1996 |
| WO | WO 96/40931 | 12/1996 |

OTHER PUBLICATIONS

The Journal of Veterinary Medical Science, vol. 58(7) Farkas et al., "Cloning and Sequencing of the Genome of Chicken Anaemia Virus (CAV) TK-5803 Strain and Comparison with Other CAV Strains", pp. 681-4. Abstract, line 6, (1996).

Archives of virology, vol. 146(4), 2001, Scott et al., "Characterization of a chicken anemia virus variant population that resists neutralisation with a group-specific monclonal anitbody" pp. 713-728. p. 717 and Table 5.

Australian Veterinary Journal, vol. 78, No. 9, 2000, Brown et al., "Full-length infections clone a pathogenic Australian isolate of chicken anaemia virus" pp. 637-640. Figure 1B and p. 639, 2nd column, line 1.

Claessens et al., "Molecular cloning and sequence analysis of the genome of chicken anaemia agent," *The Journal of General Virology*, 72: 2003-2006 (1991).

Search Report issued in corresponding EP application No. 02740122 (2005).

* cited by examiner

*Primary Examiner*—Bruce Campell
*Assistant Examiner*—Benjamin P Blumel
(74) *Attorney, Agent, or Firm*—Barnes & Thornburg LLP; Alice O. Martin

(57) ABSTRACT

An isolated attenuated circovirus having a mutation in viral nucleic acid encoding viral protein 2 (VP2). The attenuated circovirus is particularly suitable for use in conferring immunity in an animal, particularly birds.

37 Claims, 20 Drawing Sheets

Figure 2: Transfection of mut C 87 R into MSB1 cells.

Figure 3: Transfection of mut C 95 S into MSB1 cells.

Figure 4: Transfection of mut C 97 S into MSB1 cells.

Figure 5: Transfection of mut R 101 G into MSB1 cells.

Figure 6: Transfection of mut H103 Y into MSB1 cells.

Figure 7: Transfection of mut R129 G into MSB1 cells.

Figure 8: Transfection of mut N 131 P into MSB1 cells.

Figure 9: Transfection of mut R/K/K 150/151/152 G/A/A into MSB1 cells.

Figure 10: Transfection of mut D/E 161/162 G/G into MSB1 cells.

Figure 11: Transfection of mut L 163 P into MSB1 cells.

Figure 12: Transfection of mut D169 G into MSB1 cells.

Figure 15. Electrophoresis of glutathione-S-transferase (GST) fusion proteins on a 12.5% polyacrylamide gel and visualisation with Coomassie blue staining. Lane 1, Broad range molecular weight standards (Biorad); lane 2, 2.6 μg CAV VP2–GST fusion; lane 3, 3.0 μg GST.
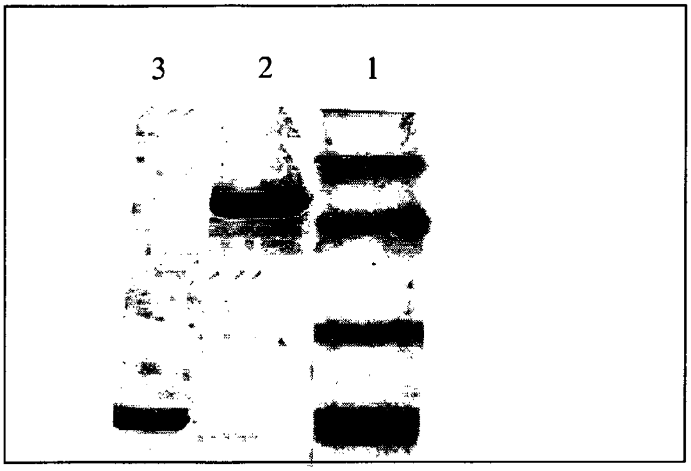

Figure 16. Western blot probed with a mouse polyclonal antiserum raised against the COOH-terminal region of VP2. Lane 1, Broad range molecular weight standards (Biorad) ; lane 2, 3.0 μg GST; lane 3, 2.6 μg CAV VP2–GST fusion.
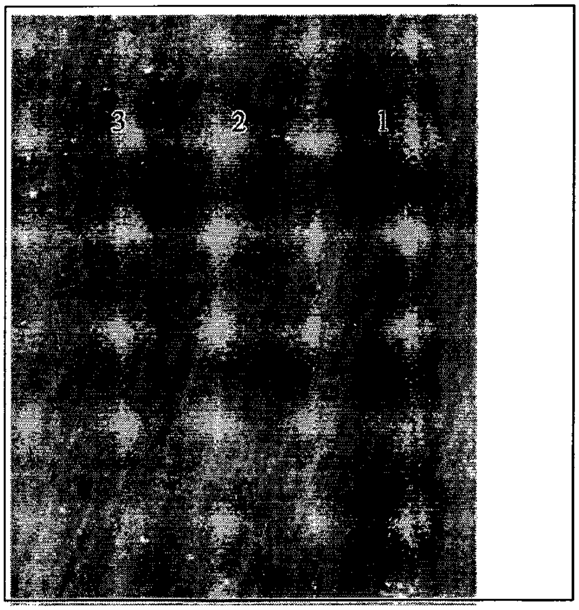

Figure 17. Western blot probed with a rabbit polyclonal antiserum raised against GST. Lane 1, molecular weight standards; lane 2, 3.0μg GST; lane 3, 2.6 μg chicken anaemia virus VP2–GST fusion.
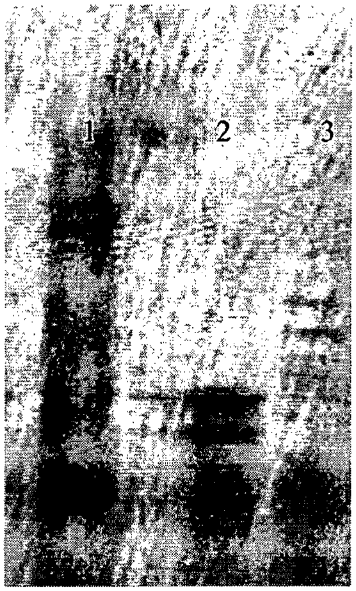

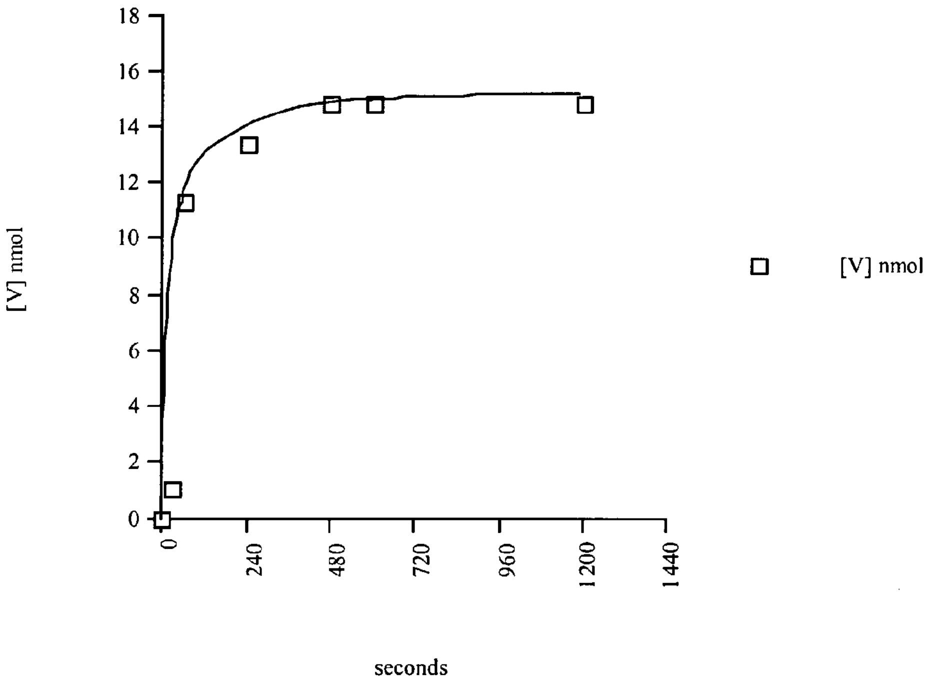
Figure 18. Time course study of phosphate release from ENDY(Pi)INASL as catalysed by VP2-GST or a GST control preparation. Reactions were carried out with 15 nmol substrate. Activity [V] was measured in nmol of phosphate released for each timepoint.

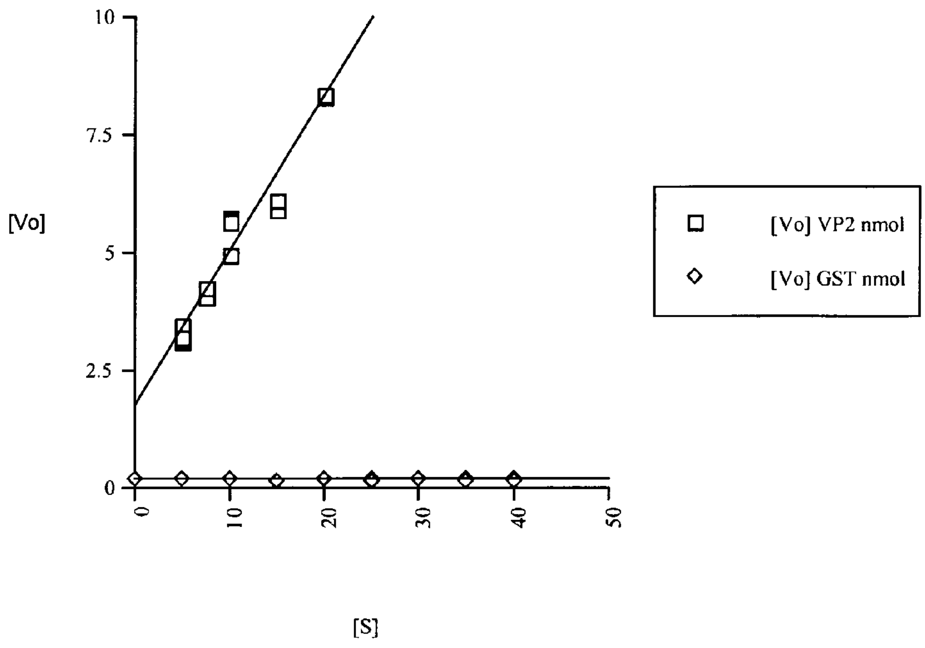
Figure 19. PTPase activity of VP2-GST and GST control proteins in the PTP assay. Reactions were carried out with 10 nmol substrate and for 1 min. Initial activity [Vo] was measured in nmol phosphate released for each substrate value. The standard error of the mean for each substrate value tested was less than 0.101.

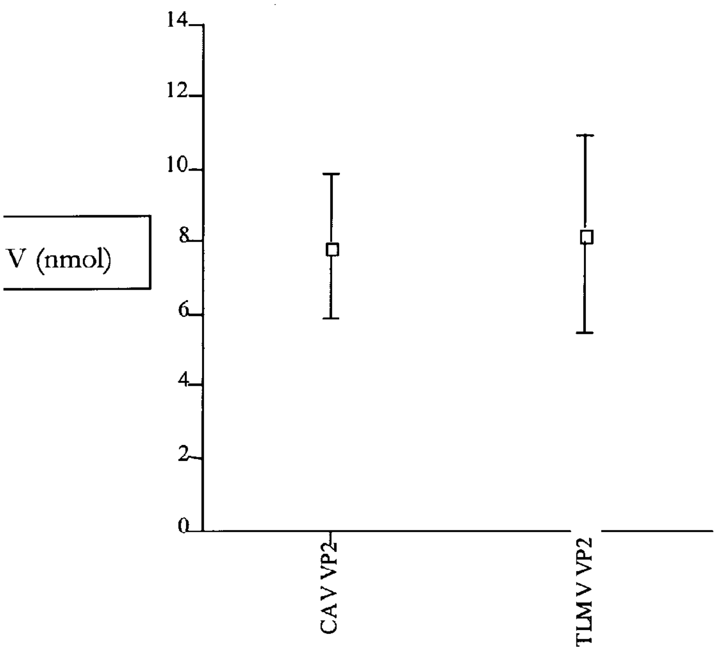
Figure 20. TLMV VP2 PTPase activity relative to CAV VP2 activity.

ATTENUATED CIRCOVIRUS

CROSS-REFERENCE TO RELATED APPLICATIONS

This application is a U.S. national stage of international patent application no. PCT/AU02/00787, filed Jun. 14, 2002, which claims priority to Australian patent application no. PR5674, filed Jun. 14, 2001.

TECHNICAL FIELD

The present invention relates to attenuated viruses, viral vaccine compositions, particularly attenuated circoviruses in the form of chicken anaemia virus.

BACKGROUND ART

Chicken anaemia virus (CAV) is a member of the Circoviridae family. The Circoviridae include a number of plant and animal viruses that are characterised by the possession of a single stranded, negative-sense, circular DNA genome. There is minimal similarity in the genomic sequence and organisation between CAV and the other characterised animal circoviruses: Psittacine Beak and Feather Disease Virus (PBFDV), Pigeon Circovirus and Porcine Circoviruses (PCV) 1 and 2. TT viruses (TTV) have recently been identified in human hosts and other species as a heterogeneous cluster of single stranded, negative-sense, circular DNA viruses. Sequence analysis of this group of viruses has demonstrated greatest overall homology to CAV and others have recently proposed the classification of the TTV, SANBAN, YONBAN, TLMV (TTV Like Mini Viruses) and CAV viruses as the Paracircoviridae, however, the phylogeny remains an area of active revision. The highest sequence homology to CAV is seen in the non-coding region and between open reading frame (ORF2) of TTV and VP2 of CAV. The high level of sequence conservation between CAV and TTV suggests VP2 may play a critical role in viral infection and pathogenesis.

CAV encodes only three proteins, with overlapping ORFs in three frames. ORF3 encodes the major 45-52 kDa capsid protein VP1, ORF2 encodes the 11-13 kDa VP3 that has demonstrated apoptotic activity in transformed cell lines, and ORF1 encodes a 28 kDa non-structural protein VP2 with unknown function. VP2 is expressed at barely detectable levels during infection, but has been shown to be essential for viral infection and replication in cells. The low level of expression of VP2 is consistent with a non-structural, regulatory protein involved in viral replication and infection.

CAV pathogenesis is characterised by immunosuppression and pancytopaenia arising from panmyelophthisis and thymocyte depletion. Immunosuppression results in increased rates of morbidity and mortality associated with coinfections and vaccination failure in CAV infected chicks. CAV infection is directly cytotoxic to two distinct T-cell populations of the thymus and spleen. Thymic infection involves immature lymphoblastic precursors, whereas splenic infection is of mature T-lymphocytes that are highly activated. There is a second indirect-component of immunosuppression found in uninfected immune effector cells. Reductions in macrophage and APC effector functions and B cell antigenic responses have been documented. Limited cytokine profiles from infected cells are suggestive of a basis for generalised indirect immunosuppression. There is a reduction in interleukin 2 (IL-2), interferon gamma (IFNγ), lymphocyte stimulation index, IL-1, T-cell growth factor activity and Fc receptor levels in lymphocytes of infected birds. The molecular basis for viral modulation of cytokine profiles and indirect immunosuppression is unknown.

Preliminary comparisons of the CAV VP2 sequence to sequences available in the Genbank database suggested similarity to a number of eukaryotic receptor PTPases (R-PTPase alpha). Database searches identified the human placental, rat, mouse and chicken R-PTPase alpha precursors as homologous to the CAV VP2 sequence. Reversible protein phosphorylation is universal in the regulation of cellular processes, including metabolism, gene regulation, cell cycle control, cytoskeletal organisation and cell adhesion. The PTPase family is highly diverse and includes the eukaryotic receptor-like transmembrane proteins and soluble cytosolic proteins, as well as bacterial PTPases, such as the YopH PTPase from pathogenic *Yersinia*, and a viral PTPase VH1 found in Vaccinia virus, a member of the Poxyiridae. During Vaccinia virus infection the VH1 protein blocks interferon γ signalling thereby evading the immune response to virus infection. The role of the VH1 PTPase in infection, although currently the only viral PTPase with a characterised in vivo function, does highlight the potential for virus encoded PTPases to be involved in mechanisms of immune evasion and virus persistence.

Commercial poultry producers require a chicken anaemia virus (CAV) vaccine that will reduce the economic losses incurred through both clinical and subclinical infections. The elimination of subclinical disease in adult birds associated with CAV infection requires overcoming immunosuppression due to infection. CAV infection is of greatest economic significance in broiler flocks. Both clinical and subclinical infections impact on commercial broiler performance and profitability. Whilst clinical infection produces a more marked reduction in performance parameters, subclinical infection is responsible for a greater degree of financial loss as it is of higher incidence. There is a strong need for a vaccine suitable for pullets, broilers and breeders. Such a vaccine may be administered to birds at the point of lay and therefore must be safe in the event of vertical transmission to embryos.

The development of a CAV vaccine has international applications. Chicken anaemia virus (CAV) has a worldwide distribution based on serological surveillance, and is endemic in both SPF and commercial chicken flocks, with the exception of Australian SPF flocks. Countries from which CAV isolates have been characterised and their complete genome sequences published include Germany, UK, USA, Japan, Australia, and the Netherlands. All isolates are classified within a single serotype based on cross reactivity in immunofluorescence and neutralisation tests utilising polyclonal antiserum. Genome sequence conservation is a key feature of all CAV isolates. All field isolates demonstrate equivalent pathogenicity in experimental infection and any variation in the morbidity and severity of disease with CAV exposure is attributed to a range of interacting, epidemiological factors. Viral dose is the key determinant of the severity of CAV induced disease in the field. It is expected that live attenuated vaccines developed from any one isolate will be protective in poultry flocks internationally.

An attenuated CAV strain should be infectious whilst having reduced pathogenicity. Clinical disease is best characterised in the literature in birds infected at 1 day old. Clinical disease in chicks infected at 1 day of age is characterised by weakness, depression, stunting and anaemia. By 7 days post infection, there is a transient but severe, peracute anaemia due to destruction of erythroblastoid cells and immunodeficiency due to depletion of cortical lymphocytes. Severe bone marrow hypoplasia, thymic and lymphoid atrophy and thrombocytopaenia are apparent at 14-21 days post infection. Petecchial and ecchymotic haemorrhages develop due to a primary coagulopathy. Immunosuppression is a significant feature of CAV induced disease and secondary infections are common. CAV affected birds have an increased incidence of malignant oedema, gangrenous dermatitis, colibacillosis and pulmonary aspergillosis. The recovery phase extends from 14-35 days post infection. Erythrocytopoiesis precedes granulocytopoiesis during recovery. At 16 days post infection there are a high proportion of circulating immature erythrocytes, thrombocytes and granulocytes, and the haematocrit is completely restored by 28 days post infection. The thymus is repopulated by the third wave of migrating lymphocytes at 21 days.

CAV affected birds develop a severe anaemia of myelophthisis. The haematocrit is less than 27%, and typically between 9-23% (normally in chicks 7-14 days of age it is 32-37.5%). Cyanosis is evident in the non-feathered integument and on mucosal membranes. There is a leukopaenia attributable to a heterocytopaenia and lymphopaenia. Prolonged clotting times are associated with petecchial and ecchymotic haemorrhages observed over the integument, skeletal muscle, mucosa of the proventriculus and rarely the pericardium.

The bone marrow appears yellow to white and watery in texture due to panmyelophthisis and compensatory adipocyte hyperplasia. This is most obvious in the proximal femoral medullary cavity.

The thymus undergoes severe atrophy. Affected thymuses have a quantifiable reduction in weight and a diameter of 2-4 mm. They appear red-brown instead of grey due to a reduction in parenchymal lymphocyte populations, hyperplasia of reticular cells and hyperaemia of the tissue.

There is a generalised depletion of lymphoid follicular components of all tissues. The bursa of Fabricius undergoes transient, moderate atrophy but is not swollen or oedematous. Bursal atrophy can be mild to unapparent in clinically affected chicks.

The liver, kidneys and spleen are diffusely discoloured and swollen at 14 days post infection.

Focal, dermal haemorrhagic lesions are most prominent on the wings, but also involve the head, rump, sides of thorax and abdomen, thighs, legs and feet. The lesions progress to large ulcers with a serosanguinous extravasation due to ischaemic necrosis of the overlying dermis. A purulent exudate develops in association with secondary infections. The lesions are prone to complicating abrasive and mutilation injury in the environment of the commercial broiler rearing unit.

An experimental model for CAV pathogenesis is required for the assessment of attenuation. Such a model does not need to represent the full spectrum of pathology observed in field infection but must demonstrate attenuation under conditions that produce most severe pathology. Yolk sac inoculation of 7 day embryos with high doses of virus is the most stringent model available. This model best approximates the field situation in which naïve breeder birds at the point of lay are exposed to CAV and transmit virus transovarially. Chicks infected by vertical transmission have the highest rates of morbidity (100%) and mortality (10-70%) and the pathology is of greatest severity. Extensive studies of the pathology of embryos experimentally infected at 7 days by yolk sac inoculation have not been reported in the literature.

Chickens of all ages are susceptible to CAV infection, however there is an age-specific resistance to the development of disease in chickens older than 14 days. Embryos and 1 day old chicks have the highest disease susceptibility. Age resistance may relate to the developing capacity of the bird to produce a serum neutralising humoral response. Co-infection with synergistic avian pathogens such as IBDV will eliminate age-related resistance and will result in outbreaks of acute severe disease in older birds.

The majority of commercial breeder flocks have been exposed to CAV and have long lasting neutralising humoral immunity. Antibody persists for at least 20 weeks after seroconversion. Serological surveys of breeder flocks typically demonstrate 97.5-100% of birds remain seropositive over an extended period post infection. Maternal antibody is important in protection against clinical disease in chickens up to 2 weeks of age, and persists until 3 weeks of age. The decay of maternal antibody follows a linear relationship and has a half life of approximately 1 week. Low levels of maternal antibody are effective in preventing clinical disease with infection. The majority of hatchlings derived from immune breeder flocks are infected horizontally following the waning of maternal antibody, develop subclinical disease and seroconvert between 8-12 weeks post infection. In an exposed flock, approximately 10% of breeders will be seronegative at any point post exposure. A minor proportion of chickens are infected vertically and excrete high titres of virus acting as the source of horizontal infection for other hatchlings. There may be between 16 and 25% birds sub-clinically affected in the progeny of immune breeder flocks. Vaccination will therefore improve performance even in flocks with endemic CAV and persistent neutralising humoral immunity.

The present inventors have developed live attenuated CAV and CAV DNA capable for use in vaccines suitable for the inoculation of pullets, broiler and breeder flocks, based on the identification of the function of the VP2 as a novel protein tyrosine phosphatase and the identification of regions of its sequence required for full function.

DISCLOSURE OF INVENTION

In a first aspect, the present invention provides an isolated attenuated circovirus having a mutation in viral nucleic acid encoding viral protein 2 (VP2).

Preferably, the circovirus is Chicken anaemia virus (CAV), a TT virus (TTV) or other similar virus. More preferably, the circovirus is Chicken anaemia virus (CAV). The definition of circovirus is intended to include CAV and any other virus having a single stranded, negative-sense, circular DNA genome and expressing a protein having the functionally equivalent activity as CAV VP2 protein.

The selection of sites for mutation is best based on concurrent investigations of viral function. The present inventors have found that CAV VP2 is a good target for attenuation through mutagenesis as the possibility exists to alter virulence whilst retaining infectivity and immunogenicity. The establishment of a precise biochemical function for CAV VP2 as a PTPase, as part of the current invention, greatly facilitates the process of rational attenuation and provides a focal point for the mutagenesis strategy. Mutations can be designed to modify the role of the PTPase in infection based on the understanding of their effect on PTPase catalysis in vitro. It is predicted that CAV VP2 is a multifunctional protein with an essential non-structural role in virus infection and replication. As the protein is non-structural, it is improbable that mutations will alter epitopes essential to immunogenicity. As the lymphocyte is the target cell of CAV infection, it is probable that virulence is inversely correlated with immunogenicity, provided adequate virus replication is achieved for antigenic stimulation. Mutations which reduce virulence and the immunosuppressive influence of virus infection may therefore enhance the immunogenic properties of the virus relative to wild type virus.

In one preferred form, a mutation is present in the region of nucleic acid encoding the key residues in the signature motif of VP2. Such mutations should modify the role of the PTPase during viral infection. More preferably, sites targeted for mutagenesis within CAV VP2 are 86, 95, 97, 101, 103, and 169. Residue 86 is normally C and was mutated to S (mut C 86 S), and the other demonstrative mutations were mut C 95 S, mut C 97 S, mut R 101 G and mut H 103 Y. The mutations mut C 95 S and mut C 97 S remove the cysteine residues predicted to be essential to PTPase activity and to be the catalytic cysteines involved in the formation of the cysteinyl-phosphate intermediate formed during catalysis. The mutation mut R 101 G removes the basic, charged residues predicted to be essential to PTPase activity and to be involved in the coordination of the phosphotyrosine substrate to the catalytic cysteine residues. Residues 103 and 86 flank the predicted signature motif and are highly conserved across TT and CAV viruses.

In another preferred from, a mutation is present in the region of nucleic acid encoding two predicted regions of amphipathic α-helix from residues 128 to 143 and amphipathic β-sheet from residues 151 to 158 in CAV VP2. Other regions suitable include nucleic residues 80 to 110, 128 to 143, 151 to 158 and 160 to 170 in CAV VP2.

Preferably, CAV constructs are selected from mut C87R, mut C 95 S, mut C 97 S, mut R 101 G, mut H 103 Y, mut R 129 G, mut Q 131 P, mut R/K/K 150/151/152 G/A/A, mut D/E 161/162 G/G, mut L 163 P, mut D 169 G, mut K 102 E, mut E 186 G and combinations thereof.

The CAV found to be particularly suitable candidates for a vaccine include mut C87R, mut R 101 G, mut K 102 D, mut H 103 Y, mut R 129 G, mut N 131 P, mut R/K/K 150/151/152 G/A/A, mut D/E 161/162 G/G, mut L 163 P, mut D 169 G, mut K 102 E and mut E 186 G.

Preferably, CAV constructs are selected from sequence no's 1, 3, 5, 7, 9, 11, 13, 15, 17, 19, 21, 23, 25, or 27.

As the genome structure of TTV is similar to CAV, the attenuation information obtained by the present inventors on CAV would be applicable to TTV. This has been further supported by the demonstration by the present inventors that the ORF2 of TLMV has protein tyrosine phosphatase activity. Thus, from the extensive information obtained by the present inventors on CAV, it would be expected that attenuated TTV (or other similar circoviruses) could be formed by introducing mutations at the corresponding or similar ORF2 coding regions of TTV or other ciroviruses.

In a second aspect, the present invention provides a circovirus vaccine composition comprising an attenuated circovirus according to the first aspect of the present invention together with an acceptable carrier or diluent.

In one preferred form, the virus is CAV and the animal is a bird, preferably a chicken.

In another preferred form, the virus is TTV and the animal is a mammal, preferably a human.

The vaccine composition may be formulated to contain a carrier or diluent and one or more of the attenuated viruses of the invention. Suitable pharmaceutically acceptable carriers facilitate administration of the viruses but are physiologically inert and/or non-harmful to the recipient. Carriers may be selected by one of skill in the art. Suitable carriers include sterile saline, lactose; sucrose, calcium phosphate, gelatin, dextrin, agar, pectin, peanut oil, olive oil, sesame oil, and water. Additionally, the carrier or diluent may include a material which delays release of the virus, such as glycerol monostearate or glycerol distearate alone or with a wax. In addition, slow release polymer formulations can be used.

Optionally, the vaccine composition may further contain preservatives, chemical stabilizers, other antigenic proteins, and conventional pharmaceutical ingredients. Suitable ingredients which may be used in a vaccine composition in conjunction with the viruses include, for example, casamino acids, sucrose, gelatin, phenol red, N-Z amine, monopotassium diphosphate, lactose, lactalbumin hydrolysate, and dried milk. Typically, stabilizers, adjuvants, and preservatives are optimized to determine the best formulation for efficacy in the target animal or human. Suitable preservatives include chlorobutanol, potassium sorbate, sorbic acid, sulfur dioxide, propyl gallate, the parabens, ethyl vanillin, glycerin, phenol, and parachlorophenol.

A vaccine composition of this invention is most preferably produced without an adjuvant. Where necessary, one or more of the above described vaccine components may be admixed or adsorbed with a conventional adjuvant. The adjuvant is used as a non-specific irritant to attract leukocytes or enhance an immune response. Such adjuvants include, among others, mineral oil and water, aluminum hydroxide, Amphigen, Avridine, L121/squalene, D-lactide-polylactide/glycoside, pluronic plyois, muramyl dipeptide, killed *Bordetella*, saponins, and Quil A.

Alternatively, or in addition to the virus of the invention, other agents useful in treating viral infection, such as immunostimulatory agents, are expected to be useful in reducing and eliminating disease symptoms, particularly in humans. The development of vaccine or therapeutic compositions containing these agents is within the skill of one of skilled in the art in view of the teaching of this invention.

According to the method according to the second aspect of the invention, an animal or human may be vaccinated against circovirus infection by administering an effective amount of a vaccine composition described above. An effective amount is defined as that amount of circovirus vaccine capable of inducing protection in the recipient against circovirus infection. The vaccine may be administered by any suitable route. Such a composition may be administered parenterally, preferably intramuscularly or subcutaneously. However, it may also be formulated to be administered by any other suitable route, including intranasal, oral, intravaginal, subcutaneous or intradermal, or in ovo route.

Suitable effective amounts of the circovirus of this invention can be determined by one of skill in the art based upon the level of immune response desired. Such a composition may be administered once, and/or a booster may also be administered. However, suitable dosage adjustments may be made by the attending veterinarian or physician depending upon the age, sex, weight and general health of the animal or human subject. Typically, dosage range for the vaccine is in the order of 1-100 million $TCID_{50}$. Preferably, the dosage is around 1000 $TCID_{50}$.

Similarly, suitable doses of the vaccine composition of the invention can be readily determined by one of skill in the art. The dosage can be adjusted depending upon the animal species being treated, i.e. its weight, age, and general health.

In a third aspect, the present invention provides a method of conferring immunity in an animal against a circovirus infection, the method comprising administration to the animal of a vaccine composition according to the second aspect of the present invention.

In one preferred form, the virus is CAV and the animal is a bird, preferably a chicken.

In another preferred form, the virus is TTV and the animal is a mammal, preferably a human.

The vaccine may be administered by any suitable route including via an intranasal, oral, intravaginal, subcutaneous or intradermal, or in ovo route.

For bird such as chickens, the preferred route of administration is by mucosal administration, aerosol administration or via drinking water.

The administered vaccine composition may also be used to prevent clinical signs of circovirus infection.

The administered vaccine composition may also be used to induce an immunological response in the animal against a circovirus.

In a fourth aspect, the present invention provides an isolated nucleic acid molecule derived or obtained from a circovirus genome, the nucleic acid molecule including at least a portion of a coding region for viral protein 2 (VP2) having a mutation therein.

Preferably, the circovirus is Chicken anaemia virus (CAV), a TT virus (TTV) or other similar virus. More preferably, the circovirus is Chicken anaemia virus (CAV). The definition of circovirus is intended to include CAV and any other virus having a single stranded, negative-sense, circular DNA genome and expressing a protein having the functionally equivalent activity as CAV VP2 protein.

Preferably, the isolated nucleic acid molecule includes the complete circovirus genome incorporating mutations in either the VP2 translational initiation regions, the PTPase motifs or the acidic alpha helical regions or the basic beta sheet regions.

Preferably, the isolated nucleic acid molecule is selected from sequence no's 1, 3, 5, 7, 9, 11, 13, 15, 17, 19, 21, 23, 25, or 27.

In a fifth aspect, the present invention provides a circovirus vaccine composition comprising an isolated nucleic acid molecule according to the fourth aspect of the present invention together with an acceptable carrier or diluent.

In one preferred form, the virus is CAV and the animal is a bird, preferably a chicken.

In another preferred form, the virus is TTV and the animal is a mammal, preferably a human.

In a sixth aspect, the present invention provides a method of conferring immunity in an animal against a circovirus infection, the method comprising administering to the animal a vaccine composition according to the fifth aspect of the present invention.

In a seventh aspect, the present invention provides an isolated viral protein 2 (VP2) having PTPase activity obtained from a circovirus.

Preferably, the circovirus is Chicken anaemia virus (CAV), a TT virus (TTV) or other similar virus. More preferably, the circovirus is Chicken anaemia virus (CAV). The definition of circovirus is intended to include CAV and any other virus having a single stranded, negative-sense, circular DNA genome and expressing a protein having the functionally equivalent activity as CAV VP2 protein.

Preferably, the isolated VP2 is modified to have altered PTPase activity.

Preferably, the isolated VP2 molecule includes the amino acid sequences selected from sequence no's 2, 4, 6, 8, 10, 12, 14, 16, 18, 20, 22, 24, 26, or 28.

In an eighth aspect, the present invention provides use of an attenuated circovirus according to the first aspect of the present invention in the manufacture of a vaccine for conferring immunity in an animal against a circovirus infection.

In a ninth aspect, the present invention provides use of an isolated nucleic acid molecule according to the fourth aspect of the present invention in the manufacture of a vaccine for conferring immunity in an animal against a circovirus infection.

In a tenth aspect, the present invention provides a method for producing a circovirus vaccine according to the second apsect of the invention comprising:

(a) inoculating an isolated nucleic acid molecule derived or obtained from a circovirus genome into the yolk sac of an ambryonated egg, wherein the nucleic acid molecule includes at least a portion of a coding region for viral protein 2 (VP2) having a mutation therein;

(b) allowing circovirus to replicate from the isolated nucleic acid; and (c) harvesting the circovirus from the egg.

Preferably, the circovirus is Chicken anaemia virus (CAV), a TT virus (TTV) or other similar virus. More preferably, the circovirus is Chicken anaemia virus (CAV). The definition of circovirus is indended to include CAV and any other virus having a single stranded, negative-sense, circular DNA genome and expresssing a protein having a functionally equivalent activity as CAV VP2 protein.

Preferably, the isolated nucleic acid molecule includes the complete circovirus genome incorporating mutations in either the VP2 translation initiation regions, the PTPase motifs or the acidic alpha helical regions or the basic beta sheet regions.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

BRIEF DESCRIPTION OF THE DRAWINGS

FIG. 15 shows an electrophoresis separation of glutathione-S-transferase (GST) fusion proteins on a 12.5% polyacrylamide gel and visualisation with Coomassie blue staining. Lane 1, Broad range molecular weight standards (Biorad); lane 2, 2.6 μg CAV VP2-GST fusion; lane 3, 3.0 μg GST.

FIG. 16 shows a western blot probed with a mouse polyclonal antiserum raised against the COOH-terminal region of VP2. Lane 1, Broad range molecular weight standards (Biorad); lane 2, 3.0 μg GST; lane 3, 2.6 μg CAV VP2-GST fusion.

FIG. 17 shows a western blot probed with a rabbit polyclonal antiserum raised against GST. Lane 1, molecular weight standards; lane 2, 3.0 μg GST; lane 3, 2.6 μg chicken anaemia virus VP2-GST fusion.

FIG. 18 shows a time course study of phosphate release from ENDY(Pi)INASL (SEQ ID NO: 71) as catalysed by VP2-GST or a GST control preparation. Reactions were carried out with 15 nmol substrate. Activity [V] was measured in nmol of phosphate released for each timepoint.

FIG. 19 shows PTPase activity of VP2-GST and GST control proteins in the PTPase assay. Reactions were carried out with 10 nmol substrate and for 1 min. Initial activity [$V_o$] was measured in nmol phosphate released for each substrate concentration. The standard error of the mean for each substrate concentration tested was less than 0.101.

FIG. 20 shows TLMV VP2 PTPase activity relative to CAV VP2 activity.

MODE(S) FOR CARRYING OUT THE INVENTION

Experimental Procedures

I. CAV Vaccine

Analysis of CAV Genome and Design of Sites for Mutagenesis

Studies described later (EXPERIMENTAL PROCEDURES—VP2) have established PTPase activity and predicted key residues in the signature motif have been identified by comparison to known PTPase signature motifs. These residues have formed the basis for the design of a mutagenesis strategy in an infectious full genome clone of CAV. Mutations can be designed to modify the role of the PTPase during infection based on an understanding of their effect on PTPase catalysis in vitro. Sites targeted for mutagenesis within CAV VP2 to demonstrate the applicability of this strategy were 86, 95, 97, 101, and 103. Residue 86 is normally C and was mutated to S (mut C 86 S), and the other demonstrative mutations were mut C 95 S, mut C 97 S, mut R 101 G, and mut H 103 Y. The mutations mut C 95 S and mut C 97 S remove the cysteine residues predicted to be essential to PTPase activity and to be the catalytic cysteines involved in the formation of the cysteinyl-phosphate intermediate formed during catalysis. The mutations mut R 101 G removes the basic, charged residues predicted to be essential to PTPase activity and to be involved in the coordination of the phosphotyrosine substrate to the catalytic cysteine residues. Residues 103 and 86 flank the predicted signature motif and are highly conserved across TT and CAV viruses.

Figure 1:
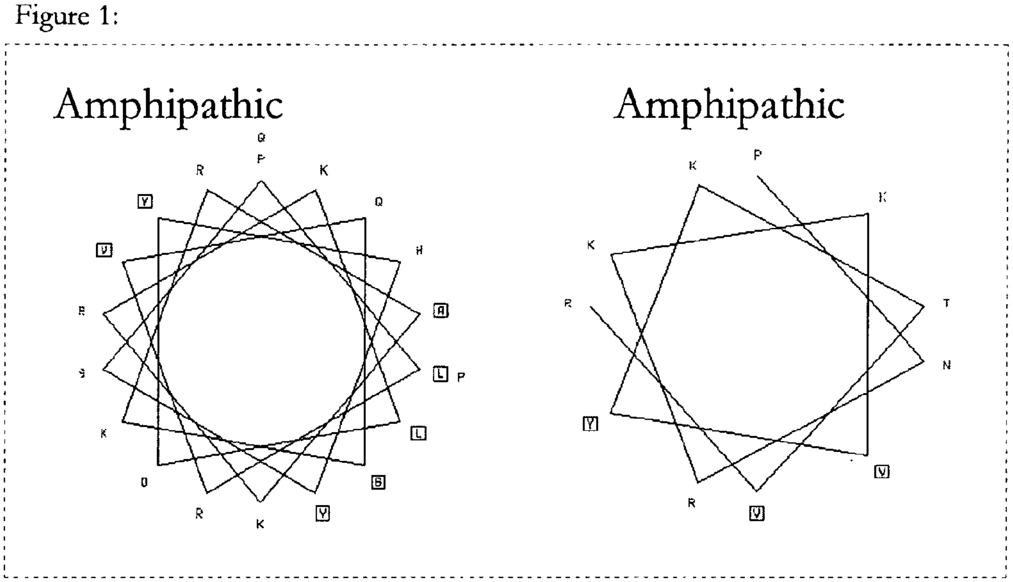
FIG. 1 shows Chou-Fasman plots of two predicted regions of amphipathic α-helix from residues 128 to 143 and amphipathic β-sheet from residues 151 to 158 of VP2.

VP2 protein structural predictions were made using software available through the ANGIS interface (WebANGIS, Australian National Genomic Information Service). A region of high degree secondary structure was identified towards the carboxyl-terminal end of VP2. Chou-Fasman plots of the region predict an acidic region consisting of α-helix, followed by a basic region consisting of α-helix and β-sheet, then a second acidic region of α-helix. The secondary structure is further subdivided by a series of proline residues. There are two predicted regions of amphipathic α-helix from residues 128 to 143 and amphipathic β-sheet from residues 151 to 158 (FIG. 1). It is predicted that the high degree of secondary structure correlates to a functional protein domain. The predictions for secondary structure allow the introduction of mutations designed to disrupt the structural organisation of the region thereby modifying the function of this region. To demonstrate the effect of mutation within the region of predicted basic amphipathic alpha-helix mut R 129 G and mut R/K/K 150/151/152 G/A/A have been constructed to neutralise the polar basic charge distribution in the secondary structure. The mut Q 131 P has also been introduced into the alpha helix in this region to break the helix. An identical approach was employed to disrupt the region of acidic alpha helix with the introduction of mut L 163 P. In the region of acidic alpha helix mut D/E 161/162 G/G and mut D 169 G constructs were made with the objective of neutralising the acidic charge distribution. The mutated nucleic sequences of the CAV genome and VP2 amino acid sequences are listed in sequences no's 1 to 28.

Primer Design

The CAU269/7 Australian isolate of CAV was used in all experiments. For each introduced mutation, paired, overlapping oligonucleotides were synthesised complementary to both strands of the CAV VP2 sequence. The oligonucleotide pairs were designed to incorporate nucleotide substitutions encoding the amino acid alterations. The CAV genome encodes 3 genes in 3 different overlapping open reading frames. The regions of CAV VP2 targeted for mutagenesis overlap ORF2 and ORF3, which are frameshifted relative to VP2 by one and two base pairs respectively. None of the introduced mutations change the amino acid sequences encoded by ORF2 and ORF3. Table 1 outlines primers used in the introduction of mutations to CAV VP2.

TABLE 1

Primers (SEQ ID NOS 29-54, left to right, in order of appearance) incorporating base changes encoding directed mutations within CAV VP2 sequence. The numbering of mutations is based on VP2 amino acid sequence. Mutated residues are indicated.

| mutation introduced into CAV VP2 | + sense oligonucleotide | - sense oligonucleotide |
|---|---|---|
| mut C 86 R | ctgcgcgaaCgctcgcg ttcccacgctaag | aacgcgagcGttcgcg cagccacacagcga |
| mut C 95 S | cgctaagatcAgcaact gcg | cgcagttgcTgatctta gcgtg |

TABLE 1-continued

Primers (SEQ ID NOS 29-54, left to right, in order of appearance) incorporating base changes encoding directed mutations within CAV VP2 sequence. The numbering of mutations is based on VP2 amino acid sequence. Mutated residues are indicated.

| mutation introduced into CAV VP2 | + sense oligonucleotide | - sense oligonucleotide |
|---|---|---|
| mut C 97 S | atctgcaacAgcggac aattc | attgtccgcTgttgcag atcttag |
| mut R 101 G | ctgcggacaattcGga aaacactgg | cagtgttttcCgaatt gtccgcag |
| mut H 103 Y | cagaaaaTactggtttc aagaatgtgccggac | gaaaccagtAttttct gaattgtccgcag |
| mut R 129 G | ctgcgacccctcGgag tacaggg | ccctgtactcCgaggg gtcgcaggatcgc |
| mut Q131 P | cgagtacCgggtaagc gagctaaaag | cgcttacccGgtactc ggagg |
| mut R/K/K 150/151/152 G/A/A | ccgaacGgcGCgGCg gtgtataag | atacaccGCcGCgcCg ttcggggtc |
| mut D/E 161/162 G/G | taagatggcaagGcg Ggctcgcagacc | tgcgagcCcgCcttgc catc |
| mut L 163 P | gacgagcCcgcagacc gagag | ggcctctcggtctgcg Ggctcgtc |
| mut D 169 G | gagaggccgGttttac gccttcag | gcgtaaaaCcggcctc tcggtc |
| mut K 102 E | ctgcggacaattcaga Gaacactggtttc | gaaaccagtgttCtct gaattgtccgcag |
| mut E 186 G | gcgacttcgacgGaga tataaatttc | tttatatctCcgtcgaag tcgc |

Overlap Extension PCR Mutagenesis

Mutations were introduced into CAV VP2 sequence by overlap extension PCR. The following method applies to the mutagenesis of all mutant constructs unless otherwise stated. The PCR template was a full genome clone of CAV (pCAU269/7) in the plasmid vector pGEX-4Z (Promega). Template DNA was prepared from *E. coli* DH5 α possessing the pCAU269/7 clone cultured at 37° C. on Luria-Bertani agar (LA) with 50 μg/mL ampicillin selection. A plasmid preparation was made using a Qiagen kit according to the manufacturer's instructions (Qiagen). The mutagenesis PCR was carried out in two stages. The first stage consisted of a set of 2 PCR reactions: one from an upstream flanking primer to the −sense mutagenesis primer, and one from a downstream flanking primer to the +sense mutagenesis primer. In the second stage of mutagenesis PCR products from the first pair of reactions acted as template in an oversew PCR reaction utilising the flanking primers. The PCR product generated is bounded by the flanking sequences and incorporates in both strands the mutations introduced into the template in the first stage of PCR.

The upstream flanking primer CAV.1 - 5' CTATCGAATTCCGAGTGGACTAT 3' (SEO ID NO: 55) and downstream flanking primer CAV.10 - 5' TGCTCACGTATGTCAGGTTC 3' (SEO ID NO: 56) were used in the oversew PCR for the construction of mut C 95 S and mut C 97 S. In the first stage, a 100 μL reaction mixture was prepared containing 300 μM each of dATP, dCTP, dGTP and dTTP, 2 mM $MgSO_4$, 200 μM of each primer, 10 μL of 10×Platinum Pfu Taq DNA polymerase buffer, 2 U of Platinum Pfu Taq DNA polymerase (Promega), and 1 μL of template DNA. The PCR reaction was incubated at 95° C. for 2 mm, followed by 30 cycles at 95° C. for 40 s, 60° C. for 60 s then 68° C. for 40 s, and a final incubation at 68° C. for 5 mm. First stage template was removed by digestion with DpnI restriction endonuclease (Life Technologies). The PCR products were analysed by agarose (1%) gel electrophoresis and the bands corresponding to the stage one products were excised and purified by Qiaex II (Qiagen) gel extraction according to the manufacturer's instructions. For the oversew PCR, a 100 μL reaction mixture was prepared containing 300 μM each of dATP, dCTP, dGTP and dTTP, 2 mM $MgSO_4$, 200 μM of each primer, 10 μL of 10×Hifidelity Taq DNA polymerase buffer, 2 U of Hifidelity Taq DNA polymerase (Promega), and 1 μL of template DNA. The PCR reaction was incubated at 95° C. for 2 mm, followed by 1 cycle at 95° C. for 40 s, 57° C. for 90 s then 68° C. for 40 s, then 15 cycles at 95° C. for 40 s, 57° C. for 60 s then 68° C. for 40 s, and a final incubation at 68° C. for 5 mm.

Methods for mutagenesis of all other mutants except for mut C 86 R and mut H 103 Y were as described for mut C 95 S and mut C 97 5, except the upstream flanking primer was primer CAV.2-5' GCGGAGCCGCGCAGGGGCAA 3' (SEO ID NO: 57) and the downstream flanking primer was CAV. 10. In the second stage oversew PCR the reactions were incubated at 96° C. for 2 mm, followed by 15 cycles at 96° C. for 40 s, 58° C. for 60 s then 72° C. for 60 s, and a final incubation at 72° C. for 5 min.

A range of PCR conditions were tried unsuccessfully in an attempt to PCR oversew the mutagenesis products for mut C87R and mut H 103 Y. Mut C87R and mut H 103 Y were therefore generated by full-circle, overlap extension mutagenesis in a single PCR reaction. A 100 μL reaction mixture was set up as described previously, however using the relevant mutagenesis primers only. The PCR reaction was incubated at 96° C. for 2 min, followed by 1 cycle at 96° C. for 40 s, 55° C. for 60 s then 68° C. for 5 min, then 40 cycles at 96° C. for 40 s, 60° C. for 60 s then 68° C. for 5 min, and a final incubation at 68° C. for 5 min. Template DNA was removed by digestion with DpnI restriction endonuclease and the PCR product was purified by standard phenol, phenol-chloroform and phenol-chloroform-isoamyl extraction and ethanol precipitation.

Cloning of Mutant Constructs

The following method applied to the cloning of all mutant constructs unless otherwise stated. The PCR products containing the mutant sequences were subcloned into the CAV infectious clone in the plasmid vector pGEX-4Z, pCAU269/7. The PCR products were digested with StuI and BsmI restriction endonuclease and analysed by agarose (1%) gel electrophoresis. A band of 357 bp was excised and purified by Qiaex II (Qiagen) gel extraction according to the manufacturer's instructions. pCAU269/7 was similarly digested with StuI and BsmI restriction endonucleases to remove the region of 357 bp to be replaced with the mutant sequence and the band of 4687 bp was purified from a 1% agarose gel. The PCR product was then ligated into the digested CAV-pGEX-4T-2 (Promega) backbone following standard protocols. *E. coli* DH5α was transformed by electroporation with the ligated plasmid and cultured at 37° C. on Luria-Bertani agar (LA) containing ampicillin at 50 μg/mL. Plasmid was purified from selected clones using a Qiagen kit according to the manufacturer's instructions (Qiagen). Clones were screened for the presence of insert by PCR using the forward primer CAV.2 and reverse primer CAV.10. The cloned DNA was sequenced using a Taq Dye Deoxy Terminator Cycle Sequencing kit (Perkin Elmer), using primers CAV.2 and CAV.10.

Methods for the construction of mut C87R and mut H 103 Y proceeded as described, except for the following variations. The purified stage 2 PCR product was cloned initially into the pGEM-4T-2 vector (Promega) according to the manufacturer's instructions, and then digested with StuI and BsmI restriction endonucleases and subcloned into pCAU269/7 as described previously. The mut C87R and mut H 103 Y PCR products, following digestion with DpnI restriction endonuclease, were ligated following standard protocols, and transformed by electroporation into *E. coli* DH5 α and cultured at 37° C. on Luria-Bertani agar (LA) containing ampicillin at 50 μg/mL. Clones containing the mutant sequence were then screened and selected as described above.

Transfection of Mutated Viral Genomes Into MSB1 Cells

The clone control pCAU269/7, control pEGFP-C2 and constructs mut C87R, mut C 95 S, mut C 97 S, mut R 101 G, mut H 103 Y, mut R 129 G, mut N 131 P, mut R/K/K 150/151/152 G/A/A, mut D/E 161/162 G/G, mut L 163 P, mut D 169 G and mut E 186 G were transfected into cell culture. CAV DNA for transfection was prepared using a Qiagen plasmid purification kit. All constructs were digested with EcoRI restriction endonuclease to release the genomic insert, electrophoresed on a 1% agarose gel and the 2298 bp bands were excised from the gel and purified using the Qiaex II gel plasmid purification kit according to the manufacturer's instructions. The purified CAV DNA was resuspended in sterile 10 mM Tris (pH 8 at 25° C.). The transfection control DNA pEGFP-C2 containing the green fluorescent protein (GFP) downstream from a CMV promoter was prepared as undigested plasmid.

The Marek's disease virus transformed lymphocytic MDCC-MSB1 cell line was used in all experiments. The cells were cultured in RPMI 1640 medium (Sigma Chemical Company, St. Louis, Mo., U.S.A.) supplemented with 2 mM glutamine (Sigma), 2 mM pyruvate (Sigma), 0.2% $NaHCO_3$, 50 μg/mL ampicillin (CSL), 50 μg/mL gentamicin (CSL) and 10% foetal calf serum (Flow Laboratories) (heat inactivated at 52° C.) (complete media referred to as RF10), at 37° C. in 5% $CO_2$. The culture was passaged into fresh medium 24 hours prior to transfection to synchronise the stage of cell cycle. The cells were washed twice in FCS-free RPMI, resuspended at a final concentration of $10^7$ cells/mL and an aliquot of 700 μL was transferred with 10 μg of the relevant DNA to a microfuge tube on ice for each sample. Transfection was achieved through electrointernalisation with a pulse of long duration and low voltage in a 0.4 cm gap electroporation cuvette in a Gene Pulser apparatus (Bio Rad). A pulse was delivered at 400 v, 900 μF, ∞ resistance and extension capacitance. The cells were incubated at room temperature for 5 minutes, then resuspended in 5 mL of prewarmed growth medium. Transfection efficiency was assessed 48 hours later by determining the percentage of cells positive for GFP expression in the control transfection.

Assessment of Replication Competency and Infectivity of Mutant CAV Constructs

The capacity of mutant viruses for infection and replication in cell culture was assessed from MDCC-MSB1 cells transfected with mutant viral constructs. Cultures were serially passaged at a 1/10 dilution at 48 hourly intervals for 10 passages. Samples (48 hourly) were assessed for infectivity by percentage of cells expressing VP3. VP3 expression was detected by an immunofluorescence assay. Infected cells were washed twice and resuspended in 200 mL of phosphate buffered saline (PBS) pH 7.4 and applied to a multiwell slide. The preparations were washed between all incubations with PBS buffer containing 0.1% BSA and 0.05% Tween 20. Cells were fixed in ice cold 90% methanol for 5 minutes and the preparation was blocked for 1 hour with a solution of 5% BSA/PBST at 37° C. in a humidified chamber. The primary antibody was an anti-VP3 mouse monoclonal antibody (TropBio) diluted 1/200 in 0.1% BSA/PBST and incubated for 1 hour at 37° C. in a humidified chamber. The secondary antibody was an anti-mouse sheep monoclonal antibody conjugated to fluorescein isothiocyanate (Dako) diluted 1/100 in 0.1% BSA/PBST and incubated for 1 hour. The percentages of fluorescent cells against passage number were quantified relative to control MSB1 background fluorescence.

Preparations of mutant virus were made from the earliest passage of transfected culture that demonstrated at least 50% infection with CAV. The culture was frozen and thawed three times and then clarified by centrifugation at 6000 g for 10 min. MDCC-MSB1 cells were then reinfected with the virus preparation. Preparation of virus by this method and reinfection of culture was repeated for at least three viral passages in each case. Recovery of replication competent virus was demonstrated by immunofluorescence assay (as described above), PCR of infected lysate followed by Southern blot with a CAV specific probe, and Western blot of infected lysate. A cellular DNA preparation was purified from MDCC-MSB1 cells 48 h after infection with mutant CAV by proteinase K and sodium dodecyl sulphate (SDS) lysis and phenol/chloroform extraction, according to the method of Meehan, B. M., Todd, D., Creelan, J. L., Earle, J. A., Hoey, E. M. and McNulty, M. S. (1992). Characterization of viral DNAs from cells infected with chicken anaemia agent: sequence analysis of the cloned replicative form and transfection capabilities of cloned genome fragments. *Arch Virol* 124, 301-319. The mutant sequence was then amplified using the CAV.2 and CAV.10 primer set and the corresponding PCR reaction conditions described above. The PCR product was electrophoresed on a 1% agarose gel and transferred to Hybond-N (Amersham) nylon membrane using capillary transfer (Sambrook, J., Fritsch, E. F. and Maniatis, T. (1989). *Molecular Cloning, A Laboratory Manual*, (ed. C. Nolan). New York: Cold Spring Harbor Laboratory Press). Following the transfer the membrane was rinsed for 10 min in 6×SSC buffer and exposed to ultraviolet light on a transilluminator for 10 min. A radiolabelled CAV specific probe was made from the CAV genomic clone DNA using random hexamer priming of DNA synthesis with a commercial kit according to the manufacturer's instructions (Boehringer Mannheim). The membrane was soaked in a prehybridisation buffer of 5×SSC, 5× Denhart's solution, 100 μg/mL denatured salmon sperm DNA and 0.5% SDS, to which was added the prepared radiolabelled probe. The probe was hybridised to the blotted DNA overnight at 50° C. The blot was washed three times for 20 min with 2×SSC and 0.1% SDS at 68° C. and a radiographic film was exposed to the blot for 4 h at −70° C.

Western blots were made of a lysate of $10^3$ MDCC-MSB1 cells infected with mutant CAV. Proteins were electrophoresed in 12.5% sodium dodecyl sulphate (SDS) polyacrylamide gels and stained with Coomassie brilliant blue (Laemmli, U. K. (1970). Cleavage of structural proteins during the assembly of the head of bacteriophage T4. *Nature* 227, 680-685). Proteins were electrotransferred onto a polyvinyldifluoride membrane (PVDF: Immobilon, Millipore). Western blots were probed with a mouse monoclonal antibody raised against CAV VP3 (TropBio) diluted 1/2000 in 0.1% BSA/

PBST and incubated for 1 h, followed by a secondary sheep anti-mouse horseradish peroxidase (HRP) conjugate diluted 1/2000, and developed with chemiluminescence substrate (Amersham Pharmacia).

Demonstration of an In Vitro Phenotype for Mutant CAV Viruses

The growth characteristics and cytopathogenicity of mutant viruses was investigated. CAV-mutant viruses were plate titrated using as a control virus generated from pCAU269/7. Titration was performed in an 8×12 multiwell tray (Nunc) in 200 μL culture volumes at $5\times10^5$ MSB1 cells/mL. Serial 10 fold dilutions of virus stock were set up with 6 duplicates, and ranged from final dilution factors of 0.05 through to $0.5\times10^{-10}$. At intervals of 48 hours, infected cells were serially passaged into fresh medium at a dilution of 1 in 4. Each well was scored for evidence of a cytopathogenic effect (CPE). Indications of CPE are enlarged swollen cells, nuclear vacuolation and chromatin assemblies, cell fragmentation and alkalisation of the media. The culture was serially passaged until there was no difference detected between successive passages in the endpoint or lowest dilution at which CPE was observed in 50% of the wells. The observation of CPE was confirmed by immunofluorescence assays of the endpoint dilution. The titre was calculated as the tissue culture infective dose for 50% infectivity ($TCID_{50}$/mL) using the Karber method. Typically 5-7 passages were necessary to establish the endpoint.

The titres of viral stocks obtained by plate titration were confirmed by Fluorescence Activated Cell Sorting (FACS) relative to the parental virus stock as the standard. A ten fold dilution series from 100 to $10^4$ was made of the viral stock in 0.5 mL volumes of RPMI. The viral dilutions were then adsorbed onto $4\times10^6$ MSB1-MDCC cells and resuspended in 4 mL of RF10 in a 6 well culture tray. After 48 h of infection, 2 mL of cells were pelleted by centrifugation at 1500 g for 5 min. The infected cells were prepared for immunofluorescence staining by fixing, permeabilisation and blocking of non-specific surface reactivity. All washes were with 5 mL volumes of 1% FCS and 1 mM sodium azide ($NaN_3$) in PBS. Centrifugation steps between buffer stages were performed at 1500 g for 5 min. The cells were fixed by incubation for 45 min at 4° C. in 1 mL of 3% ultrapure formaldehyde in PBS and 1 mM $NaN_3$. Fixed cells were then washed twice in 5 mL of 0.1 M glycine and 1 mM $NaN_3$, then permeabilised for 5 sec by resuspension in 0.5 mL of 0.1% Triton-X100 and 1 mM $NaN_3$ in PBS, followed by dilution in 4.5 mL of wash buffer and two subsequent wash steps. Following permeabilisation, the cells were handled on ice at all steps. Non-specific reactivity was blocked by a 15 min incubation at 4° C. in 10% FCS and 1 mM $NaN_3$ in PBS, followed by two wash steps. The primary antibody was 50 μl of an anti-VP3 mouse monoclonal antibody (TropBio) diluted 1/50 in wash buffer and cells were incubated in this for 45 min at 4° C. The secondary antibody was an anti-mouse sheep monoclonal antibody conjugated to FITC (Dako) again diluted 1/50 in wash buffer and cells were incubated in this for 45 min at 4° C. Immunostained cells were stored for up to 16 h in 200 μl of 1% ultrapure formaldehyde and 1 mM $NaN_3$ in PBS.

pCAU269/7 viral stocks, which had been plate titrated on three previous occasions, were used as standards for each FACS analysis. Data acquisition and analysis was performed with the Cellquest software. Cytometer instrument settings are given in Table 2.

TABLE 2

Cytometer instrument settings

| parameter | detector | voltage | A gain | mode |
|---|---|---|---|---|
| P1 | FSC | E01 | 1.81 | linear |
| P2 | SSC | 366 | 1.00 | linear |
| P3 | FL1 | 469 | 1.00 | logarithmic |

The gated lymphocyte population was displayed as a histogram with the dependent variable fluorescence intensity. Two distinct normally distributed cell populations were seen; a low fluorescence intensity peak due to background staining and autofluorescence, and a second specific high fluorescence intensity peak. A marker was visually set to include the cells staining with high intensity, specifically for CAV VP3, and to contain <0.05% of cells in the negative control uninfected sample. A standard curve of virus dilution against cell count in the marker region was constructed from the viral stocks. The curves were established independently on three separate occasions. Relative dilutions of test viral stocks were established by calculating the transposition of the FACS curve from a concurrent standard curve.

In vitro cytopathology was assessed by phase contrast microscopy and by staining of fixed cells with a monoclonal antibody specific for VP3 as described above. Cells were counterstained for 2 min in Hoescht stain. Immunofluorescent staining (IFA) was also performed with a mouse polyclonal antiserum raised against the C-terminal region of VP2, at a dilution of 1/100, and a secondary anti-mouse sheep polyclonal antibody conjugated to FITC (Dako) again diluted 1/100 in 0.1% BSA/PBST.

Challenge Model in Embryonated Eggs

A challenge model was developed in embryonated eggs in order to assess infectivity and in vivo phenotype of mutant CAV. The model was initially used to verify equivalence between virus generated from transfection of pCAU269/7 DNA (clone virus) and the parental CAV strain CAU269/7 virus (parental virus). Yolk sac inoculation of 7 day old ermbryos with parental virus, pCAU269/7 and mock MSB1 inocula was repeated on 3 separate occasions. The viruses mut C87R, mut R 101 G, mut H 103 Y, mut R 129 G, mut N 131 P, mut R/K/K 150/151/152 G/A/A, mut D/E 161/162 G/G, mut L 163 P, mut D 169 G and mut E 186 G were then tested in the model compared with clone virus and uninfected MSB1 cell control inocula. The mutant challenge experiments were repeated on two separate occasions.

Inoculation of Embryonated Eggs

Viral stocks for inoculation were prepared from 400 mL of MDCC-MSB1 infected culture in a method adapted from Todd, D., Mackie, D. P., Mawhinney, K. A., Conner, T. J., McNeilly, F. and McNulty, M. S (1990). Development of an enzyme-linked immunosorbent assay to detect serum antibody to chicken anemia agent. *Avian Dis* 34, 359-363. Briefly, 400 mL of culture was sonicated at low frequency in an ice bath, SDS was added to 0.5% and the lysate was incubated for 30 min at 37° C. Cellular debris was removed by pelleting at 10 000 g for 30 min. Virus was then purified by ultracentrifugation at 80 000 g for 3 h at 15° C. Viral pellets were washed in RPMI media and pelleted again at 80 000 g for 3 h. Viral stocks were titrated following the method described above and resuspended at a final titre of $10^{4.5}$ $TCID_{50}$/mL.

Fertile Specific Pathogen Free (SPF) eggs were obtained from SPAFAS Australia Pty. Ltd., James Rd (PO Box 641), Woodend VIC 3442, Australia. The eggs were incubated in a Multiplo Brooder incubator with 300 egg capacity and manual turning. A 0.5 mL virus inoculum, or $10^4$ $TCID_{50}$, was inoculated into the yolk sac of 7 day embryonated eggs using a 24 gauge needle.

Assessment of Infectivity and In Vivo Phenotype for Mutant Viruses

Infectivity was assessed by the detection of viral protein VP3 by immunofluorescence in cells isolated from bone marrow and from thymus, spleen and bursa. Squash preparations were made from bone marrow removed from the femoral medullary cavity. The immunofluorescence assay, described above for cell culture, was used to detect CAV VP3 in bone marrow. In vivo phenotype was assessed by body weight, lymphoid organ weights and lesion scoring of gross pathology in embryos at 21 days. Weights were measured for the whole embryos and the dissected thymus, spleen and bursa of Fabricius. Packed cell volume (PCV) was measured in blood obtained by venipuncture from the vitteline vein or cardiac puncture. Gross pathology was assessed using a standardised system of lesion scoring for target organs of CAV infection.

Lesion Scores

A grading system was established to allow consistent classification of lesion severity associated with CAV infection. Lesions within the thymus, bone marrow, spleen, bursa of Fabricius and incidence of haemorrhage were all scored on a scale of 1 to 4. From these a cumulative lesion score was derived for the overall severity of pathology with scores for the thymus and bone marrow doubled as they are the key target organs for infection. In all cases a score of 1 indicates no pathology. Tables 3-8 outline the scoring system used for gross pathology.

TABLE 3

Thymus score

| Graded points | classification | description |
|---|---|---|
| 4 | severe | ~80-100% loss of lobar parenchyma, +/− severe haemorrhage, +/− severe serosanguinous exudate |
| 3 | moderate | ~50-80% loss of lobar parenchyma, +/− moderate haemorrhage, +/− moderate serosanguinous exudate |
| 2 | mild | minor ~10-50% loss of lobar parenchyma, OR mild haemorrhage, OR mild serosanguinous exudate |

TABLE 4

Bone marrow score

| Graded points | classification | description |
|---|---|---|
| 4 | severe | ~80-100% virtually complete loss of marrow, very pale |
| 3 | moderate | ~30-50% focal loss of marrow, moderately pale |
| 2 | mild | marrow slightly paler than normal OR acutely lytic and haemorrhagic |

TABLE 5

Spleen score

| Graded points | classification | description |
|---|---|---|
| 4 | severe | ~70-90% reduction in size, very pale, +/− subcapsular haemorrhage |
| 3 | moderate | ~30-50% reduction in size, moderately pale, +/− subcapsular haemorrhage |
| 2 | mild | <30% reduction in size, OR slightly pale, OR mild subcapsular haemorrhage |

TABLE 6

Bursa of Fabricius score

| Graded points | classification | description |
|---|---|---|
| 3 | severe | ~50% reduction in size, collapsed folds |
| 2 | mild | ~30% reduction in size |

TABLE 7

Haemorrhage score

| Graded points | classification | description |
|---|---|---|
| 3 | severe | extensive petecchial haemorrhage in subcutaneous tissues and fascial planes OR mesentery OR organs, OR blood visibly watery on venipuncture |
| 2 | moderate to mild | low grade petecchiation present over thighs OR flanks OR wing tips only |

TABLE 8

Total cumulative lesion score

| Graded points | classification |
|---|---|
| 19-13 | severe CAV lesions |
| 13-8 | moderate CAV lesions |
| 8-2 | mild CAV lesions |

Results

I. CAV Vaccine

Construction of CAV with Mutant Genotypes

The constructs mut C87R, mut C 95 S, mut C 97 S, mut R 101 G, mut H 103 Y, mut R 129 G, mut Q 131 P, mut R/K/K 150/151/152 G/A/A, mut D/E 161/162 G/G, mut L 163 P, mut D 169 G and mut E 186 G were made by PCR mutagenesis and subcloning into a full genome CAV clone pCAU269/7. The presence of the mutations in each construct was confirmed by sequencing the final construct twice in both directions across the mutation site. Viruses with mutant genotypes were generated from the transfection of the construct into cell culture. The transfection efficiency was assessed by the number of cells expressing GFP following transfection with control pEGFP plasmid. Transfection efficiency was variable and between 1 and 40% of cells were found to be positive for GFP expression 48 hrs after transfection. pCAU269/7 transfection resulted in an initial phase of transient expression of CAV VP3 as observed by IFA. Transient expression does not necessarily represent active viral replication. A variable number of passages were required before an exponential increase in cell numbers positive for control VP3 expression was evident by IFA. Serial passaging was performed with 1/10 dilutions. Therefore, the exponential increases in cell numbers positive for CAV VP3 represented active viral replication and infection rather than simply maintenance of transfected DNA constructs. All CAV VP2 mutant constructs assayed were found to be infectious and able to replicate to some extent in vitro when assessed in parallel to the pCAU269/7 and mock controls (FIGS. 2 to 12). For each construct, the presence of replication competent virus independent of cell associations was confirmed by lysis and clarification of the transfected culture followed by culture reinfection. This process was serially repeated over four passages. The presence of virus was confirmed by western blotting to detect CAV VP3, by Southern blotting using a CAV specific probe and by PCR of culture digested with DpnI restriction endonuclease to remove any residual transfected DNA. The mutant genotypes were confirmed by sequencing of the PCR product from lysate.

Although replication competent virus was generated from all mutant constructs, the mut C 95 S and mut C 97 S viruses produced maximal log viral titres ($TCID_{50}$/mL) of 1.5 and 1.7 respectively, despite repeated attempts to optimise culture conditions. These viral titres were considered too low for inoculation of embryos and the mut C 95 S and mut C 97 S viruses were not investigated further. Log viral titres ($TCID_{50}$/mL) of 4.5 were obtained for mut C87R, mut R 101 G, mut H 103 Y, mut R 129 G, mut N 131 P, mut R/K/K 150/151/152 G/A/A, mut D/E 161/162 G/G, mut L 163 P, mut D 169 G and mut E 186 G constructs when prepared over 4 passages in a final volume of 400 mL of infected culture, concentrated by ultracentrifugation and resuspended at equivalent titres (Table 9). The titres were considered adequate for inoculation of embryos and 0.5 mL of the stock or $10^{4.2}$ $TCID_{50}$ was used.

TABLE 9

Titres for concentrated viral stocks used for inoculation of embryos. Titres were established by plate titration and by FACS by correlation with a clone virus standard. Stocks were assessed by PCR and sequencing to confirm the mutant genotype. FACS titre estimated accuracy of +/−$10^{0.5}$ $TCID_{50}$/mL.

| mutant | log FACS titre $TCID_{50}$/mL | log plate titre $TCID_{50}$/mL | PCR on stock | Sequencing of stock for mutation |
|---|---|---|---|---|
| pCAU269/7 | 4.5 | 4.5 | positive | correct |
| mut C87R | 4.5 | 4.5 | positive | correct |
| mut C 95 S | 1.5 | 1.5 | positive | correct |
| mut C 97 S | 1.5 | 1.7 | positive | correct |
| mut R 101 G | 4.5 | 4.5 | positive | correct |
| mut H 103 Y | 4.5 | 4.5 | positive | correct |
| mut R 129 G | 4.5 | 4.5 | positive | correct |
| mut L 131 P | 4.5 | 4.8 | positive | correct |

TABLE 9-continued

Titres for concentrated viral stocks used for inoculation of embryos. Titres were established by plate titration and by FACS by correlation with a clone virus standard. Stocks were assessed by PCR and sequencing to confirm the mutant genotype. FACS titre estimated accuracy of +/−$10^{0.5}$ $TCID_{50}$/mL.

| mutant | log FACS titre $TCID_{50}$/mL | log plate titre $TCID_{50}$/mL | PCR on stock | Sequencing of stock for mutation |
|---|---|---|---|---|
| mutR/K/K150/151/152G/A/A | 4.5 | 4.1 | positive | correct |
| mutD/E161/162G/G | 4.5 | 4.5 | positive | correct |
| mut163 | 4.5 | 4.5 | positive | correct |
| mut D 169 G | 4.5 | 3.9 | positive | correct |
| mut E 186 G | Not done | 4.5 | positive | correct |

Infection Model in Embryonated Eggs

A series of infection experiments were performed. Experiments 1 and 2 established equivalent infectivity and virulence between the parental virus and virus generated from the cloned construct, pCAU269/7 (clone virus). All birds in both the parental and clone virus treatment groups had lesions within the thymus, bone marrow, spleen and haemorrhage categorised as severe CAV pathology. There was no significant difference in thymus, bone marrow, spleen, haemorrhage and cumulative lesion scores for the two groups as determined by a Mann Whitney test. Both groups were significantly different from the uninfected group in all cases with the exception of the bone marrow scores for the clone group. Severe pathology associated with wild type virus infection (parental or clone virus) can be summarised as follows: mild to moderate petecchiation was found in the fascial and subcutaneous tissues in all chicks or embryos. The spleen was reduced between 50-80% in size and in general appeared abnormally pale and had subcapsular haemorrhages. In all birds the reduction in the size of all thymic lobes was graded as severe, and in the majority the appearance was of either haemorrhage into the lobes or a subcapsular, gelatinous, serosanguinous exudate in the lobes, consistent with acute cytolysis. There was a reduction in bone marrow content, and either a pale fatty appearance to the marrow or severe acute haemorrhage and lysis. In a minority of birds the bursa of Fabricius was reduced in size and the capsule and parenchymal folds appeared grossly collapsed.

Experiments 3-12 involved infection with mutant viruses and clone virus and uninfected controls. Statistical analyses of lesion scores, body weights, lymphoid organ weights compared to body weights and the size of lymphocyte populations in the thymus, Bursa of Fabricius and spleen in embryos infected mutant viruses or wild type virus and uninfected controls are outlined in Tables 10-17. In summary, lesion scores were significantly less in embryos infected with the mutant viruses than in those infected with the wild type virus, and in most cases lesions were significantly less severe in most of the lymphoid organs (Table 10). Similarly a significant difference was found in body weight, in thymus/bodyweight and spleen/bodyweight ratios, and in most cases bursa/bodyweight ratio between embryos infected with mutant viruses and those infected with cloned wild type CAU269/7 (Table 11).

TABLE 10

Lesion scores in the lymphoid tissues, haemorrhage scores and cumulative scores, in embryos infected with CAV.

| Treatment group¶ | Median lesion scores# Thymus S | R | n | $P_1$ | $P_2$ | Spleen S | R | n | $P_1$ | $P_2$ | Bursa S | R | n | $P_1$ | $P_2$ |
|---|---|---|---|---|---|---|---|---|---|---|---|---|---|---|---|
| CAU269/7 | 3 | 1-4 | 24 | NA | *** | 3 | 1-4 | 14 | NA | *** | 1 | 1-3 | 24 | NA | ‡ |
| Mut C87R | 2 | 1-4 | 23 | *** | *** | 2 | 1-4 | 23 | *** | *** | 1 | 1-2 | 24 | ‡ | ‡ |
| Mut R101G | 1 | 1-3 | 11 | *** | ** | 2 | 1-2 | 11 | ** | *** | 1 | 1-2 | 11 | ‡ | ‡ |
| Mut H103Y | 2 | 1-4 | 22 | *** | ** | 1 | 1-3 | 22 | *** | *** | 1 | 1-3 | 14 | ‡ | ‡ |
| Mut R129G | 3 | 1-4 | 20 | *** | *** | 1 | 1-3 | 18 | *** | * | 1 | 1-2 | 18 | ‡ | ‡ |
| Mut Q131P | 2 | 1-4 | 14 | *** | *** | 2 | 1-4 | 14 | * | *** | 1 | 1-2 | 14 | ‡ | ‡ |
| Mut R/K/K150/ 151/152G/A/A | 2 | 1-3 | 19 | *** | *** | 1 | 1-3 | 19 | *** | *** | 1 | 1-2 | 18 | ‡ | ‡ |
| Mut D/E161/162G/G | 3 | 1-3 | 5 | * | ** | 1 | 1-2 | 5 | ** | ‡ | 1 | 1-2 | 5 | ‡ | ‡ |
| Mut L163P | 2 | 1-5 | 20 | *** | *** | 1 | 1-4 | 20 | *** | * | 1 | 1-2 | 20 | ‡ | ‡ |
| Mut D169G | 3 | 2-4 | 10 | ‡ | *** | 3 | 1-4 | 10 | ‡ | *** | 1 | 1-2 | 10 | ‡ | ‡ |
| Mut E186G | 2 | 1-2 | 6 | *** | * | 1 | 1-2 | 6 | ** | ‡ | 1 | 1-2 | 6 | ‡ | ‡ |
| Uninfected | 1 | 1-1 | 17 | *** | NA | 1 | 1-1 | 17 | *** | NA | 1 | 1-1 | 17 | ‡ | ‡ |

| Treatment group¶ | Median lesion scores# Bone marrow S | R | n | $P_1$ | $P_2$ | Haemorrhage S | R | n | $P_1$ | $P_2$ | Cumulative scores S | R | n | $P_1$ | $P_2$ |
|---|---|---|---|---|---|---|---|---|---|---|---|---|---|---|---|
| CAU269/7 | 3 | 1-4 | 24 | NA | *** | 2 | 1-4 | 24 | NA | *** | 13 | 3-18 | 14 | NA | *** |
| Mut C87R | 2 | 1-4 | 13 | *** | *** | 1 | 1-2 | 23 | *** | ‡ | 6 | 2-8 | 13 | *** | *** |
| Mut R101G | 2 | 1-2 | 11 | *** | *** | 2 | 1-2 | 11 | ** | *** | 5 | 3-8 | 13 | *** | *** |
| Mut H103Y | 2 | 1-4 | 13 | *** | *** | 1 | 1-2 | 22 | ** | ‡ | 6 | 1-17 | 13 | *** | *** |
| Mut R129G | 1 | 1-2 | 10 | *** | ‡ | 1 | 1-2 | 19 | ** | * | 4 | 2-9 | 10 | *** | *** |
| Mut Q131P | 2 | 1-2 | 7 | *** | *** | 1 | 1-2 | 14 | * | ‡ | 6 | 2-8 | 6 | *** | *** |
| Mut R/K/K150/ 151/152G/A/A | 2 | 1-4 | 9 | * | ** | 2 | 1-3 | 19 | ‡ | *** | 7 | 1-14 | 9 | ** | *** |
| Mut D/E161/ 162G/G | 1 | 1-2 | 5 | ** | ‡ | 1 | 1-1 | 5 | * | ‡ | 6 | 1-7 | 5 | ** | *** |
| Mut L163P | 2 | 1-3 | 10 | * | ** | 1 | 1-3 | 20 | ** | ‡ | 9 | 1-12 | 10 | ** | *** |
| Mut D169G | 2 | 1-4 | 10 | ‡ | *** | 2 | 1-3 | 10 | ‡ | *** | 9 | 6-13 | 10 | * | *** |
| Mut E186G | 1 | 1-2 | 6 | ** | ‡ | 1 | 1-2 | 6 | ** | ‡ | 3 | 2-5 | 6 | *** | ** |
| Uninfected | 1 | 1-1 | 28 | *** | NA | 1 | 1-1 | 18 | *** | NA | 1 | 1-1 | 17 | *** | NA |

¶virus inoculated into E7 embryos
#median lesion scores
S median score
n group size
R range
$P_1$ P value for Mann Whitney test between CAU269.7 and treatment group
$P_2$ P value for Mann Whitney test between control negative and treatment group
* P value significant at 0.05 level
** P value significant at 0.01 level
*** P value significant at 0.001 level
‡ P value not significant at 0.05 lev

TABLE 11

Bodyweight, thymus:bodyweight, spleen:bodyweight, and bursa:bodyweight ratios for embryos infected with CAV.

| Treatment Group¶ | Bodyweight# μ | SEM | n | $P_1$ | $P_2$ | Thymus:bodyweight μ | SD | n | $P_1$ | $P_2$ | Spleen:bodyweight μ | SD | n | $P_1$ | $P_2$ | Bursa:bodyweight μ | SD | n | $P_1$ | $P_2$ |
|---|---|---|---|---|---|---|---|---|---|---|---|---|---|---|---|---|---|---|---|---|
| CAU269/7 | 24.8 | 1.9 | 24 | NA | *** | 5.75 | 2.4 | 9 | NA | *** | 0.21 | 0.06 | 9 | NA | *** | 0.64 | 0.30 | 9 | NA | ** |
| Mut C87R | 34.60 | 1.4 | 20 | *** | ‡ | 9.85 | 3.3 | 23 | *** | ‡ | 0.34 | 0.1 | 23 | ** | ‡ | 0.91 | 0.40 | 23 | * | ** |
| Mut R101G | 37.95 | 1.9 | 8 | *** | ‡ | 10.54 | 2.0 | 7 | *** | ‡ | 0.37 | 0.07 | 7 | *** | ‡ | 1.01 | 0.24 | 7 | ** | ‡ |
| Mut H103Y | 35.02 | 1.5 | 10 | *** | ‡ | 9.94 | 3.5 | 22 | *** | ‡ | 0.33 | 0.13 | 22 | ** | ‡ | 0.78 | 0.26 | 22 | ‡ | *** |
| Mut R129G | 34.13 | 1.8 | 14 | ** | ‡ | 10.68 | 3.5 | 19 | *** | ‡ | 0.39 | 0.12 | 19 | *** | ‡ | 1.03 | 0.35 | 19 | ** | ‡ |
| Mut Q131P | 36.95 | 1.6 | 10 | *** | ‡ | 9.38 | 3.4 | 13 | ** | ‡ | 0.39 | 0.2 | 13 | ** | ‡ | 1.08 | 0.69 | 13 | * | ‡ |
| Mut R/K/K150/ 151/152G/A/A | 31.33 | 1.8 | 16 | ** | ‡ | 10.11 | 2.4 | 18 | *** | ‡ | 0.32 | 0.1 | 18 | ** | ‡ | 0.82 | 0.36 | 18 | ‡ | ** |
| Mut D/E161/ 162G/G | 34.38 | 3.8 | 5 | * | ‡ | 11.35 | 3.4 | 5 | *** | ‡ | 0.39 | 0.05 | 5 | *** | ‡ | 0.78 | 0.36 | 5 | ‡ | * |
| Mut L163P | 32.21 | 1.5 | 18 | * | ‡ | 10.18 | 3.4 | 20 | *** | ‡ | 0.42 | 0.1 | 20 | *** | ‡ | 1.01 | 0.37 | 20 | ** | ‡ |
| Mut D169G | 33.10 | 3.5 | 10 | * | ‡ | 9.15 | 2.5 | 9 | ** | ‡ | 0.28 | 0.1 | 9 | * | * | 1.40 | 1.10 | 9 | * | ‡ |

TABLE 11-continued

Bodyweight, thymus:bodyweight, spleen:bodyweight, and bursa:bodyweight ratios for embryos infected with CAV.

| Treatment | Bodyweight[#] | | | | | Thymus:bodyweight | | | | | Spleen:bodyweight | | | | | Bursa:bodyweight | | | | |
|---|---|---|---|---|---|---|---|---|---|---|---|---|---|---|---|---|---|---|---|---|
| Group¶ | μ | SEM | n | $P_1$ | $P_2$ | μ | SD | n | $P_1$ | $P_2$ | μ | SD | n | $P_1$ | $P_2$ | μ | SD | n | $P_1$ | $P_2$ |
| Mut E186G | 42.94 | 0.8 | 6 | *** | ‡ | 10.03 | 2.7 | 6 | ** | ‡ | 0.36 | 0.1 | 6 | *** | ‡ | 1.06 | 0.14 | 6 | ** | ‡ |
| Uninfected | 37.12 | 2.4 | 11 | *** | NA | 10.99 | 4.2 | 16 | *** | NA | 0.39 | 0.1 | 16 | *** | NA | 1.23 | 0.52 | 16 | ** | NA |

¶virus inoculated into E7 embryos
μ mean weight
#(g), or, mean organ weight (mg):bodyweight (g)
SEM standard error of the mean
SD standard deviation
n number in treatment group
$P_1$ P value for t-test between CAU269/7 and treatment group
$P_2$ P value for t-test between control negative and treatment group
* P value significant at 0.05 level
** P value significant at 0.01 level
*** P value significant at 0.001 level
‡ P value not significant at 0.05 level Examination of Lymphocyte Populations The effect of virus infection on lymphocyte populations in major lymphoid organs was assessed. The thymus, spleen and bursa were dissected from the embryos and placed into chilled sterile PBS wash buffer containing 1% BSA and 1 mM NaN3. The tissue was, roughly macerated and filtered through a 50 mm pore nylon mesh. The filter was flushed with chilled PBS wash buffer and the tissue homogenate was collected and mixed thoroughly. The weight of residual tissue on the filter was compared to the original filter weight. Extracted cells were pelleted at 2000 g for 7 min and resuspended in 4 ml of PBS wash buffer. The cell suspension was purified by centrifugation for 5 min at 1000 g over a Ficoll-Paque (Amersham Pharmacia Biotech) gradient and the collected cells were washed twice in PBS wash buffer. Triplicate Coulter counter and haemocytometer readings were taken.

Examination of the size of the lymphocyte populations in the thymus, spleen and bursa by (Table 12) established that all mutants caused significantly less depletion of lymphocyte populations than the virulent wild type virus.

Fluorescence Activated Cell Sorting (FACS) of Lymphocyte Populations

The concentrations were optimised for mAbs mouse anti-chicken TCR1 (Southern Biotechnology), mouse anti-chicken TCR2 (Southern Biotechnology), mouse anti-chicken TCR3 (Southern biotechnology), mouse anti-chicken CD4-FITC conjugate (Southern Biotechnology), mouse anti-chicken CD8-FITC conjugate (Southern Biotechnology) and mouse anti-chicken AvBu-1 (supplied by Dr. Fred Davidson, Compton Laboratories, UK). Two White Leghorn Chickens (SPAFAS) were euthanased by immersion in a $CO_2$ chamber and the spleens, thymuses and bursae were removed at post mortem and placed into PBS. Pooled leukocytes were purified as described above. To determine optimal concentrations of the antibodies used for FACS analysis, the mouse anti-chicken TCR1 mAb was assessed at dilutions of 1/100, 1/1000 and 1/5000. The mouse anti-chicken TCR2 mAb was assessed at dilutions of 1/50, 1/100 and 1/1000. The mAbs mouse anti-chicken TCR3 and mouse anti-chicken AvBu-1 were assessed at dilutions of 1/20, 1/50 and 1/100. The mouse anti-chicken CD4-FITC conjugate and mouse anti-chicken CD8-FITC conjugate mAbs were titred at dilutions of 1/20, 1/50, 1/100, 1/200 and 1/500. Optimal dilutions were decided based on the highest antibody dilution at which there was clearest definition of background and signal staining on FACS analysis, and also peak intensity for specific staining.

Lymphocyte populations isolated from the thymus and spleen of each embryo were analysed for the proportion of cells positive on FACS analysis for the TCR1, TCR2, TCR3, CD4 and CD8 cell surface markers using a double staining protocol. For each embryo eight staining treatments were performed on duplicate samples of $10^6$ lymphocytes. In the first staining step, cells were incubated for 30 min at 4° C. with either mouse anti-chicken TCR1 mAb at a 1/1000 dilution in PBS wash buffer, or mouse anti-chicken TCR2 mAb at a 1/100 dilution, or mouse anti-chicken TCR3 mAb at a 1/100 dilution, or all 3 mAbs in combination. The cells were washed and then incubated with the secondary rabbit anti-mouse-phycoerythrin (PE) conjugate (Sigma Aldrich) at a 1/1500 dilution for 30 min at 4° C., then blocked by incubation with 10% normal mouse serum (Sigma Aldrich) in PBS for 30 min at 4° C. In the third staining step each set of 4 treatments was incubated for 30 min at 4° C. with either mouse anti-chicken CD4-FITC conjugate at a 1/100 dilution, or mouse anti-chicken CD8-FITC conjugate at a 1/100 dilution.

Lymphocyte samples from the thymus, spleen and bursa of a selection of the experimental chicks were stained and analysed for the B-cell marker avian Bu-1 (AvBu-1). Samples of 106 lymphocytes were incubated with the mAb mouse anti-chicken AvBu-1 at a 1/200 dilution followed by the secondary rabbit anti-mouse-PE conjugate mAb at a 1/1500 dilution for 30 min at 4° C.

Proportions of double positive and single positive cells were analysed using a cytofluorometer.

Data was analysed using Cellquest software (Becton Dickinson). Sample populations of 10E8 cells were graphed on density plots, with intensity of FITC staining displayed on the X-axis and intensity PE staining displayed on the Y-axis. Quadrants established from plots of control cells were used to delineate positively and negatively stained populations. The absolute size and proportion of the total lymphocyte pool was calculated for the lymphocyte subsets.

Analysis of different lymphocyte subsets in the thymus, spleen and bursa using fluorescence activated cell sorting established that the mutant viruses caused significantly less depression in the numbers of CD4+TCR−, CD4+TCR1+, CD4+TCR2+, and in some cases CD4+TCR3+, thymocytes (Table 13), significantly less depression in the numbers of CD8+TCR−, and in some cases CD8+TCR1+, CD8+TCR2+ and CD8+TCR3+, thymocytes (Table 14). In general the mutants also caused less depression in these subsets of splenocytes (Tables 15 and 16). In some cases, the mutants also had significantly less effect on B lymphocyte populations than the wild type virus (Table 17). These findings establish that the mutation of VP2 significantly decreases the immunosuppressive effects of CAV.

TABLE 12

Lymphocyte populations from the thymus, spleen and bursa of E21 embryos infected with wild type and VP2 mutant CAU269/7.

| Treatment | Mean lymphocyte populations ($\times 10^6$)[#] | | | | | | | | | | | | | | |
|---|---|---|---|---|---|---|---|---|---|---|---|---|---|---|---|
| | Thymus | | | | | Spleen | | | | | Bursa | | | | |
| group[¶] | μ | SEM | n | $P_1$ | $P_2$ | μ | SEM | n | $P_1$ | $P_2$ | μ | SEM | n | $P_1$ | $P_2$ |
| CAU269/7 | 760 | 22 | 9 | ** | NA | 27 | 2 | 9 | ‡ | NA | 13 | 2 | 9 | *** | NA |
| Mut C87R | 4002 | 78 | 10 | ‡ | ** | 27 | 4 | 10 | ‡ | ‡ | 49 | 10 | 10 | ‡ | ** |
| Mut R101G | 1969 | 42 | 7 | ‡ | ** | 93 | 22 | 7 | ** | ** | 355 | 30 | 7 | * | *** |
| Mut H103Y | 4374 | 61 | 9 | ‡ | *** | 102 | 41 | 9 | ‡ | * | 751 | 24 | 9 | ‡ | ** |
| Mut R129G | 6080 | 28 | 7 | ‡ | * | 155 | 64 | 7 | * | * | 118 | 6 | 7 | ‡ | * |
| Mut Q131P | 3735 | 85 | 5 | ‡ | *** | 36 | 2 | 5 | ‡ | ‡ | 73 | 3 | 5 | ‡ | ** |
| Mut R/K/K150/ 151/152G/A/A | 2452 | 74 | 5 | ‡ | ** | 105 | 23 | 5 | ** | *** | 120 | 9 | 5 | ** | *** |
| Mut D/E161/ 162G/G | 5664 | 370 | 7 | ‡ | * | 110 | 34 | 7 | * | ** | 60 | 2 | 7 | ‡ | ** |
| Mut L163P | 1838 | 22 | 7 | ‡ | ** | 163 | 5 | 7 | ** | *** | 107 | 3 | 7 | ‡ | ** |
| Mut D169G | 4678 | 173 | 9 | ‡ | * | 248 | 8 | 9 | ** | *** | 341 | 82 | 9 | ** | *** |
| Mut E186G | 1938 | 94 | 10 | * | *** | 80 | 2 | 10 | ‡ | * | 105 | 2 | 10 | * | *** |
| Uninfected | 3824 | 11 | 7 | NA | ** | 31 | 2 | 7 | NA | ‡ | 62 | 1 | 7 | NA | *** |

¶virus inoculated into E7 embryos
#population size measured by coulter counter
μ mean
SEM standard error of the mean
n sample size
$P_1$ P value for t-test between uninfected and treatment group
$P_2$ P value for t-test between CAU269/7 and treatment group
* P value significant at 0.05 level
** P value significant at 0.01 level
*** P value significant at 0.001 level
‡ P value not significant at 0.05 level

TABLE 13

$CD4^+$ thymocyte populations from E21 embryos infected with VP2 mutant and wild type CAU269/7.

| Treatment | Mean $CD4^+$ thymocyte populations ($\times 10^6$)[#] | | | | | | | | | | | | | | | | | | | |
|---|---|---|---|---|---|---|---|---|---|---|---|---|---|---|---|---|---|---|---|---|
| | $TCR^-$ | | | | | $TCR1^+$ | | | | | $TCR2^+$ | | | | | $TCR3^+$ | | | | |
| group[¶] | μ | SEM | n | $P_1$ | $P_2$ | μ | SEM | n | $P_1$ | $P_2$ | μ | SEM | n | $P_1$ | $P_2$ | μ | SEM | n | $P_1$ | $P_2$ |
| CAU269/7 | 133 | 29 | 19 | *** | NA | 7 | 2 | 7 | ** | NA | 35 | 24 | 7 | ** | NA | 29 | 15 | 7 | NA | * |
| Mut C87R | 728 | 251 | 18 | ‡ | ** | 110 | 28 | 10 | ‡ | ** | 222 | 85 | 11 | * | * | 66 | 33 | 10 | ‡ | ** |
| Mut R101G | 4008 | 1362 | 11 | ** | *** | 121 | 23 | 8 | ‡ | *** | 355 | 151 | 7 | ‡ | * | 167 | 80 | 7 | ‡ | * |
| Mut H103Y | 1985 | 21 | 22 | ‡ | * | 202 | 48 | 8 | ‡ | ** | 332 | 64 | 8 | ‡ | *** | 295 | 75 | 8 | ‡ | ** |
| Mut R129G | 9529 | 1839 | 20 | *** | *** | 323 | 134 | 7 | ‡ | ** | 2060 | 577 | 7 | * | ** | 1311 | 418 | 7 | * | *** |
| Mut Q131P | 2747 | 366 | 18 | *** | *** | 87 | 32 | 6 | ‡ | ** | 143 | 45 | 6 | * | * | 99 | 50 | 6 | ‡ | ‡ |
| Mut R/K/K 150/151/ 152G/A/A | 885 | 184 | 15 | ‡ | *** | 89 | 31 | 5 | ‡ | *** | 177 | 70 | 5 | * | * | 214 | 82 | 5 | ‡ | ** |
| Mut D/E 161/162G/G | 524 | 170 | 12 | ‡ | ** | 105 | 66 | 5 | ‡ | * | 1291 | 114 | 5 | ‡ | * | 869 | 77 | 5 | ‡ | ‡ |
| Mut L163P | 8392 | 1546 | 8 | *** | *** | 75 | 16 | 7 | ‡ | *** | 544 | 277 | 7 | ‡ | * | 501 | 238 | 7 | ‡ | * |
| Mut D169G | 3204 | 1027 | 18 | *** | *** | 248 | 153 | 5 | ‡ | *** | 1315 | 530 | 5 | ‡ | ** | 639 | 287 | 7 | ‡ | *** |
| Mut E186G | 8495 | 900 | 8 | *** | *** | 195 | 32 | 8 | * | *** | 2911 | 926 | 8 | ** | ** | 1427 | 492 | 8 | * | ** |
| Uninfected | 977 | 178 | 19 | NA | *** | 98 | 35 | 7 | NA | ** | 692 | 213 | 7 | NA | ** | 409 | 165 | 7 | * | NA |

¶virus inoculated into E7 embryos
#populations immunostained and analysed by FACS
μ mean
SEM standard error of the mean
n sample size
$P_1$ P value for t-test between uninfected and treatment group
$P_2$ P value for t-test between CAU269/7 and treatment group
* P value significant at 0.05 level
** P value significant at 0.01 level
*** P value significant at 0.001 level
‡ P value not significant at 0.05 level

TABLE 14

CD8⁺ thymocyte populations from E21 embryos infected with VP2 mutant and wild type CAU269/7.

| Treatment | Mean CD8⁺ thymocyte populations ($\times 10^6$)[#] | | | | | | | | | | | | | | | | | | | |
|---|---|---|---|---|---|---|---|---|---|---|---|---|---|---|---|---|---|---|---|---|
| | TCR⁻ | | | | | TCR1⁺ | | | | | TCR2⁺ | | | | | TCR3⁺ | | | | |
| group¶ | μ | SEM | n | $P_1$ | $P_2$ | μ | SEM | n | $P_1$ | $P_2$ | μ | SEM | n | $P_1$ | $P_2$ | μ | SEM | n | $P_1$ | $P_2$ |
| CAU269/7 | 190 | 49 | 19 | *** | NA | 15 | 4 | 7 | ** | NA | 28 | 22 | 7 | *** | NA | 20 | 15 | 7 | NA | * |
| Mut C87R | 560 | 49 | 18 | ‡ | * | 34 | 8 | 10 | ‡ | *** | 259 | 72 | 11 | ‡ | ** | 147 | 33 | 10 | ‡ | * |
| Mut R101G | 5127 | 1237 | 11 | * | *** | 461 | 249 | 8 | ‡ | * | 60 | 9 | 7 | *** | ‡ | 255 | 80 | 7 | ‡ | * |
| Mut H103Y | 2016 | 174 | 22 | * | *** | 229 | 33 | 8 | * | *** | 115 | 64 | 8 | ‡ | ‡ | 313 | 75 | 8 | ‡ | ** |
| Mut R129G | 12893 | 2153 | 20 | ** | *** | 503 | 148 | 7 | ** | ** | 172 | 50 | 7 | ‡ | ** | 691 | 418 | 7 | ‡ | * |
| Mut Q131P | 2830 | 479 | 18 | *** | *** | 66 | 35 | 6 | ‡ | ‡ | 64 | 32 | 6 | ‡ | *** | 61 | 50 | 6 | * | ** |
| Mut R/K/K 150/151/ 152G/A/A | 595 | 101 | 15 | ** | *** | 174 | 111 | 5 | ‡ | * | 49 | 18 | 5 | ‡ | *** | 258 | 82 | 5 | ‡ | ** |
| Mut D/E 161/162G/G | 816 | 153 | 12 | ‡ | *** | 188 | 115 | 5 | ‡ | ‡ | 258 | 103 | 5 | ‡ | ‡ | 1704 | 77 | 5 | ‡ | ‡ |
| Mut L163P | 8356 | 80 | 8 | ** | *** | 121 | 28 | 7 | ‡ | *** | 150 | 41 | 7 | ‡ | ** | 619 | 238 | 7 | ‡ | ** |
| Mut D169G | 4162 | 1027 | 18 | *** | *** | 189 | 64 | 5 | ‡ | ** | 96 | 34 | 5 | ‡ | * | 333 | 287 | 7 | ‡ | * |
| Mut E186G | 10172 | 1203 | 8 | *** | *** | 230 | 18 | 8 | ** | *** | 505 | 116 | 8 | ** | *** | 1919 | 492 | 8 | ‡ | ‡ |
| Uninfected | 1370 | 288 | 19 | NA | *** | 118 | 93 | 7 | NA | ** | 159 | 14 | 7 | NA | *** | 93 | 25 | 7 | * | NA |

¶virus inoculated into E7 embryos
#populations immunostained and analysed by FACS
μ mean
SEM standard error of the mean
n sample size
$P_1$ P value for t-test between uninfected and treatment group
$P_2$ P value for t-test between CAU269/7 and treatment group
* P value significant at 0.05 level
** P value significant at 0.01 level
*** P value significant at 0.001 level
‡ P value not significant at 0.05 level

TABLE 15

CD4⁺ splenocyte populations from E21 embryos infected with VP2 mutant and wild type CAU269/7.

| Treatment | Mean CD4⁺ splenocyte populations ($\times 10^4$)[#] | | | | | | | | | | | | | | | | | | | |
|---|---|---|---|---|---|---|---|---|---|---|---|---|---|---|---|---|---|---|---|---|
| | TCR⁻ | | | | | TCR1⁺ | | | | | TCR2⁺ | | | | | TCR3⁺ | | | | |
| group¶ | μ | SEM | n | $P_1$ | $P_2$ | μ | SEM | n | $P_1$ | $P_2$ | μ | SEM | n | $P_1$ | $P_2$ | μ | SEM | n | $P_1$ | $P_2$ |
| CAU269/7 | 2 | 1 | 24 | *** | NA | 11 | 6 | 8 | * | NA | 78 | 48 | 8 | * | NA | 133 | 95 | 8 | NA | * |
| Mut C87R | 3 | 2 | 31 | *** | ‡ | 519 | 30 | 11 | ‡ | * | 307 | 101 | 11 | ‡ | * | 417 | 18 | 11 | ‡ | ‡ |
| Mut R101G | 20 | 8 | 11 | ‡ | ** | 17 | 6 | 8 | ‡ | * | 32 | 1 | 7 | * | ** | 17 | 6 | 7 | * | ** |
| Mut H103Y | 56 | 25 | 27 | ‡ | * | 122 | 6 | 8 | * | * | 7058 | 291 | 7 | * | ** | 11192 | 61 | 8 | * | ** |
| Mut R129G | 6 | 1 | 5 | * | ** | 210 | 190 | 7 | ‡ | * | 142 | 119 | 7 | ‡ | ‡ | 97 | 72 | 7 | ‡ | ‡ |
| mut Q131P | 23 | 8 | 18 | ‡ | *** | 385 | 17 | 6 | ‡ | * | 155 | 71 | 5 | ‡ | ‡ | 93 | 74 | 6 | ‡ | ‡ |
| mut R/K/K 150/151/ 152G/A/A | 14 | 5 | 15 | ‡ | *** | 2319 | 13 | 5 | ‡ | * | 2223 | 55 | 5 | * | *** | 3860 | 142 | 5 | ** | ** |
| Mut D/E 161/162G/G | 40 | 9 | 12 | ‡ | *** | 13 | 4 | 5 | ‡ | *** | 16 | 8 | 5 | ‡ | ** | 13 | 5 | 5 | ‡ | ** |
| Mut L163P | 24 | 12 | 10 | ‡ | * | 121 | 83 | 7 | ‡ | * | 64 | 28 | 6 | * | ** | 57 | 19 | 7 | *** | *** |
| Mut D169G | 241 | 14 | 29 | ‡ | ‡ | 4363 | 3 | 10 | ‡ | * | 3226 | 273 | 10 | ‡ | * | 3071 | 263 | 10 | ‡ | * |
| Mut E186G | 7 | 1 | 10 | ** | ** | 200 | 10 | 8 | ‡ | ‡ | 40 | 1 | 8 | ‡ | * | 50 | 10 | 8 | ‡ | ** |
| Uninfected | 17 | 4 | 19 | NA | *** | 98 | 35 | 7 | NA | ** | 771 | 42 | 8 | NA | * | 506 | 217 | 7 | * | NA |

¶virus inoculated into E7 embryos
#populations immunostained and analysed by FACS
μ mean
SEM standard error of the mean
n sample size
$P_1$ P value for t-test between uninfected and treatment group
$P_2$ P value for t-test between CAU269/7 and treatment group
* P value significant at 0.05 level
** P value significant at 0.01 level
*** P value significant at 0.001 level
‡ P value not significant at 0.05

TABLE 16

CD8+ splenocyte populations from E21 embryos infected with VP2 mutant and wild type CAU269/7.

| Treatment | Mean CD8+ splenocyte populations (×10$^4$)# | | | | | | | | | | | | | | | | | | | |
|---|---|---|---|---|---|---|---|---|---|---|---|---|---|---|---|---|---|---|---|---|
| | TCR$^-$ | | | | | TCR1$^+$ | | | | | TCR2$^+$ | | | | | TCR3$^+$ | | | | |
| group¶ | μ | SEM | n | $P_1$ | $P_2$ | μ | SEM | n | $P_1$ | $P_2$ | μ | SEM | n | $P_1$ | $P_2$ | μ | SEM | n | $P_1$ | $P_2$ |
| CAU269/7 | 6 | 2 | 24 | * | NA | 45 | 24 | 8 | ** | NA | 152 | 11 | 8 | * | NA | 99 | 7 | 8 | ** | NA |
| Mut C87R | 5 | 2 | 32 | * | *** | 289 | 10 | 11 | ‡ | * | 755 | 28 | 11 | ‡ | * | 967 | 73 | 8 | ‡ | * |
| Mut R101G | 16 | 7 | 10 | ‡ | * | 23 | 7 | 8 | * | ** | 16 | 4 | 7 | * | ** | 25 | 9 | 7 | * | ** |
| Mut H103Y | 63 | 4 | 27 | ‡ | ‡ | 1870 | 95 | 9 | * | * | 6417 | 28 | 9 | * | * | 7805 | 28 | 9 | ** | ** |
| Mut R129G | 136 | 9 | 9 | * | ** | 128 | 107 | 7 | ‡ | ‡ | 45 | 18 | 7 | * | ** | 62 | 35 | 7 | * | ** |
| Mut Q131P | 28 | 1 | 18 | ‡ | ** | 503 | 41 | 6 | ‡ | ‡ | 621 | 32 | 6 | ‡ | * | 954 | 57 | 5 | ‡ | * |
| Mut R/K/K 150/151/ 152G/A/A | 8 | 3 | 15 | ‡ | ‡ | 2246 | 64 | 5 | ** | *** | 1312 | 383 | 5 | * | ** | 1410 | 36 | 5 | ** | *** |
| Mut D/E 161/162G/G | 39 | 6 | 10 | ‡ | *** | 20 | 5 | 5 | ** | *** | 13 | 3 | 5 | ** | *** | 23 | 11 | 5 | * | ** |
| Mut L163P | 22 | 5 | 11 | ‡ | ** | 38 | 13 | 7 | ** | *** | 32 | 6 | 8 | ‡ | ‡ | 54 | 24 | 6 | * | ** |
| Mut D169G | 141 | 7 | 30 | ‡ | * | 1922 | 69 | 10 | ‡ | * | 1538 | 96 | 10 | ‡ | * | 801 | 55 | 10 | ‡ | * |
| Mut E186G | 5 | 2 | 10 | ‡ | ‡ | 40 | 10 | 8 | ‡ | ** | 40 | 10 | 8 | ‡ | ‡ | 70 | 20 | 8 | ‡ | ** |
| Uninfected | 20 | 24 | 10 | NA | * | 412 | 14 | 7 | NA | ** | 508 | 11 | 8 | NA | * | 295 | 15 | 8 | NA | ** |

¶virus inoculated into E7 embryos
#populations immunostained and analysed by FACS
μ mean
SEM standard error of the mean
n sample size
$P_1$ P value for t-test between uninfected and treatment group
$P_2$ P value for t-test between CAU269/7 and treatment group
* P value significant at 0.05 level
** P value significant at 0.01 level
*** P value significant at 0.001 level
‡ P value not significant at 0.05 level

TABLE 17

B lymphocyte populations from the thymus, spleen and bursa of E21 embryos infected with wild type and VP2 mutant CAU269/7.

| Treatment | Mean Av Bu1+ lymphocyte populations (×10$^6$)# | | | | | | | | | | | | | | |
|---|---|---|---|---|---|---|---|---|---|---|---|---|---|---|---|
| | Thymus | | | | | Spleen | | | | | Bursa | | | | |
| group¶ | μ | SEM | n | $P_1$ | $P_2$ | μ | SEM | n | $P_1$ | $P_2$ | μ | SEM | n | $P_1$ | $P_2$ |
| CAU269/7 | 44 | 20 | 3 | * | NA | 9.5 | 0.3 | 3 | *** | NA | 0.7 | 0.3 | 3 | * | NA |
| Mut C87R | 213 | 40 | 9 | ‡ | * | 2.5 | 0.5 | 9 | ‡ | ** | 2.9 | 0.7 | 9 | ‡ | ** |
| Mut R101G | 120 | 39 | 7 | ‡ | ‡ | 8.3 | 0.3 | 7 | ‡ | ‡ | 53 | 1.8 | 7 | ‡ | * |
| Mut H103Y | 77 | 16 | 9 | ‡ | ‡ | 7.7 | 1.4 | 9 | ‡ | ‡ | 45 | 2.4 | 9 | ‡ | ‡ |
| Mut R129G | 116 | 45 | 8 | ‡ | ‡ | 2.9 | 1.5 | 8 | ‡ | ‡ | 24 | 1.2 | 8 | ‡ | ‡ |
| Mut R/K/K150/151/152G/A/A | 556 | 219 | 5 | ‡ | * | 14 | 3.4 | 5 | ‡ | * | 45 | 7.3 | 5 | * | ** |
| Mut D/E161/162G/G | 198 | 155 | 5 | ‡ | ‡ | 24 | 0.9 | 5 | ‡ | * | 17 | 1 | 5 | ‡ | ‡ |
| Mut L163P | 191 | 92 | 8 | ‡ | ‡ | 6.4 | 0.2 | 8 | ‡ | ‡ | 13 | 0.6 | 8 | ‡ | * |
| Mut D169G | 103 | 32 | 9 | ‡ | * | 19 | 0.8 | 9 | ‡ | ‡ | 64 | 2.5 | 9 | ‡ | ‡ |
| Mut E186G | 118 | 13 | 10 | ‡ | ** | 3.3 | 0.8 | 10 | *** | *** | 8.9 | 0 | 8 | * | * |
| Uninfected | 119 | 76 | 2 | NA | * | 6.5 | 0.3 | 2 | NA | *** | 29 | 1.9 | 2 | NA | * |

¶virus inoculated into E7 embryos
#populations immunostained and analysed by FACS
μ mean
SEM standard error of the mean
n sample size
$P_1$ P value for t-test between uninfected and treatment
$P_2$ P value for t-test between CAU269/7 and treatment
* P value significant at 0.05 level
** P value significant at 0.01 level
*** P value significant at 0.001 level
‡ P value not significant at 0.05 level II. Mutation of the Translational Initiation Signals of CAV VP2

Construction of CAV Genomes Containing Mutations About the VP2 ATG Codon

All CAV DNA sequences were originally derived from plasmid pCAU269/7. Overlapping PCR extension was used to generate DNA sequences containing the desired nucleotide changes. An ApaI/BstBI DNA fragment of CAV genome was amplified by means of PCR using synthetic oligonucleotide pairs (CAV1/CAV20, CAV19/CAV11, CAV1/CAV22, CAV21/CAV11), see Table 18.

DNA Preparation and Transfection

Viral DNAs were prepared for transfection by digesting 10 μg of endotoxin-free plasmid DNA, purified by Triton X-100, with EcoRI to release the CAV genome insert. Restriction products were extracted with phenol-chloroform, ethanol precipitated and resuspended at a concentration of 1 μg/μL. Aliquots were examined by agarose gel electrophoresis to verify release of insert and efficiency of recovery.

MSB1 cells were washed 3 times and resuspended in warmed RPM1-1640 without supplements to a final concentration of $4\times10^6$ in 700 μL. Cells were transfected by electroporation in 0.4 cm-gap cuvettes (BioRad) at 400V and 375 μF. Pulsed cells were incubated at room temperature (RT) for 5 mins before being transferred to 6-well tissue culture trays containing 3 mL of prewarmed RF10 and incubated at 37° C. in 5% $CO_2$. Transfection efficiency (CMV-GFP expression—pEGFPC2, Clonetech) in control wells was estimated 24 hours post transfection. The transfected cells were observed for cytopathic effect (cpe) and sampled for expression of VP3 as determined by fluorescence staining.

TABLE 18

PCR primers.

| Oligo-nucleotide | Sequence (5'-3') | Context | Coding change |
|---|---|---|---|
| CAV 19 | cggtccgggg**A**ggatgcacggaaacgg (SEQ ID NO: 58) | -3 position -> A | No aa change |
| CAV 20 | gtgcatcc**T**cccgaccgccttgcgt (SEQ ID NO: 59) | -3 position -> A | No aa change |
| CAV 21 | cggtccgggtggatg**G**acggaaacgg (SEQ ID NO: 60) | +4 position -> G | His->Arg in VP2 (aa#2) |
| CAV 22 | gt**C**catccacccggaccgccttgcgt (SEQ ID NO: 61) | +4 position -> G | His->Arg in VP2 (aa#2) |
| CAV 1 | ctatcgaattccgagtggttactat (SEQ ID NO: 62) | Forward | N/A |
| CAV 11 | agctcgtcttgccatcttacagtcttatac (SEQ ID NO: 63) | Reverse | N/A |

N/A—not applicable

Oligonucleotide pairs, CAV1/CAV20, CAV19/CAV11, CAV1/CAV22 and CAV21/CAV11 containing desired nucleotide changes, were used in separate $1^{st}$ round PCR amplifications (25 cycles) to generate products of 347 bp, 495 bp, 347 bp and 495 bp, respectively. Products were analysed by gel electrophoresis to verify size and quantity and subsequently diluted to 25 ng/μL before being used (either the CAV1/CAV20 product with the CAV19/CAV11 product, or the CAV1/CAV21 product with the CAV22/CAV11 product) to seed two $2^{nd}$ round PCR amplifications (20 cycles) in which only oligonucleotide pair CAV1/CAV11 was utilised. The products generated from this overlapping extension PCR were identical to fragment CAV1/CAV11 except for the incorporation of the desired nucleotide changes (either the replacement of a T with and A in the −3 position for pCAU283-3, or the replacement of a C with a G in the +4 position for pCAU283+4) about the VP2 ATG codon. The overlapping extension products were digested with ApaI/BstBI and 153 bp fragments spanning the VP2 ATG codon were isolated and ligated separately with plasmid pCAU269/7 digested with the same enzymes. The resulting constructs were designated pCAU283-3 and pCAU283+4 and were analysed by restriction enzyme digestions and sequencing to confirm the newly introduced sequences.

Sequence Analysis

DNA sequences were determined by the dideoxy chain termination method using BigDye Terminator sequencing chemistry (ABI Prism) with combination of vector specific (T7 and SP6) and CAV sequence specific synthetic primers (CAV 12, 2, 10, 3, 9, 4, 7, 5).

Indirect Immunofluorescence Assay

Cells were washed twice and resuspended in phosphate-buffered-saline and plated at approximately 30-50,000 cells/well on 12-well slides, air dried and fixed with ice-cold acetone:methanol (90:10). Slides were blocked with 5% BSA in PBS/0.05% Tween 20 before reacting them with the mouse derived CAV VP3-specific monoclonal antibody JCU/CAV/1C1 (JCU TropBio, Townsville, Queensland) for 60 mins in a humidi-chamber at 37° C., and fluoroscein isothiocyanate-conjugated rabbit anti-mouse immunoglobulin G antibody under the same conditions. Following a third wash, slides were mounted with VectaShield and viewed by fluorescence microscopy.

Results

Construction of CAV Genomes Containing Mutations Around the VP2 ATG Codon

Plasmid pCAU269/7 can be used for the production of viable infectious CAV particles. In this study, the present inventors examined whether the mutated CAV-DNA genomes, pCAU283-3 and pCAU283+4, could also produce replication-efficient virus. To that end, MDCC-MSB1 cells were transfected with these modified CAV genomes in parallel with wt CAV DNA (pCAU269/7).

Analysis of Differences in the Replication Rate of Mutated CAV Versus wt CAV

In establishing the replication competency of the mutated genomes, the synthesis of the CAV protein VP3 was tracked in transfected MDCC-MSB1 cells. At 40 hours post transfection, a sample of the transfected cultures was analysed by indirect immunofluorescence with mAB JCU/CAV/1C1 against VP3. In parallel, samples of transfected cultures were passaged (1:10) into fresh culture medium.

The transfected CAV mutants showed a similar percentage of cells expressing VP3 as wild type (wt) CAV genome 40 hours following transfection. In VP3-expressing cells, cytopathic effects observed were characterised by the appearance of enlarged, misshapen cells and were consistent with that of other reported CAV isolates. Total cell degeneration of these cells was apparent within 96 hours of infection.

There was no apparent difference in cellular localisation or fluorescence intensity of VP3 staining in the wt or mutant genomes, as determined by fluorescence microscopy. At several time points after transfection, further samples of passaged transfected cultures were examined for the production of viable infectious CAV particles. Within six days, no VP3-positive cells could be found in MDCC-MSB1 cultures transfected with mutant genomes pCAU283-3 or pCAU283+4. Furthermore, medium taken from cultures transfected with these genomes did not produce cytopathic effects when passaged onto fresh MDCC-MSB1 cells.

These results suggest that the mutant DNAs exhibit severely reduced cytopathogenicity in MDCC-MSB1 cells relative to wt pCAU269/7 and only transiently express CAV proteins following transfection. Such mutant virus genomes can be used for DNA vaccination in chickens as they will not result in the generation of replicative virus, but will be able to transiently express viral proteins.

III. Viral Protein 2

Viral protein 2 (VP2) of the immunosuppressive circovirus Chicken Anaemia Virus (CAV) has been shown to be essential to viral infectivity and replication, however its function has not yet been established. The CAV VP2 amino acid sequence has significant homology to a number of eukaryotic receptor, protein-tyrosine phosphatase alpha proteins, as well as to a cluster of TT viruses within the SANBAN group. The ORF encoding VP2 was amplified by PCR and cloned into the bacterial expression vector pGEX4T-2. VP2-GST fusion protein was expressed and purified by affinity chromatography. Purified VP2-GST was assayed for protein tyrosine phosphatase (PTPase) activity using the generalised peptide substrate ENDY(Pi)INASL (SEQ ID NO: 71), with free phosphate detected using the malachite green colorimetric assay. VP2-GST exhibited protein tyrosine phosphatase activity with a $V_{max}$ of 14 280 U/mg.min and a $K_m$ of 16.95 μM. Optimal activity was observed at pH 6-7 and activity was specifically inhibited by 0.01 mM orthovanadate. A unique signature motif is proposed for CAV VP2 PTP: ICNCGQFRK (SEQ ID NO: 64) encoded by amino acid residues 94 to 102.

Experimental Procedures—VP2

Sequence Analysis

Protein sequences with homology to CAV VP2 were identified by searches of the Genbank database using the BLASTX software (Basic Local Alignment Search Tool) via the NCBI interface. Sequences identified by this method were then aligned to the CAV sequence using EclustalW (WebANGIS, Australian National Genomic Information Service).

Molecular Cloning of CAV viral protein 2 and TLMV ORF2

The CAU269/7 Australian isolate of CAV was used in all experiments. CAV ORF1 (VP2) was amplified by polymerase chain reaction (PCR) from the double stranded replicative form of the CAV genome. A cellular DNA preparation was purified from CAV infected MDCC-MSB 1 cells 48 h after infection by proteinase K and sodium dodecyl sulphate (SDS) lysis and phenol/chloroform extraction, using the method of Meehan, B. M., Todd, D., Creelan, J. L., Earle, J. A., Hoey, E.M. and McNulty, M. S. (1992). Characterization of viral DNAs from cells infected with chicken anaemia agent: sequence analysis of the cloned replicative form and transfection capabilities of cloned genome fragments. *Arch Virol* 124, 301-3 19. Oligonucleotide forward primer CAV.1 5' CGGTCCGGATCCATGCACGGAAACGGCGGACAAC 3' (SEO ID NO: 65) and reverse primer CAV.2 -5' GGTTTGGAATTCTCACACTATACGTACCGGGGC 3' (SEQ ID NO: 66) were synthesised to incorporate BamHI and EcoRI restriction endonuclease sites within the respective 5' ends. A 100 1μL reaction mixture was prepared containing 300 μM each of dATP, dCTP, dGTP and dTTP, 2 mM $MgCI_2$, 200 μM of each primer, 10 μL of 10×Taq DNA polymerase buffer, 2 U of Taq DNA polymerase (Promega), and 2 μL of template DNA. The PCR reaction was incubated at 95° C. for 2 min, followed by 40 cycles at 96° C. for 40 s, 60° C. for 40 s and 72° C. for 40 s, with a final incubation at 72° C. for 5 min. The PCR products were analysed by agarose (1%) gel electrophoresis and a band of 677 bp was excised and purified using a Qiaex II (Qiagen) gel extraction kit according to the manufacturer's instructions, digested with BamHI and EcoRI and ligated to appropriately digested pGEX-4T-2 (Promega). The *E. coli* strain DH5α was transformed by electroporation with the ligated plasmid and cultured at 37° C. on Luria-Bertani agar (LA) containing ampicillin at 50 μg/mL. The cloned DNA was sequenced using a Taq Dye Deoxy Terminator Cycle Sequencing kit (Perkin Elmer) using commercial sequencing primers specific for PGEX-4T-2.

Purified nested PCR product from primers M-1360 to M-1363 (258 bp-886 bp) of TLMV strain CBD231 was kindly supplied by Shunji Mishiro (Takahashi et al, 2000). TLMV ORF2 was amplified by PCR from the M-1360 to M-1363 template. Oligonucleotide forward primer TLMV.1 -5' TTGGATCCATGAGCAGCTTTCTAACACCATC 3' (SEQ ID NO: 67) and reverse primer TLMV.2 -5' GGCGAATTCTTACCCATCGTCTTCTTCGAAATC 3' (SEO ID NO: 68) were synthesised to incorporate unique BamHI and EcoRI restriction enzyme sites within the 5' ends respectively. A 50 μL reaction mixture was prepared containing 300 μM each of dATP, dCTP, dGTP and dTTP, 2 mM $MgCI_2$, 200 μM of each primer, 5 μL of 10×Taq DNA polymerase buffer, 1 U of Taq DNA polymerase (Promega), and 1 μL of template DNA. The PCR reaction was incubated at 96° C. for 2 min, followed by 40 cycles at 96° C. for 40 s, 56° C. for 40 s, then 72° C. for 40 s, and a final incubation at 72° C. for 5 min. Purification, digestion and cloning of the 295bp PCR product into the pGEM-T plasmid vector (Promega) proceeded as described above for CAV viral protein 2. The insert was subsequently subcloned into the pGEX-4T-2 plasmid vector and the sequence and frame of the insert was verified by sequencing.

Protein Expression and Purification

CAV VP2 was produced as a C-terminal fusion with glutathione S-transferase. Briefly, 1 L cultures of *E. coli* DH5α possessing the CAV VP2 pGEX-4T-2 construct were cultured in Luria-Bertani broth containing ampicillin at 50 μg/mL. Expression was induced by adding isopropyl-β-D-thiogalactopyranoside (IPTG) to a final concentration of 1 mM when the culture reached an optical density of 0.6 at 600 nm, and the culture incubated an additional hour prior to harvest. Bacteria were recovered by centrifugation at 6000 g for 30 min and the pellets washed twice in phosphate buffered saline (PBS). The cells were resuspended in 25 mL of PBS containing 0.3 M EDTA, 200 mg lysozyme, and 100 μg of phenyl methyl sulfonyl fluoride (Sigma)/mL and lysed by 10 second bursts of sonication at low frequency. The lysate was solubilised in 0.1% Triton X-100, incubated a further 10 min at 4° C., and the cellular debris removed by centrifugation at 10 000 g for 30 min. The fusion protein was affinity purified using glutathione sepharose resin (Promega) following the manufacturer's protocol. The eluate was extensively dialysed against a buffer containing 137 mM NaCl, 2.7 mM KCl and 25 mM Tris HCl (TBS) pH 7.4.

Negative control glutathione-S-transferase was purified from *E. coli* DH5α transformed with pGEX-4T-2 following the same method as was used to purify the GST-VP2 fusion.

Purified protein was separated by electrophoresis in 12.5% SDS-polyacrylamide gels and stained with Coomassie brilliant blue (Laemmli, U. K. (1970). Cleavage of structural proteins during the assembly of the head of bacteriophage T4. *Nature* 227, 680-685). Proteins were electrotransferred to a polyvinyldifluoride membrane (PVDF: Immobilon Millipore); Western blots of GST-VP2 and GST were probed with rabbit polyclonal antiserum raised against GST, at a dilution of 1/500, followed by a secondary swine anti-rabbit HRP conjugate (Dako) diluted 1/1000, and developed with Sigma Fast 3,3'-diaminobenzidine substrate (DAB, Sigma) according to the manufacturer's instructions. A second western blot was probed with pooled immune chicken serum, followed by rabbit anti-chicken-HRP conjugate at a dilution of 1/500, and developed with DAB substrate. Protein concentration was quantified using the Bradford Assay (BioRad) with a bovine serum albumin (BSA) (Sigma) standard.

TLMV ORF2 was purified from *E. coli* DH5α transformed with the TLMV ORF2 pGEX 4T-2 clone following the same method as was used to purify the GST-VP2 fusion. However protein expression was induced for only 30 min.

Synthesis of Peptide Substrate

The generalised protein tyrosine phosphatase substrate described by Daum, G., Solca, F., Diltz, C. D., Zhao, Z., Cool, D. E. and Fischer, E. H. (1993). A general peptide substrate for protein tyrosine phosphatases. *Anal Biochem* 211, 50-54, was used in all enzyme assays. The phosphopeptide sequence was H-Glu-Asn-Asp-Tyr($PO_3H_2$)-Ile-Asn-Ala-Ser-Leu-OH (SEQ ID NO: 71). Briefly, the nonapeptide was assembled manually in the solid phase using Fmoc chemistry. All chemicals for use in peptide synthesis were of analytical grade. Fluorenylmethoxycarbonyl (Fmoc) protected amino acid residues (Auspep, Melbourne, Australia) were used for synthesis. The residues used were Fmoc-L-Leu-OH, Fmoc-L-Ser(tBu)-OH, Fmoc-L-Ala-OH, Fmoc-L-Asn(Trt)-OH, Fmoc-L-Ile-OH, Fmoc-L-Tyr(MDSPE), Fmoc-L-Asp (OtBu)-OH, Fmoc-L-Asn(Trt)-OH and Fmoc-L-Glu(OtBu)-OH. The support resin PAC-PEG-PS (Perspective Biosystems, capacity 0.18 mmol/g) was used for the synthesis. The amino acids were activated by incubation with equimolar quantities of O-benzotriazole-N,N,N',N'-tetra methyl-uronium-hexafluorophosphate (HBTU)) (Auspep) and 1-hydroxybenzotriazole (HOBt) (Auspep) and two equivalents of diisopropylethylamine (DIPEA) (Auspep). The coupling reaction was carried out for 60 min followed by the trinitrobenezene sulfonic acid test. The Fmoc groups were removed after each coupling reaction by washing in 2.5% 1,8-diazabicyclo-[5.4.0]undec-7-ene (DBU). For the coupling of residues 4 to 9 each cycle was repeated twice. The side chain protective groups were removed and the peptide was cleaved from the resin by treatment with 88% trifluoroacetic acid (TFA), 5% phenol and 2% tri-isopropylsilane (Aldrich, Milwauke, Wis.) in water. The crude peptide was precipitated in cold diethyl ether prior to purification by reverse-phase High Performance Liquid Chromatography (RP-HPLC) over a Vydac C4 semipreparative column in 0.1% trifluoroacetic acid and eluted with a 2%/min gradient of acetonitrile. The identity of the peptide was confirmed by mass spectroscopy.

Protein Tyrosine Phosphatase Assay

All protein tyrosine phosphatase reactions were adapted from the method of Tonks, N K., diltz, C D. and Fischer, E. H (1991). Purification and assay of CD45: an integral membrane protein-tyrosine phosphatase. *Methods Enzymol* 201, 442-451. The following reaction conditions apply for all assays unless otherwise stated. An assay buffer (AB) was prepared with 50 mM Tris (pH 7 at 25° C.), 1 mM EDTA, 50 mM 2-mercaptoethanol and 1% (w/v) BSA. A second buffer (TB) was prepared with 50 mM Tris (pH 7 at 25° C.) and 0.01% w/v Brij 35 (Sigma). All reactions were carried out in 200 μl volumes in a microtitre plate. A 1 mM solution of phosphopeptide substrate was made in AB buffer. Fifteen nanomoles of substrate was added to each of 14 triplicate reaction mixtures of 1:1 AB and TB buffers. The reactions were started by the addition of 9 μg of either VP2-GST or GST. Reactions were incubated with shaking at room temperature for 0, 1, 2, 3, 4, 5 or 10 minutes, and terminated by the addition of malachite green reagent. All assays were repeated on at least three occasions and the average activity was plotted for each time point. Activity was adjusted by a factor of 0.52 to account for the contribution to mass of the 24 kDa GST fusion tag and expressed as nmol of catalysed substrate per microgram of enzyme.

Malachite Green Detection of Soluble Phosphate

The release of free phosphate into solution was detected by the malachite green colorimetric assay. Briefly, stock malachite green solution was made by the slow addition of 60 mL of concentrated sulfuric acid to 300 mL of water followed by cooling to room temperature, and then 0.44 g of malachite green (Fisher Scientific) was added. Immediately before use the colorimetric reagent was made from 10 mL of stock malachite green, 3% (w/v) $(NH_4)_3MoO_3$ (Sigma) and 0.15% Tween 20 (Sigma).

Fifty microlitres of the colorimetric reagent was added to the 200 μl reaction volume in a microtitre plate and allowed to equilibrate for 20 minutes at room temperature. Absorbance was read at 620 nm and phosphate release was calibrated against a phosphate standard curve.

A phosphate standard curve was prepared for phosphate values of 0, 2.5, 5, 7.5, 10, 15, 20, 25, 30, 40 and 45 nmol. Phosphate solutions were prepared in buffer at a 1:1 ratio of AB and TB buffer, and 200 μl added to each of three wells in a microtitre plate. For each concentration 50 μl of the colorimetric reagent was added and allowed to equilibrate for 20 minutes at room temperature. Absorbance was then measured at 620 nm.

Enzyme Kinetic and Inhibition Studies

Substrate was added to triplicate reaction mixtures at 0, 2.5, 5, 7.5, 10, 15, 20, 25, 30 and 40 nmol. Incubations were for 1 min, and all other reaction conditions were as described above. For each substrate concentration activity was measured in at least 6 replicate reactions and the standard error of the mean activity calculated for each value. $V_{max}$ and $K_m$ estimates were derived by linear regression analysis from a double reciprocal plot and the standard error and P-value calculated for the constant $1/V_{max}$ and the coefficient $K_m/V_{max}$ from the plot.

Stock 1 mM $Na_3VO_3.10H_2O$ was made in distilled water and adjusted to pH 10 with sulphuric acid. Once dissolved, stock $Na_3VO_3.10H_2O$ was added to AB and TB buffer at a ratio of 1:1:1 and adjusted to pH 7. Inhibition studies were conducted with 0.1 mM, 0.01 mM and 0.001 mM of sodium orthovanadate. All other reaction conditions were as described above. Assays were with 10 nmol substrate and 9 μg CAV VP2-GST and were in triplicate for each concentration of inhibitor.

Enzyme pH Optimum

Triplicate reactions were set up at pH 4, pH 5, pH 6, pH 7, pH 8 and pH 9. Assays were with 10 nmol substrate and 9 μg CAV VP2-GST and all other reaction conditions were as described above. Prior to addition of the malachite green reagent the pH was neutralised to pH 7 with either sulphuric acid or sodium hydroxide.

TLMV VP2 GST Fusion Assay

The TLMV-GST protein was assayed following the reaction conditions described for CAV VP2. Reactions were repeated 4 times.

Results—VP2

Sequence Analysis

Figure 13:
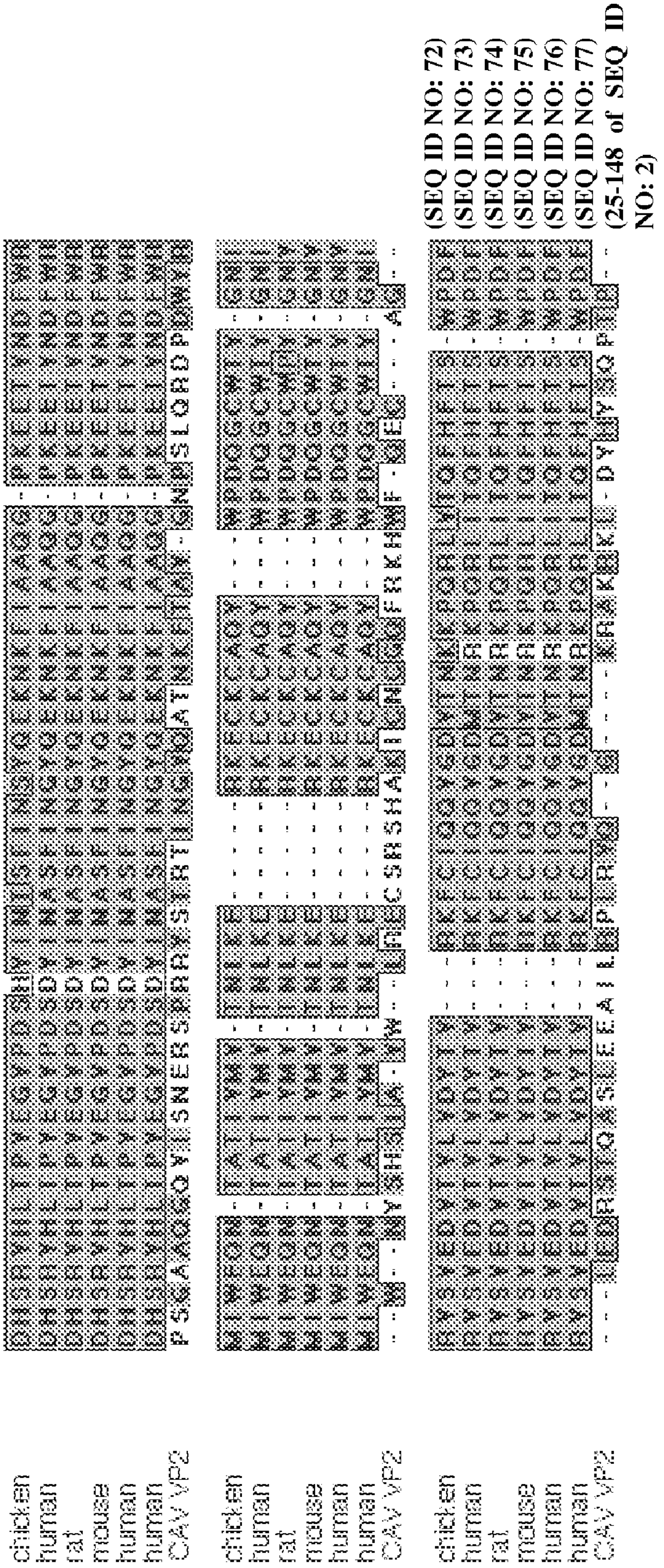
FIG. 13 shows R-PTPase homologues aligned to the CAV VP2 amino acid sequence using the ECLUSTALW software (WebANGIS) and displayed graphically using the Seqvu software (Garvin Institute). Row 1 (SEQ ID NO: 72): chicken protein-tyrosine phosphatase alpha (Z32749), residues 302-306, homology score 30%. Row 2 (SEQ ID NO: 73): human R-PTPase alpha (PP18433), residues 301-353, homology score 32%. Row 3 (SEQ ID NO: 74): rat R-PTPase alpha (Q03348), residues 295-347, homology score 32%. Row 4 (SEQ ID NO: 75): mouse R-PTPase alpha (P18052), residues 328-380, homology score 32%. Row 5 (SEQ ID NO: 76): human R-PTPase alpha (17011300A). Row 6 (SEQ ID NO: 77): human placental protein-tyrosine phosphatase (CAA38065), residues 292-345, homology score 32%. Row 7 (residues 25-148 of SEQ ID NO: 2): CAV VP2.

A database search for protein sequences with homology to CAV VP2 identified a number of receptor protein tyrosine phosphatase alpha (R-PTPase) proteins of human, rat, mouse and chicken origin. CAV VP2 homology was to the WPD loop flanking the P-loop in all R-PTPase homologues. The WPD loop is involved in PTPase activity. The P-loop contains the catalytic site and signature motif. Similarity between CAV VP2 and the R-PTPase homologues was in the range of 30-32%. The R-PTPase homologues and CAV VP2 amino acid sequences have been aligned in FIG. 13.

Figure 14:
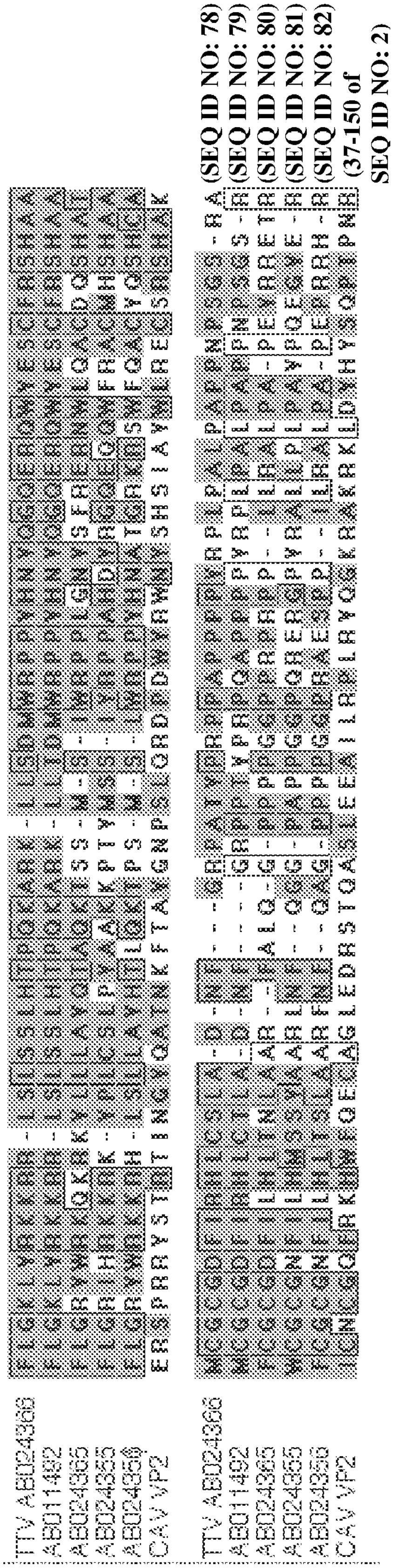
FIG. 14 shows alignment of CAV VP2 amino acid sequence and SANBAN TTV sequence using the ECLUSTALW software (WebANGIS) and displayed graphically using the Seqvu software (Garvin Institute). The Genbank accession numbers for the TT viruses are shown. Rows 1-6 disclose SEQ ID NOS 78-82 and residues 37-150 of SEQ ID NO: 2, respectively in order of appearance).

A second cluster of sequences was identified from the Genbank database as highly homologous to CAV VP2. The SANBAN group of TT viruses possess significant homology to CAV VP2. In all SANBAN viral sequences, the region of homology extends from residues 54-80 of the amino acid sequence encoded by the putative ORF1. Homology was to the same region of the protein as for the PTPase homologues, however, the pattern of homologous residues varied. Homology between CAV VP2 and the SANBAN viral sequences was 48%. The alignment of CAV VP2 sequence with SANBAN viruses is illustrated in FIG. 14.

Protein Expression and Purification

CAV ORF1 was amplified from the CAU269/7 Australian isolate of CAV. The CAU269/7 isolate was equivalent in pathogenicity and infectivity to other described isolates of CAV. The PCR product was cloned into the pGEX 4T-2 vector and CAV VP2 protein was produced as a recombinant fusion protein with glutathione-S-transferase in a bacterial expression system. The size and identity of the protein was verified by electrophoresis in 12.5% SDS PAGE, followed by Coomassie brilliant blue staining and Western blotting (FIGS. 15 to 17). A band of 58 kDa molecular weight corresponding to the CAV VP2-GST fusion protein was identified by SDS-PAGE from affinity purified eluate. The protein band reacted specifically with antiserum raised against the GST tag and also with pooled hyperimmune chicken serum. The dialysed protein was readily soluble in TBS buffer and was used directly in PTPase assays. Protein concentration was determined by the Bradford assay against a BSA standard curve.

Synthesis of Peptide Substrate

Peptide substrate was synthesised on a solid support using standard Fmoc chemistry. Following the addition of the phosphotyrosine residue, all subsequent cycles were duplicated to counter potential steric hindrance to coupling by the large phosphate group. A single peak consistent with pure phosphopeptide was seen on analytical RP-HPLC, and the formula weight was confirmed as 1116.3 by mass spectroscopy.

Protein Tyrosine Phosphatase Assays

A standard curve of absorbance at 620 nm as a function of phosphate concentration was established for the assay conditions. The sensitivity of the malachite green calorimetric detection was 2.5 nmol phosphate and the relationship between log[Pi] and absorbance at 620 nm was linear over the range of 0 to 45 nmol of phosphate. Concentrations of phosphate greater than 45 nmol resulted in a phosphomolybdate precipitation thereby eliminating the linearity of the relationship.

VP2-GST fusion protein was clearly shown to have protein tyrosine phosphatase activity. The time course for phosphate release by CAV VP2-GST relative to control GST protein is shown in FIG. 18. Based on the linear region of the curve from the time course study, in all subsequent reactions $V_o$ was measured at 1 min. VP2-GST displayed Michaelis-Mentin kinetics and the relationship between $V_o$ and [S] was $1/[V_o]=(1.292).1/[S]+0.060$. The plots of activity of VP2-GST and GST control proteins are illustrated in FIG. 19. The Lineweaver-Burk double reciprocal plot for VP2-GST is shown in FIG. 20. From the Lineweaver-Burk plot, $1/V_{max}$ was found by linear regression to be 0.060 (standard deviation=0.0137, P<0.0001) and $K_m/V_{max}$ was found to be 1.292 (standard deviation=0.1085, P<0.0001). Based on these results, $V_{max}$ was estimated to be 14 280 U/mg min and $K_m$ to be 16.95 μM. All assays were repeated three times using 2 different preparations of VP2-GST protein and each substrate concentration was repeated at least 4 times.

Effect of Reaction pH and Orthovanadate Inhibition on Tyrosine Phosphatase Activity Protein tyrosine phosphatase activity was measured at varying reaction pH (Table 19). The optimal VP2-GST PTPase activity was found to be in the range of pH 6-pH 7.

The inhibitory effect of sodium orthovanadate on VP2-GST PTPase activity is shown in Table 20. Orthovanadate concentrations of 0.001, 0.01 and 0.1 mM completely inhibited PTPase activity by VP2-GST.

TABLE 19

Effect of reaction pH on CAV VP2-GST PTPase activity.

| pH | S (nmol) | mean $V_o$ (nmol) | SD |
|---|---|---|---|
| 4 | 10 | 1.746 | 0.007 |
| 5 | 10 | 1.474 | 0.018 |
| 6 | 10 | 5.636 | 0.156 |
| 7 | 10 | 5.612 | 0.041 |
| 8 | 10 | 1.829 | 0.049 |
| 9 | 10 | 0.000 | 0.000 |

TABLE 20

| The effect of sodium orthovanadate inhibition on the kinetics of VP2-GST PTPase activity. | | |
|---|---|---|
| [orthovanadate] mMol | [S] nmol | Vo |
| — | 10 | 5.612 |
| 0.001 | 10 | 0.002 |
| 0.01 | 10 | 0.000 |
| 0.1 | 10 | 0.000 |

PTPase Activity of TLMV ORF2 Product

PTPase activity was demonstrated for TLMV ORF2-GST fusion protein relative to a control CAV VP2-GST assay. The steady state activity was equivalent to that demonstrated for CAV VP2 (FIG. 20).

III. VP2

One aim of this study was to investigate whether CAV VP2 was a novel viral PTPase. This investigation primarily stemmed from the finding of homology between CAV VP2 and a number of PTPases, and the proposal of a PTPase signature motif within the VP2 sequence. PTPases are characterised by the minimal PTPASE signature motif CXXXXXR and by the catalysis of dephosphorylation using a cysteinyl-phosphate enzyme intermediate. The surrounding domains of the protein are involved in the regulation of enzyme activity and in substrate specificity. The profile of VP2 as a non-structural protein, expresses at very low levels but essential to infectivity, and a highly conserved protein between CAV and TT viruses, is consistent with an essential regulatory protein such as a PTPase.

This work is the first to define a function for VP2, and has established that VP2 is a Novel PTPase. These enzymes (PTPases) are defined by their capacity to remove Phosphate specifically from phosphotyrosine residues in phosphoprotein substrates. PTPases have been found to vary in their specific activity for different complex protein substrates. The generalised peptide substrate ENDY(Pi)INASL (SEQ ID NO: 71) used in these assays has been previously described. A wide range of PTPases utilise this substrate allowing comparison of kinetic parameters. The time course and kinetic studies clearly demonstrate that CAV VP2 has protein tyrosine phosphatase activity. A number of other descriptive features have been defined for the PTPase family. As a family, these enzymes are resistant to inhibition of activity by EDTA and display a neutral pH optimum within the range of pH 5.5-7. Studies with CAV VP2 found that the inclusion of EDTA in the assay buffer was essential to activity, and the activity was optimal for pH 6-7. These results are consistent with those described for the family as a whole.

PTPases catalyse the removal of phosphate from phosphotyrosine via a cysteinyl-phosphate intermediate formed with the active cysteine in the catalytic cleft. The mechanism of catalysis is unique to the PTPase family, as is inhibition of activity by low concentrations of orthovanadate. The compound orthovanadate is a structural analogue of phosphate and as such competitively inhibits the cysteinyl-phosphate intermediate. Members of the PTPase family have been shown to vary in the concentration of orthovanadate required for inhibition. CAV VP2 activity was maximally inhibited by orthovanadate concentrations as low as 0.001 mM.

Under the assay conditions described, CAV VP2 had a $V_{max}$ of 14 280 U/mg.min and a $K_m$ of 16.95 μM. CAV VP2 activity is intermediate between that characteristic of high and low molecular mass (Mr) PTPases. The low Mr PTPases tend to have high specific activity. An example is PTP1B which has a $V_{max}$ of 20 000 U/mg min. The high Mr PTPs have lower specific activities in general, although the activity is dependent on substrate specificities. For example CD45 from human spleen has a $V_{max}$ of 1 000 U/mg.min.

The crystallographic structure and catalytic mechanisms of some protein tyrosine phosphatases (PTPases) have been studied in detail. From the studies of high Mr PTPases the consensus signature motif has been defined as (I/V)HCXAGXGR(S/T)(SEQ ID NO: 69). The cysteine residue is critical in binding the phosphate and the arginine coordinates the phosphotyrosine in the catalytic cleft. A minimal signature motif has been defined for the PTPase superfamily as CXXXXXR. This definition is based on a subgroup of low Mr PTPs that lack overall sequence homology to the conserved PTPase domain but contain this minimal signature motif. The low Mr PTPs are also characterised by activity over a wide range of pH. The proposed catalytic motif in CAV VP2 is ICNCGQFRK (SEQ ID NO: 64), encoded by amino acid residues 94 to 102. The proposed CAV VP2 signature motif diverges from the highly conserved consensus motif seen in high Mr PTPases. However, CAV VP2 has sequence homology to the high Mr PTPases over an extended region that is not seen for the low Mr PTPs. In addition kinetic properties such as pH optimum are characteristic of the subgroup of high Mr PTPs.

Database homology searches identified a number of eukaryotic receptor PTPases (R-PTPases) with identity scores of 30-32% to CAV VP2 over an extended region of approximately 53 amino acids, including the proposed signature motif This group of R-PTPases have significant homology to each other. Paradoxically, the sequence homology between CAV VP2 and the eukaryotic PTPases is to a region upstream from the defined catalytic motif of the eukaryotic proteins. The protein domains of eukaryotic PTPases have been shown to be modular in organisation, and in many PTPases two tandem conserved catalytic domains have been identified, only one of which is functional. The significant homology between the active VP2 catalytic fold and the protein fold flanking the eukaryotic motif of identical function may indicate functional redundancy in the eukaryotic proteins. Redundancy within PTPases may exist not only as entire domains as previously understood, but also at the level of secondary structure within protein folds.

Of additional interest is the finding of significant homology over the same region Between CAV VP2 and the SANBAN subgroup of TT viruses. TT viruses have recently been identified from human hosts as a heterogeneous cluster of single stranded, negative-sense, circular DNA viruses. Sequence analysis of this group of viruses has demonstrated greatest overall homology to CAV. The highest sequence homology to CAV is seen in the non-coding region and between ORF2 of TTV viruses and CAV VP2. All TTV, SANBAN, YONBAN and TLMV viruses (TTV Like Mini Viruses) have in common with CAV the sequence $WX_7HX_3CXCX_5H$ (SEQ ID NO: 70) in ORF2. This homologous sequence corresponds to the 5' end of the predicted PTPase signature motif. However the homology between the SANBAN isolates and CAV VP2 is more extensive and includes the entire sequence of the proposed signature motif. Others have recently proposed the classification of the TTV, SANBAN, YONBAN, TLMV and CAV viruses as the Paracircoviridae. The current designation of ORFs in TT viruses is based on sequence analysis alone, as these viruses have not yet been grown in culture or the viral protein expression profiles characterised.

The results shown above clearly identify TLMV ORF2 as a second novel viral PTPase. The demonstration of PTPase activity by TLMV ORF2 is indicative of a common viral strategy for infection and replication between CAV and the TT viruses. The finding is consistent with the close similarity found in genome organisation and the sequence homology between TTV and CAV.

Protein tyrosine phosphatases are known to function in the regulation of mitogenesis, gene transcription, signal transduction, cell-cell interactions, cellular differentiation and in cytokine responses of lymphocytes. CAV infection of T-lymphocyte and haemocytoblast populations of chickens up to 21 days of age leads to profound immunosuppression and anaemia. VP2 PTPase activity during infection may represent a virulence mechanism through viral induced regulatory changes in infected lymphocyte populations. All previous accounts of virus encoded regulatory proteins have involved viruses with large genome sizes and extensive coding capacity. It has been suggested that these viruses can maintain cell regulatory proteins in addition to critical viral structural and replicative proteins. This includes the previously described VH1 PTPase from Vaccinia virus. The present finding is therefore unusual in that CAV has an extremely small genome size (2.3 kb) and only three viral proteins expressed from overlapping reading frames. CAV is therefore highly dependent on host function for completion of its replication cycle, and it is possible that a capacity to regulate the lymphocyte cell cycle may be a critical viral function. To the best of our knowledge, CAV VP2 PTPase is only the second viral PTPase to be described, and is the only PTPase described in a virus of this type.

IV. DNA Inoculation of Embryos with Single and Double-Stranded CAV Genome

Introduction

The standard method used for the generation of infectious virus from CAV genome by the transfection of double-stranded DNA into MDCC-MSB1 cells was described by Noteborn, M. H., de Boer, G. F., van Roozelaar, D. J., Karreman, C., Kranenburg, O., Vos, J. G., Jeurissen, S. H., Hoeben, R. C., Zantema, A. and Koch, G. (1991). Characterisation of cloned chicken anemia virus DNA that contains all elements for the infectious replication cycle. *J Virol* 65, 3131-3139. Alternative methodologies for the generation of CAV virions from genome have not been investigated, and there are no published reports of the inoculation of naked genomes of any virus into chick yolk sac. A capacity to generate infectious virus in ovo from naked DNA genome would permit the production of vaccines without an intermediate transfection step in MDCC-MSB1 cells. This methodology would have the potential to enhance biosecurity, as the transformed MDCC-MSB1 cell line contains latent Marek's Disease Virus genome, and cell passage carries the risk of inadvertent contamination of vaccine virus.

Chicken Anaemia Virus, in common with other members of the Circoviridae, has a circular, single-stranded, negative-sense DNA genome enclosed within a non-enveloped caspid. The normal infectious cycle of the virus has been investigated an viral replication proceeds through a double-stranded, replicative intermediate. Double-stranded, replicative forms of 2.3 kbp, 1.3 kbp and 0.8 kbp, and open circular and closed circular forms, have been identified in MDCC-MSB1 cells infected with CAV. The order in which the double-stranded replicative intermediate, the transcript, and the encapsidated single-stranded genome are synthesised, is not known. It has been demonstrated that infectious virus could be readily recovered from MDCC-MSB1 cells transfected with the double-stranded form of the genome alone. Therefore the 2319 bp cloned CAV DNA sequence contains all the genetic information required for the generation of infectious virus within the host-cell. The recovery of replication-competent virus from the transfection of single-stranded DNA genome has not been investigated. For virus replication to proceed from the transfection of single-stranded DNA genome it would require a double-stranded replicative form to be synthesised from cytoplasmic single-stranded genome.

The objective of this study was to investigate whether virus replication can proceed from the transfection of MDCC-MSB1 cells with different CAV genomic constructs. The capacity for viral replication to proceed from either the single-stranded or double-stranded forms of the genome, from either linear or circular forms, and from either positive or negative-sense strands, was investigated. A further objective was to investigate whether virus replication can proceed in vivo after inoculation of these DNA constructs into the yolk sac, and to investigate the relative efficiency of the different genomic constructs, in generating infectious virus after inoculation into the yolk sac.

Bi-Directional Cloning of the CAV Genome into M13.t130 Bacteriophage

In order to obtain positive-sense and negative-sense single-stranded CAV genome, the genome was subcloned from the pGEX-4Z plasmid vector into the M13.t130 bacteriophage. The construction of the pCAU269/7 genomic clone in the pGEX-4Z vector has been described by Brown, H. K., Browning, G. F., Scott, P. C. and Crabb, B. S. (2000). Full-length infectious clone of a pathogenic Australian isolate of chicken anaemia virus. *Aust Vet J* 78, 637-640. The CAU269/7 genome was bidirectionally subcloned from the pGEX-4Z plasmid vector into the M13.t130 bacteriophage. The orientation of the genomic insert within the M13.t130 bacteriophage vector was determined from the analysis of the PstI digestion pattern. Bands of approximately 8.9 kbp and 0.6 kbp were seen after PstI digestion of an M13.t130 clone containing CAV genome inserted with the positive-sense strand oriented 5' to 3' (designated CAV.M13.pos). Bands of approximately 7.8 kbp and 1.8 kbp were seen after PstI digestion of an M13.t130 clone containing CAV genome inserted with the negative sense strand oriented 5' to 3' (designated CAV.M13.neg). The orientation of the CAV genomic sequence in these clones was further confirmed by sequencing in both directions using primers that hybridised to sequences flanking the cloning site.

Transfection of MDCC-MSB1 Cells with CAV Genomic Constructs

The efficacy of virus growth after transfection of different CAV genomic constructs into MDCC-MSB1 was assessed. Single-stranded and double-stranded forms of the CAV genome were prepared. Double-stranded CAV DNA was prepared from a culture of the pCAU26917 plasmid. A band of the correct size from the CAV genome released from the pCAU269/7 clone by EcoRI digestion, was purified by 1% gel electrophoresis and circularised by ligation. Bands of the correct size were purified by 1% gel electrophoresis for single-stranded, CAV DNA prepared from cultures of the bacteriophage clones CAV.M13.pos and CAV.M13.neg. The presence of only single-stranded DNA in the preparation was confirmed by digestion of all DNA by Mung Bean nuclease which specifically digests single-stranded DNA. Primers which hybridised to sequences flanking the cloning sites were annealed to both the single-stranded CAV.M13.pos and CAV.M13.neg preparations, and then digested with EcoRI. The DNA was circularised by ligation, and then quantified by spectroscopy.

The regeneration of virus after transfection with these DNA constructs was assessed by immunofluorescence over sequential cell culture passages, and cell-free virus was prepared from cell lysates. Virus was recovered after transfection with the following genomic DNA constructs:

(i) circularised, positive-sense, single-stranded, CAV DNA, prepared from the CAVM13.pos clone;
(ii) linear, positive-sense, single-stranded, CAV DNA, prepared from the CAVM13.pos clone;
(iii) circularised, negative-sense, single-stranded CAV DNA, prepared from the CAVM13.neg clone;
(iv) linear, negative-sense, single-stranded CAV DNA, prepared from the CAVM13.neg clone; and
(v) double-stranded, circularised CAV DNA, derived from EcoR1 digestion of pCAU269/7.

No virus was recovered after transfection with control plasmid DNA. Transfection efficiency for double-stranded DNA was 10% as assessed by the proportion of fluorescent cells at 48 h following transfection with pEGFP plasmid.

Transfection with all single-stranded constructs resulted in a markedly higher proportion of infected cells than transfection with the double-stranded DNA construct. There was at least 50% infection of MDCC-MSB1 cells by the second culture passage after transfection with all forms of single-stranded genome. However, 50% infectivity was not seen until the fourth passage after transfection with double-stranded CAV genome. There were no differences seen in the proportion of cells infected after transfection between positive or negative-sense single-stranded genomes, nor between linear and circularised genomes.

DNA Inoculation in Embryos

The efficacy of virus growth after inoculation in ovo of different CAV genomic constructs was assessed. The different CAV genomic constructs were inoculated into the yolk sac of groups of five 7 day embryos (E7). The titres of virus in clarified homogenates of whole E18 chick embryos were determined by inoculation of MDCC-MSB1 cell cultures (Table 21). Virus was recovered from homogenised E18 embryos inoculated with the following genomic DNA constructs (Table 21):

(i) circularised, positive-sense, single-stranded, CAV DNA, prepared from the CAVM13.pos clone;
(ii) linear, positive-sense, single-stranded, CAV DNA, prepared from the CAVM13.pos clone;
(iii) circularised, negative-sense, single-stranded CAV DNA, prepared from the CAVM13.neg clone;
(iv) linear, negative-sense, single-stranded CAV DNA, prepared from the CAVM13.neg clone; and
(v) double-stranded, circularised CAV DNA, derived from EcoR1 digestion of pCAU269/7.

No virus was recovered from homogenised E18 embryos inoculated with control plasmid DNA (Table 21). The efficiency of virus growth from the inoculation of positive, circularised single-stranded genome was very low, with virus recovered from only one out of 5 embryos (Table 21). The greatest efficiency of virus growth was seen from the inoculation of circularised, negative-sense single-stranded genome, which is the form of genome present in the virion. The mean titre for circularised, negative-sense, single-stranded genome was significantly greater at the 0.001 level, than the mean titre for double-stranded genome inoculation.

The findings from this study were further confirmed by inoculation of the yolk sac of eggs after 6 days of incubation with cloned mutant viral genomes still contained within the plasmid vector. The three mutant genomes were mut C87R, mut H103Y and mut Q131P. At 16 days of incubation chorioallantoic membranes and bone marrow smears were prepared from the embryos and stained with immunofluorescent antibody against CAV VP3. In all inoculated eggs there was evidence of viral replication as demonstrable by specific staining for VP3.

V. DNA Inoculation of Embryos with Single and Double-Stranded CAV Genome

In this study a new methodology was developed for the growth of CAV in ovo after inoculation of E6 or E7 embryos with naked DNA genome. This is the first study to demonstrate for CAV that virus growth in vivo can proceed from the inoculation of DNA, and the first description of the inoculation of naked viral genome into the yolk sac for any avian viral pathogen.

This study has demonstrated the efficacy of DNA inoculation into the yolk sac for the cultivation of CAV. Delivery of CAV DNA into the yolk sac of embryos or by other in ovo routes can be used as a route of vaccination.

This methodology represents a significant advance in biosecurity due to the capacity to generate infectious virus from manipulated genome in a cell-free system. The cultivation of virus by the transfection of the manipulated genome into MDCC-MSB1 cells exposes potential vaccine inoculate to components of the cell culture system which may pose biosecurity risks. The capacity to generate virus from DNA genome inoculated into the embryonic yolk sac is therefore significant to the enhancement of biosecurity. The titre of $10^5$ to $10^6$ $TCID_{50}$ typically obtained for cultivation of CAV in MDCC-MSB1 cell culture is restrictively low. Amplification of titre could be possible through further cycles of yolk sac inoculation.

The efficacy of yolk sac inoculation was greatest for the single-stranded, negative-sense circularised genome (Table 21). High titres of infectious virus were recovered from the inoculation of single-stranded, negative-sense, circularised genome and moderate titres from yolk sac inoculation of double-stranded, circularised genome (Table 21). The titre obtained from the inoculation of embryos with single-stranded, negative-sense, circularised genome was 3 log higher than for double-stranded genome (Table 21). There was a significant difference in the titres obtained from the inoculation of circularised versus linear negative-sense genome. Viral titres obtained from the inoculation of either negative-sense linear genome, positive-sense circularised genome or positive-sense linear genome were low. Given that no differences were observed in the efficacy of transfection in MDCC-MSB1 cells between the different forms of single-stranded DNA constructs, the differences in efficacy after yolk sac inoculation are probably attributable to influences upstream from processing of the viral genome once it is in the cytoplasm. DNA constructs inoculated extracellularly into the yolk sac must persist in the yolk without degradation, and enter into host target cells for viral replication to commence. The difference observed between positive-sense and negative-sense constructs therefore most probably relates to the stability of the construct following yolk sac inoculation, and its capacity for uptake into the target cells. The folding and confirmation of the negative-sense, circularised strand may determine this difference.

Infectious virus can be generated from single-stranded genome after transfection of MDCC-MSB1 cells. There were no differences observed between positive and negative-sense strands, nor between circularised and linear constructs. This is most probably because the circular, double-stranded replicative intermediate can be synthesised from either the positive or the negative-sense strand once it is in the cytoplasm.

Transfection of single-stranded, negative-sense genome resulted in a higher infectivity at earlier passages than transfection of double-stranded genome.

Methods for the transfection of double-stranded CAV genome into MDCC-MSB1 cells have been described by Noteborn, M. H., de Boer, G. F., van Roozelaar, D. J., Jeurissen, S. H., Hoeben, R. C., Zantema, A. and Koch, G. (1991). Characterization of cloned chicken anemia virus DNA that contains all elements for the infectious replication cycle. *J Virol* 65, 3131-3139, and this technique has been replicated in many published studies. Using this technique, the DNA genome can be readily manipulated in vitro, and the alterations precisely defined, prior to generation of virions in cell culture. The transfection of single-stranded constructs may increase the efficacy of this process. A method providing enhanced transfection efficiency would be particularly beneficial for the cultivation of mutant strains with altered growth characteristics, such as extended latent periods or low burst size. Primer mutagenesis in the M13 bacteriophage cloning system involves only a single mutagenesis step for the generation of single-stranded mutant genome, and is therefore a quicker and more simple technique. The M13 bacteriophage vector is therefore a suitable alternative system to plasmid propagation for the manipulation of CAV genome.

Further studies showed that use of cloned genome, in a plasmid vector, were also able to be inoculated into the yolk sac of emryonated eggs as a method for generating infectious virus. Thus this process may be used for recovery of mutant genomes and also for production of vaccines. It also showed that direct inoculation of cloned genomes of CAV mutants into eggs may be used as a method of vaccination, especially given the demonstration that the mutant viruses are attenuated for chick embryos.

TABLE 21

Mean titres of CAV in E18 embryos following yolk sac inoculation with different genomic constructs.

| DNA inoculum | Mean titre[¶] | SD | P-value[#] |
|---|---|---|---|
| control negative | 0 | 0 | NA |
| ds[a] | 2.9 | 0.6 | *** |
| (−ve)[b] ss[c] circ[d] | 5.5 | 0.7 | *** |
| (−ve) ss lin[e] | 1.3 | 0.9 | ** |
| (+ve)[f] ss circ | 0.6 | 0.9 | ‡ |
| (+ve) ss lin | 1.6 | 0.3 | *** |

¶Mean titre as $\log_{10}TCID_{50}$/embryo
SD standard deviation
#P-value t-test between control negative and treatment
a double-stranded
b negative-sense
c single-stranded
d circularised genome
e linear genome
f positive-sense
NA not applicable
* P-value significant at 0.05 level
** P-value significant at 0.01 level
*** P-value significant at 0.001 level
‡ P-value not significant at 0.05 level VI. Assessment of Selected Mutant CAV Viruses for Attenuation and for Induction of Protective Immunity in Day Old Chicks Aim To assess safety of selected CAV mutants in day old chicks and assess protective immunity induced by inoculation of day old chicks with CAV mutants.

Method

There were be six experimental groups:

| Group | Treatment day 1 | Treatment day 21 |
|---|---|---|
| 1 | Media | Media |
| 2 | Media | Wild type CAV |
| 3 | Wild type CAV | Wild type CAV |
| 4 | Mutant 169 | Wild type CAV |
| 5 | Mutant 101 | Wild type CAV |
| 6 | Mutant 161/162 | Wild type CAV |

Each experimental group consisted of 10 birds, and each group was housed in a separate positive pressure fibreglass isolator with all entry and exit air filtered by high efficiency particle air filters and all food and water sterilised before introduction into the isolators. All chicks were individually identified by wing bands.

Half the chicks were euthanased at day 14 and removed for assessment of safety of the mutants. The remaining chicks remained in the isolators for a further 21 days.

The birds were inoculated subcutaneously with 0.5 mL of CAV containing $10^4$ median tissue culture infective doses of virus or with 0.5 mL of a lysate of uninfected MSB1 cells.

At day 14, 5 birds in each group were euthanased by exposure to halothane. At post mortem, body weights were taken and all lymphoid organs, bone marrow, liver, spleen and dermus (for evidence of haemorrhage) examined for gross pathology. The thymic chain was dissected out and weighed.

At day 21, the remaining birds in each group were inoculated subcutaneously with 0.5 mL of CAV containing $10^4$ median tissue culture infective doses of virus or with 0.5 mL of a lysate of uninfected MSB1 cells.

At day 35, the remaining birds were euthanased by exposure to halothane. At post mortem body weights were taken and all lymphoid organs, bone marrow, liver, spleen and dermus (for evidence of haemorrhage) examined/photographed for gross pathology. The thymic chain was dissected out and weighed.

Results and Discussion

There was no evidence that birds infected with virus had lower body weights than uninfected birds at day 14 and no evidence that there was any difference in body weight between any of the groups at day 35.

At day 14 there was no evidence of a difference in thymic weight or thymus/body weight ratio between birds infected with the mutant viruses 101 and 161/162 and uninfected birds. However, the thymic weight and thymus/body weight ratio of birds infected with wild type virulent virus were significantly lower than those of uninfected birds. The thymic weight and thymus/body weight ratio of birds infected with mutant 169 were not significantly different from uninfected birds or birds infected with wild type virulent virus.

Results at Day 14

| Group | Treatment day 1 | Thymus Weight (g) | Thymus/Body Weight Ratio (mg/g) |
|---|---|---|---|
| 1 | Uninfected | 1.3 ± 0.3[a] | 8.8 ± 1.6[a] |
| 2 | Uninfected | 1.1 ± 0.3[ab] | 8.4 ± 1.6[a] |
| 3 | Wild type CAV | 0.8 ± 0.3[b] | 4.9 ± 2.0[b] |
| 4 | Mutant 169 | 1.1 ± 0.3[ab] | 7.1 ± 2.1[ab] |
| 5 | Mutant 101 | 1.3 ± 0.4[a] | 8.9 ± 2.3[a] |
| 6 | Mutant 161/162 | 1.3 ± 0.3[a] | 8.3 ± 1.5[a] |

Values in the same column with the same superscript letter are not significantly different These results show that mutant viruses that were attenuated for chick embryos were also attenuated for day old chicks, with the attenuation of mutant 169 somewhat intermediate compared to that of mutants 101 and 161/162

Protection Experiment

At day 35 there was no evidence of a difference in thymic weight or thymus/body weight ratio between birds vaccinated with mutant virus 169 and then challenged with wild type virulent CAV at 21 days, birds that had not been infected, and birds that had been inoculated at 1 day old with wild type virulent CAV and then challenged with wild type virulent CAV at 21 days. However, the thymic weight and thymus/body weight ratio of birds that had not been exposed to CAV at 1 day of age but were then infected with wild type virulent virus at 21 days of age were significantly lower than these groups. Birds that had been vaccinated with mutants 101 or 161/162 and then challenged with wild type virulent virus had intermediate levels of protection.

| | Results at Day 35 | | | |
|---|---|---|---|---|
| Group | Treatment day 1 | Treatment day 21 | Thymus Weight (g) | Thymus/Body Weight Ratio (mg/g) |
| 1 | Uninfected | Uninfected | 4.1 ± 0.8$^{a}$ | 9.5 ± 1.4$^{a}$ |
| 2 | Uninfected | Wild type CAV | 1.3 ± 0.3$^{b}$ | 3.3 ± 0.9$^{b}$ |
| 3 | Wild type CAV | Wild type CAV | 5.1 ± 1.2$^{a}$ | 10.5 ± 1.9$^{a}$ |
| 4 | Mutant 169 | Wild type CAV | 3.5 ± 0.4$^{a}$ | 9.0 ± 0.8$^{a}$ |
| 5 | Mutant 101 | Wild type CAV | 2.2 ± 0.4$^{c}$ | 5.0 ± 1.4$^{b}$ |
| 6 | Mutant 161/162 | Wild type CAV | 2.0 ± 1.0$^{bc}$ | 5.2 ± 2.1$^{b}$ |

Values in the same column with the same superscript letter are not significantly different These results show that vaccination with mutant viruses was able to protect chickens against the effects of CAV infection.

Thus, the mutant CAV viruses were not only attenuated, but were also capable of inducing protective immunity in 1 day old chickens.

Discussion

I. CAV Vaccine

The present inventors have developed CAV live attenuated and DNA vaccines suitable for the inoculation of pullets, broiler and breeder flocks. A number of stages were involved in this process including:

- establishing an in vitro cell culture system for the analysis and growth of virus;
- analysing virus for appropriate sites for mutagenesis and investigation of viral function;
- site-directed mutagenesis utilising PCR on a full genome clone;
- transfection of mutant viruses in a cell culture system and assessment for infectivity, cytopathogenic effects and specific changes in viral function;
- testing mutant viruses as potential vaccine candidates in a challenge model using SPF chick embryos; and
- assessing phenotype and in vivo infectivity of mutant viruses in the challenge model.

The results from pathogenicity testing in chick embryos clearly demonstrated that mutation of VP2 in the key regions of structure and function identified was able to be used to generate attenuated virus that would be suitable for vaccination, either as attenuated virus or as a DNA vaccine. All mutants with the exception of mut 163 were significantly attenuated as measured by the total lesion score. However, mut 163 was significantly attenuated as measured by thymus and spleen lesion scores.

It was notable that the most significant effects on attenuation were achieved by mutation of the residues predicted to be involved directly in the PTPase function of the VP2, but that some attenuation was also achieved by mutating the acidic and basic regions at the carboxyl end of VP2.

In addition, mutation of the Kozac's sequence at the point of translational initiation of the VP2 gene, such that more VP2 would be produced, resulted in a construct that was no longer capable of productive replication. Such a construct, while not useful as a basis for developing a live attenuated vaccine, can be used as a DNA vaccine.

These studies have also demonstrated that VP2 has a potent immunomodulatory effect. Mutant VP2 thus can be used to effect less potent changes in the immune system.

II. Mutation of the Translational Initiation Signals of CAV VP2

These studies have demonstrated the general application of mutation of the gene for VP2 in CAV and its homologues in other circoviruses for the generation of attenuated strains for use as live vaccines or DNA vaccines and for the generation of non-replicating genomic clones that can be used as DNA vaccines.

In addition, the present inventors have clearly demonstrated the role that VP2 plays in immunomodulation during CAV infections. It has been found that VP2 and its homologues can be used to influence the function of the immune system.

There is some potential for using replication deficient mutants, pCAU283-3 and pCAU283+4 as DNA vaccines in chickens in that transient expression of VP2/VP3 may be sufficient to elicit immune response

SUMMARY

The present inventors have found that directed mutagenesis is a feasible strategy for the production of an attenuated viral strain, firstly as the genome of CAV is amenable to manipulation due to its small size, and secondly as virus particles can be readily generated by transfection of genome alone. Directed mutations can be introduced into the genome in a cell and virus free system and precisely characterised prior to the production of virus. This strategy is therefore highly efficient and employs optimal biosecurity. A limitation to the employment of a live attenuated vaccine is the low titre to which virus grows in vitro and the minor inconvenience due to the requirement for virus production in embryonated specific pathogen free (SPF) eggs. The development of a DNA vaccine eliminates the biosecurity risk of culture production and the limitations of low viral titres, and may prove to be efficacious for in ovo inoculation. Alternative approaches to the live attenuated vaccine are inactivated vaccines or live vaccines attenuated through passage. Inoculation of chicks with co-expressed VP1 and VP2 generates a serum neutralising antibody response protective against challenge. Live attenuated viruses, however, typically have greater capacity for immunogenicity due to induction of both humoral and cell mediated immunity. Strains which have been attenuated through passage are suboptimal as vaccine candidates as they retain low levels of pathogenicity. In addition, passaged attenuated strains rapidly revert to virulent forms with passaging in chicks. Therefore, there are significant advantages in the use of site directed mutagenesis on a recombinant genome for use as a DNA vaccine or for the derivation of live attenuated strains. Vaccine program design may incorporate the administration of DNA vaccines to embryonated eggs and of live attenuated vaccine to older birds.

The organisational features of the CAV genome both limit and enhance the possibilities for attenuation through mutagenesis whilst concurrently retaining infectivity and immunogenicity. CAV is extremely economical in its coding capacity. The genome is only 2.3 kb and encodes three overlapping ORFs, limiting the options available for mutagenesis. Mutations in one ORF must be designed so as not to disrupt overlapping ORFs. The functions of all three viral proteins are critical to viral infectivity and therefore introduced mutations must ensure retention of protein function. The stability of attenuation can be enhanced through a multi-factorial approach. Reversion to virulence is expected to occur at a low frequency with reliance on simple point mutations. CAV has extreme sequence conservation in all characterised isolates across the coding regions containing overlapping reading frames. This suggests that in the field situation, the capacity for spontaneous mutations to be tolerated by the virus is kept well below the expected rate of naturally occurring mutation associated with the error rate of the polymerase enzyme system. This is most probably a consequence of the restriction imposed on codon change in one frame due to concurrent changes in the overlapping frame which may be deleterious. This argument also suggests that a strategy of passage attenuation will be extremely slow and may not produce the optimal attenuation that can be achieved through targeted mutagenesis. Naturally occurring mutations will only be tolerated at a measurable frequency in codons for which the overlapping reading frame has codon wobble. Site directed mutagenesis is therefore optimal as it does not rely on the probability of low frequency mutational events and sites where the overlapping ORF has minimal codon wobble can be readily mutated through careful design. Mutations introduced by site directed mutagenesis in vitro that preserve the overlapping frame will have a reduced frequency of reversion due to the necessity for codon conservation in the overlapping frame. Attenuation requires a rationally designed strategy of carefully constructed mutations using site-directed mutagenesis.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

SEQUENCE LISTING

```
<160> NUMBER OF SEQ ID NOS: 71

<210> SEQ ID NO 1
<211> LENGTH: 2286
<212> TYPE: DNA
<213> ORGANISM: Artificial Sequence
<220> FEATURE:
<223> OTHER INFORMATION: DNA sequence of pCAU269/7

<400> SEQUENCE: 1

cccccttga accccccct gggggggatt ccccccaga ccccccttt ataaagcact      60

caataaacgc agctaattcg ttcaccgcac aatcgctttc cgagtggtta ctattccatc    120

accattctag cctgtacaca aaaagtaaag atggacgaat cgctcgactt cgctcgcgat    180

tcgtcgaagg cggggggccg gaggcccccc ggtggccccc tccaaggagt ggagcgtgta    240

caggggggta cgtcatccgt acaggggggg tacgtcacaa gaaggcgttc ccgtacaggg    300

gggtacgtaa catgttcagg ggggtacgtc acaaccaatc aggagctgcc acgttgcgaa    360

agtgacgttt cgaaaatggg cggcgcaaga ctccctatat attgcgcgca cataccggtc    420

ggcagtaggt atacgcaagg cggtccgggt ggatgcacgg aaacggcgga caaccggccg    480

ctgggggcag tgaatcggcg cttagccgag aggggcaacc tgggcccagc ggagccgcgc    540

aggggcaagt aatttcaaat gaacgctcac caagaagata ctccaccagg accatcaacg    600

gtgttcaggc caccaacaag ttcacggccg ttggaaaccc ctcactgcag agagatccgg    660

attggtatcg ctggaattac agtcactcta tcgctgtgtg gctgcgcgaa tgctcgcgtt    720

cccacgctaa gatctgcaac tgcggacaat tcagaaaaca ctggtttcaa gaatgtgccg    780

gacttgagga ccgatcaacc caagcctccc tcgaagaagc gatcctgcga cccctccgag    840

tacagggtaa gcgagctaaa agaaagcttg attaccacta ctcccagccg accccgaacc    900

gcaagaaggt gtataagact gtaagatggc aagacgagct cgcagaccga gaggccgatt    960
```

-continued

```
ttacgccttc agaagaggac ggtggcacca cctcaagcga cttcgacgaa gatataaatt   1020

tcgacatcgg aggagacagc ggtatcgtag acgagctttt aggaaggcct ttcacaaccc   1080

ccgccccggt acgtatagtg tgaggctgcc aaaccccag tccacgatga ctatccgctt    1140

ccaaggagtc atctttctca ccgaaggact cattctacct aaaaacagca cagctggggg   1200

ctatgcggac cacatgtacg gggcgagagt cgccaagatc tcagtgaacc tgaaagagtt   1260

cctcctagca tcaatgaacc tgacatacgt gagcaagata ggaggcccca tcgccggtga   1320

gttgattgcg gacgggtcta aatcgcaagc cgcggagaac tggccaaatt gctggctgcc   1380

gctagataat aacgtgccct ccgctacacc atctgcatgg tggagatggg ctttaatgat   1440

gatgcagcca acggactcct gccggttttt taatcaccct aagcaaatga ccctgcaaga   1500

catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc cccggaccc cccgatcatc accactacca ctgcgcaagg    1800

cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggaccccca agggccagag  1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                              2286
```

<210> SEQ ID NO 2
<211> LENGTH: 216
<212> TYPE: PRT
<213> ORGANISM: Artificial sequence
<220> FEATURE:
<223> OTHER INFORMATION: protein sequence of VP2 of pCAU269/7

<400> SEQUENCE: 2

```
Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
```

-continued

```
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215


<210> SEQ ID NO 3
<211> LENGTH: 2286
<212> TYPE: DNA
<213> ORGANISM: Artificial Sequence
<220> FEATURE:
<223> OTHER INFORMATION: mut C 86 R of Chicken anaemia virus genome

<400> SEQUENCE: 3

cccccttga accccccct ggggggatt cccccccaga ccccccttt ataaagcact     60

caataaacgc agctaattcg ttcaccgcac aatcgctttc cgagtggtta ctattccatc    120

accattctag cctgtacaca aaaagtaaag atggacgaat cgctcgactt cgctcgcgat    180

tcgtcgaagg cgggggccg gaggcccccc ggtggccccc tccaaggagt ggagcgtgta    240

cagggggta cgtcatccgt acagggggg tacgtcacaa gaaggcgttc ccgtacaggg    300

gggtacgtaa catgttcagg ggggtacgtc acaaccaatc aggagctgcc acgttgcgaa    360

agtgacgttt cgaaaatggg cggcgcaaga ctccctatat attgcgcgca cataccggtc    420

ggcagtaggt atacgcaagg cggtccgggt ggatgcacgg aaacggcgga caaccggccg    480

ctgggggcag tgaatcggcg cttagccgag aggggcaacc tgggcccagc ggagccgcgc    540

aggggcaagt aatttcaaat gaacgctcac caagaagata ctccaccagg accatcaacg    600

gtgttcaggc caccaacaag ttcacggccg ttggaaaccc ctcactgcag agagatccgg    660

attggtatcg ctggaattac agtcactcta tcgctgtgtg gctgcgcgaa cgctcgcgtt    720

cccacgctaa gatctgcaac tgcggacaat tcagaaaaca ctggtttcaa gaatgtgccg    780

gacttgagga ccgatcaacc caagcctccc tcgaagaagc gatcctgcga cccctccgag    840

tacagggtaa gcgagctaaa agaaagcttg attaccacta ctcccagccg accccgaacc    900

gcaagaaggt gtataagact gtaagatggc aagacgagct cgcagaccga gaggccgatt    960

ttacgccttc agaagaggac ggtggcacca cctcaagcga cttcgacgaa gatataaatt   1020

tcgacatcgg aggagacagc ggtatcgtag acgagctttt aggaaggcct ttcacaaccc   1080

ccgccccggt acgtatagtg tgaggctgcc aaacccccag tccacgatga ctatccgctt   1140

ccaaggagtc atctttctca ccgaaggact cattctacct aaaaacagca cagctggggg   1200

ctatgcggac cacatgtacg gggcgagagt cgccaagatc tcagtgaacc tgaaagagtt   1260

cctcctagca tcaatgaacc tgacatacgt gagcaagata ggaggcccca tcgccggtga   1320

gttgattgcg gacgggtcta aatcgcaagc cgcggagaac tggccaaatt gctggctgcc   1380

gctagataat aacgtgccct ccgctacacc atctgcatgg tggagatggg ctttaatgat   1440

gatgcagcca acggactcct gccggttttt taatcaccct aagcaaatga ccctgcaaga   1500
```

-continued

```
catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc cccggaccc cccgatcatc accactacca ctgcgcaagg   1800

cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggacccca agggccagag   1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                              2286
```

```
<210> SEQ ID NO 4
<211> LENGTH: 216
<212> TYPE: PRT
<213> ORGANISM: Artificial Sequence
<220> FEATURE:
<223> OTHER INFORMATION: mut C 86 R of VP2 of Chicken anaemia virus

<400> SEQUENCE: 4

Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Arg Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
```

-continued 210 215

<210> SEQ ID NO 5
<211> LENGTH: 2286
<212> TYPE: DNA
<213> ORGANISM: Artificial Sequence
<220> FEATURE:
<223> OTHER INFORMATION: mut C 95 S of Chicken anaemia virus genome

<400> SEQUENCE: 5

```
cccccttga accccccct ggggggggatt cccccccaga cccccccttt ataaagcact     60
caataaacgc agctaattcg ttcaccgcac aatcgctttc cgagtggtta ctattccatc    120
accattctag cctgtacaca aaaagtaaag atggacgaat cgctcgactt cgctcgcgat    180
tcgtcgaagg cggggggccg gaggcccccc ggtggccccc tccaaggagt ggagcgtgta    240
caggggggta cgtcatccgt acaggggggg tacgtcacaa gaaggcgttc ccgtacaggg    300
gggtacgtaa catgttcagg ggggtacgtc acaaccaatc aggagctgcc acgttgcgaa    360
agtgacgttt cgaaaatggg cggcgcaaga ctccctatat attgcgcgca cataccggtc    420
ggcagtaggt atacgcaagg cggtccgggt ggatgcacgg aaacggcgga caaccggccg    480
ctgggggcag tgaatcggcg cttagccgag aggggcaacc tgggcccagc ggagccgcgc    540
aggggcaagt aatttcaaat gaacgctcac caagaagata ctccaccagg accatcaacg    600
gtgttcaggc caccaacaag ttcacggccg ttggaaaccc ctcactgcag agagatccgg    660
attggtatcg ctggaattac agtcactcta tcgctgtgtg gctgcgcgaa tgctcgcgtt    720
cccacgctaa gatcagcaac tgcggacaat tcagaaaaca ctggtttcaa gaatgtgccg    780
gacttgagga ccgatcaacc caagcctccc tcgaagaagc gatcctgcga cccctccgag    840
tacagggtaa gcgagctaaa agaaagcttg attaccacta ctcccagccg accccgaacc    900
gcaagaaggt gtataagact gtaagatggc aagacgagct cgcagaccga gaggccgatt    960
ttacgccttc agaagaggac ggtggcacca cctcaagcga cttcgacgaa gatataaatt   1020
tcgacatcgg aggagacagc ggtatcgtag acgagctttt aggaaggcct ttcacaaccc   1080
ccgccccggt acgtatagtg tgaggctgcc aaacccccag tccacgatga ctatccgctt   1140
ccaaggagtc atctttctca ccgaaggact cattctacct aaaaacagca cagctggggg   1200
ctatgcggac cacatgtacg gggcgagagt cgccaagatc tcagtgaacc tgaaagagtt   1260
cctcctagca tcaatgaacc tgacatacgt gagcaagata ggaggcccca tcgccggtga   1320
gttgattgcg gacgggtcta aatcgcaagc cgcggagaac tggccaaatt gctggctgcc   1380
gctagataat aacgtgccct ccgctacacc atctgcatgg tggagatggg ctttaatgat   1440
gatgcagcca acggactcct gccggttttt taatcaccct aagcaaatga ccctgcaaga   1500
catgggtcgg atgtttgggg gctggcatct gttccgacac attgaaaccc gctttcagct   1560
ccttgccact aagaatgagg gatccttcag ccccgtggcg agtcttctct cccagggaga   1620
gtacctcacg cgccgcgacg atgttaagta cagcagcgac caccagaacc ggtggcgaaa   1680
aggcgagcaa ccgatgacgg gggggattgc ttacgcgacc ggtaaaatga gactcgacga   1740
gcaacaatac cctgctatgc ccccggaccc cccgatcatc accactacca ctgcgcaagg   1800
cacgcaagtc cgctgcatga atagcacgca agcttggtgg tcgtgggaca catatatgag   1860
ctttgcaaca ctcacagcac tcggtgctca atggtctttt cctccagggc aacgttcagt   1920
ttctagacgg tccttcaacc atcacaaggc ccgaggagcc ggggacccca agggccagag   1980
gtggcacacg ctggtgccgc tcggcacaga gaccataacc gacagctaca tgagagcacc   2040
```

ggcatcagag ctggacacga atttcttcac gctttacgta gcgcaaggca ctaataaatc 2100
gcagcaatac aagttcggca cagcaacata cgcgctaaag gaacccgtaa tgaagagcga 2160
ttcatgggca gtggtgcgcg tccagtccgt ctggcaactg ggtaacaggc aaaggccata 2220
cccgtgggac gttaactggg ccaacagcac catgtactgg gggtcgcagc cctgaaaagg 2280
gggggg 2286

<210> SEQ ID NO 6
<211> LENGTH: 216
<212> TYPE: PRT
<213> ORGANISM: Artificial Sequence
<220> FEATURE:
<223> OTHER INFORMATION: mut C 95 S of VP2 of Chicken anaemia virus

<400> SEQUENCE: 6

Met His Gly Asn Gly Gly Gln Pro Ala Ala Gly Gly Ser Glu Ser Ala
1 5 10 15

Leu Ser Arg Glu Gly Gln Pro Gly Pro Ser Gly Ala Ala Gln Gly Gln
20 25 30

Val Ile Ser Asn Glu Arg Ser Pro Arg Arg Tyr Ser Thr Arg Thr Ile
35 40 45

Asn Gly Val Gln Ala Thr Asn Lys Phe Thr Ala Val Gly Asn Pro Ser
50 55 60

Leu Gln Arg Asp Pro Asp Trp Tyr Arg Trp Asn Tyr Ser His Ser Ile
65 70 75 80

Ala Val Trp Leu Arg Glu Cys Ser Arg Ser His Ala Lys Ile Ser Asn
85 90 95

Cys Gly Gln Phe Arg Lys His Trp Phe Gln Glu Cys Ala Gly Leu Glu
100 105 110

Asp Arg Ser Thr Gln Ala Ser Leu Glu Glu Ala Ile Leu Arg Pro Leu
115 120 125

Arg Val Gln Gly Lys Arg Ala Lys Arg Lys Leu Asp Tyr His Tyr Ser
130 135 140

Gln Pro Thr Pro Asn Arg Lys Lys Val Tyr Lys Thr Val Arg Trp Gln
145 150 155 160

Asp Glu Leu Ala Asp Arg Glu Ala Asp Phe Thr Pro Ser Glu Glu Asp
165 170 175

Gly Gly Thr Thr Ser Ser Asp Phe Asp Glu Asp Ile Asn Phe Asp Ile
180 185 190

Gly Gly Asp Ser Gly Ile Val Asp Glu Leu Leu Gly Arg Pro Phe Thr
195 200 205

Thr Pro Ala Pro Val Arg Ile Val
210 215

<210> SEQ ID NO 7
<211> LENGTH: 2286
<212> TYPE: DNA
<213> ORGANISM: Artificial Sequence
<220> FEATURE:
<223> OTHER INFORMATION: mut C 97 S of Chicken anaemia virus genome

<400> SEQUENCE: 7 cccccttga acccccccct ggggggggatt cccccccaga cccccccttt ataaagcact 60
caataaacgc agctaattcg ttcaccgcac aatcgctttc cgagtggtta ctattccatc 120
accattctag cctgtacaca aaaagtaaag atggacgaat cgctcgactt cgctcgcgat 180

-continued

```
tcgtcgaagg cggggggccg gaggcccccc ggtggccccc tccaaggagt ggagcgtgta    240
caggggggta cgtcatccgt acaggggggg tacgtcacaa gaaggcgttc ccgtacaggg    300
gggtacgtaa catgttcagg ggggtacgtc acaaccaatc aggagctgcc acgttgcgaa    360
agtgacgttt cgaaaatggg cggcgcaaga ctccctatat attgcgcgca cataccggtc    420
ggcagtaggt atacgcaagg cggtccgggt ggatgcacgg aaacggcgga caaccggccg    480
ctgggggcag tgaatcggcg cttagccgag aggggcaacc tgggcccagc ggagccgcgc    540
aggggcaagt aatttcaaat gaacgctcac caagaagata ctccaccagg accatcaacg    600
gtgttcaggc caccaacaag ttcacggccg ttggaaaccc ctcactgcag agagatccgg    660
attggtatcg ctggaattac agtcactcta tcgctgtgtg gctgcgcgaa tgctcgcgtt    720
cccacgctaa gatctgcaac agcggacaat tcagaaaaca ctggtttcaa gaatgtgccg    780
gacttgagga ccgatcaacc caagcctccc tcgaagaagc gatcctgcga cccctccgag    840
tacagggtaa gcgagctaaa agaaagcttg attaccacta ctcccagccg accccgaacc    900
gcaagaaggt gtataagact gtaagatggc aagacgagct cgcagaccga gaggccgatt    960
ttacgccttc agaagaggac ggtggcacca cctcaagcga cttcgacgaa gatataaatt   1020
tcgacatcgg aggagacagc ggtatcgtag acgagctttt aggaaggcct ttcacaaccc   1080
ccgccccggt acgtatagtg tgaggctgcc aaacccccag tccacgatga ctatccgctt   1140
ccaaggagtc atctttctca ccgaaggact cattctacct aaaaacagca cagctggggg   1200
ctatgcggac cacatgtacg gggcgagagt cgccaagatc tcagtgaacc tgaaagagtt   1260
cctcctagca tcaatgaacc tgacatacgt gagcaagata ggaggcccca tcgccggtga   1320
gttgattgcg gacgggtcta aatcgcaagc cgcggagaac tggccaaatt gctggctgcc   1380
gctagataat aacgtgccct ccgctacacc atctgcatgg tggagatggg ctttaatgat   1440
gatgcagcca acggactcct gccggttttt taatcaccct aagcaaatga ccctgcaaga   1500
catgggtcgg atgtttgggg gctggcatct gttccgacac attgaaaccc gctttcagct   1560
ccttgccact aagaatgagg gatccttcag ccccgtggcg agtcttctct cccagggaga   1620
gtacctcacg cgccgcgacg atgttaagta cagcagcgac caccagaacc ggtggcgaaa   1680
aggcgagcaa ccgatgacgg gggggattgc ttacgcgacc ggtaaaatga gactcgacga   1740
gcaacaatac cctgctatgc ccccggaccc cccgatcatc accactacca ctgcgcaagg   1800
cacgcaagtc cgctgcatga atagcacgca agcttggtgg tcgtgggaca catatatgag   1860
ctttgcaaca ctcacagcac tcggtgctca atggtctttt cctccagggc aacgttcagt   1920
ttctagacgg tccttcaacc atcacaaggc ccgaggagcc ggggacccca agggccagag   1980
gtggcacacg ctggtgccgc tcggcacaga gaccataacc gacagctaca tgagagcacc   2040
ggcatcagag ctggacacga atttcttcac gctttacgta gcgcaaggca ctaataaatc   2100
gcagcaatac aagttcggca cagcaacata cgcgctaaag gaacccgtaa tgaagagcga   2160
ttcatgggca gtggtgcgcg tccagtccgt ctggcaactg ggtaacaggc aaaggccata   2220
cccgtgggac gttaactggg ccaacagcac catgtactgg gggtcgcagc cctgaaaagg   2280
gggggg                                                              2286
```

<210> SEQ ID NO 8
<211> LENGTH: 216
<212> TYPE: PRT
<213> ORGANISM: Artificial Sequence
<220> FEATURE:
<223> OTHER INFORMATION: mut C 97 S of VP2 of Chicken anaemia virus -continued sequence

<400> SEQUENCE: 8

Met His Gly Asn Gly Gly Gln Pro Ala Ala Gly Gly Ser Glu Ser Ala
1 5 10 15

Leu Ser Arg Glu Gly Gln Pro Gly Pro Ser Gly Ala Ala Gln Gly Gln
20 25 30

Val Ile Ser Asn Glu Arg Ser Pro Arg Arg Tyr Ser Thr Arg Thr Ile
35 40 45

Asn Gly Val Gln Ala Thr Asn Lys Phe Thr Ala Val Gly Asn Pro Ser
50 55 60

Leu Gln Arg Asp Pro Asp Trp Tyr Arg Trp Asn Tyr Ser His Ser Ile
65 70 75 80

Ala Val Trp Leu Arg Glu Cys Ser Arg Ser His Ala Lys Ile Cys Asn
85 90 95

Ser Gly Gln Phe Arg Lys His Trp Phe Gln Glu Cys Ala Gly Leu Glu
100 105 110

Asp Arg Ser Thr Gln Ala Ser Leu Glu Glu Ala Ile Leu Arg Pro Leu
115 120 125

Arg Val Gln Gly Lys Arg Ala Lys Arg Lys Leu Asp Tyr His Tyr Ser
130 135 140

Gln Pro Thr Pro Asn Arg Lys Lys Val Tyr Lys Thr Val Arg Trp Gln
145 150 155 160

Asp Glu Leu Ala Asp Arg Glu Ala Asp Phe Thr Pro Ser Glu Glu Asp
165 170 175

Gly Gly Thr Thr Ser Ser Asp Phe Asp Glu Asp Ile Asn Phe Asp Ile
180 185 190

Gly Gly Asp Ser Gly Ile Val Asp Glu Leu Leu Gly Arg Pro Phe Thr
195 200 205

Thr Pro Ala Pro Val Arg Ile Val
210 215

<210> SEQ ID NO 9
<211> LENGTH: 2286
<212> TYPE: DNA
<213> ORGANISM: Artificial Sequence
<220> FEATURE:
<223> OTHER INFORMATION: mut R 101 G of Chicken anaemia virus genome

<400> SEQUENCE: 9 cccccttga acccccccct gggggggatt ccccccaga cccccccttt ataaagcact 60
caataaacgc agctaattcg ttcaccgcac aatcgctttc cgagtggtta ctattccatc 120
accattctag cctgtacaca aaaagtaaag atggacgaat cgctcgactt cgctcgcgat 180
tcgtcgaagg cgggggccg gaggcccccc ggtggccccc tccaaggagt ggagcgtgta 240
caggggggta cgtcatccgt acaggggggg tacgtcacaa gaaggcgttc ccgtacaggg 300
gggtacgtaa catgttcagg ggggtacgtc acaaccaatc aggagctgcc acgttgcgaa 360
agtgacgttt cgaaaatggg cggcgcaaga ctccctatat attgcgcgca cataccggtc 420
ggcagtaggt atacgcaagg cggtccgggt ggatgcacgg aaacggcgga caaccggccg 480
ctgggggcag tgaatcggcg cttagccgag aggggcaacc tgggcccagc ggagccgcgc 540
aggggcaagt aatttcaaat gaacgctcac caagaagata ctccaccagg accatcaacg 600
gtgttcaggc caccaacaag ttcacggccg ttggaaaccc ctcactgcag agagatccgg 660
attggtatcg ctggaattac agtcactcta tcgctgtgtg gctgcgcgaa tgctcgcgtt 720

-continued

```
cccacgctaa gatctgcaac tgcggacaat tcggaaaaca ctggtttcaa gaatgtgccg    780
gacttgagga ccgatcaacc caagcctccc tcgaagaagc gatcctgcga cccctccgag    840
tacagggtaa gcgagctaaa agaaagcttg attaccacta ctcccagccg accccgaacc    900
gcaagaaggt gtataagact gtaagatggc aagacgagct cgcagaccga gaggccgatt    960
ttacgccttc agaagaggac ggtggcacca cctcaagcga cttcgacgaa gatataaatt   1020
tcgacatcgg aggagacagc ggtatcgtag acgagctttt aggaaggcct ttcacaaccc   1080
ccgccccggt acgtatagtg tgaggctgcc aaaccccccag tccacgatga ctatccgctt   1140
ccaaggagtc atctttctca ccgaaggact cattctacct aaaaacagca cagctggggg   1200
ctatgcggac cacatgtacg gggcgagagt cgccaagatc tcagtgaacc tgaaagagtt   1260
cctcctagca tcaatgaacc tgacatacgt gagcaagata ggaggcccca tcgccggtga   1320
gttgattgcg gacgggtcta aatcgcaagc cgcggagaac tggccaaatt gctggctgcc   1380
gctagataat aacgtgccct ccgctacacc atctgcatgg tggagatggg ctttaatgat   1440
gatgcagcca acggactcct gccggttttt taatcaccct aagcaaatga ccctgcaaga   1500
catgggtcgg atgtttgggg gctggcatct gttccgacac attgaaaccc gctttcagct   1560
ccttgccact aagaatgagg gatccttcag ccccgtggcg agtcttctct cccagggaga   1620
gtacctcacg cgccgcgacg atgttaagta cagcagcgac caccagaacc ggtggcgaaa   1680
aggcgagcaa ccgatgacgg gggggattgc ttacgcgacc ggtaaaatga gactcgacga   1740
gcaacaatac cctgctatgc cccggaccc cccgatcatc accactacca ctgcgcaagg   1800
cacgcaagtc cgctgcatga atagcacgca agcttggtgg tcgtgggaca catatatgag   1860
ctttgcaaca ctcacagcac tcggtgctca atggtctttt cctccagggc aacgttcagt   1920
ttctagacgg tccttcaacc atcacaaggc ccgaggagcc ggggacccca agggccagag   1980
gtggcacacg ctggtgccgc tcggcacaga gaccataacc gacagctaca tgagagcacc   2040
ggcatcagag ctggacacga atttcttcac gctttacgta gcgcaaggca ctaataaatc   2100
gcagcaatac aagttcggca cagcaacata cgcgctaaag gaacccgtaa tgaagagcga   2160
ttcatgggca gtggtgcgcg tccagtccgt ctggcaactg ggtaacaggc aaaggccata   2220
cccgtgggac gttaactggg ccaacagcac catgtactgg gggtcgcagc cctgaaaagg   2280
gggggg                                                              2286
```

<210> SEQ ID NO 10
<211> LENGTH: 216
<212> TYPE: PRT
<213> ORGANISM: Artificial Sequence
<220> FEATURE:
<223> OTHER INFORMATION: mut R 101 G of VP2 of Chicken anaemia virus

<400> SEQUENCE: 10

```
Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80
```

-continued

```
Ala Val Trp Leu Arg Glu Cys Ser Arg Ser His Ala Lys Ile Cys Asn
                85                  90                  95

Cys Gly Gln Phe Gly Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215
```

<210> SEQ ID NO 11
<211> LENGTH: 2286
<212> TYPE: DNA
<213> ORGANISM: Artificial Sequence
<220> FEATURE:
<223> OTHER INFORMATION: mut H 103 Y of Chicken anaemia virus genome

<400> SEQUENCE: 11

```
cccccttga accccccct ggggggatt cccccccaga ccccccttt ataaagcact     60

caataaacgc agctaattcg ttcaccgcac aatcgctttc cgagtggtta ctattccatc    120

accattctag cctgtacaca aaaagtaaag atggacgaat cgctcgactt cgctcgcgat    180

tcgtcgaagg cgggggccg gaggcccccc ggtggccccc tccaaggagt ggagcgtgta    240

caggggggta cgtcatccgt acagggggg tacgtcacaa gaaggcgttc ccgtacaggg    300

gggtacgtaa catgttcagg ggggtacgtc acaaccaatc aggagctgcc acgttgcgaa    360

agtgacgttt cgaaaatggg cggcgcaaga ctccctatat attgcgcgca cataccggtc    420

ggcagtaggt atacgcaagg cggtccgggt ggatgcacgg aaacggcgga caaccggccg    480

ctgggggcag tgaatcggcg cttagccgag aggggcaacc tgggcccagc ggagccgcgc    540

aggggcaagt aatttcaaat gaacgctcac caagaagata ctccaccagg accatcaacg    600

gtgttcaggc caccaacaag ttcacggccg ttggaaaccc ctcactgcag agagatccgg    660

attggtatcg ctggaattac agtcactcta tcgctgtgtg gctgcgcgaa tgctcgcgtt    720

cccacgctaa gatctgcaac tgcggacaat tcagaaaata ctggtttcaa gaatgtgccg    780

gacttgagga ccgatcaacc caagcctccc tcgaagaagc gatcctgcga cccctccgag    840

tacagggtaa gcgagctaaa agaaagcttg attaccacta ctcccagccg accccgaacc    900

gcaagaaggt gtataagact gtaagatggc aagacgagct cgcagaccga gaggccgatt    960

ttacgccttc agaagaggac ggtggcacca cctcaagcga cttcgacgaa gatataaatt   1020

tcgacatcgg aggagacagc ggtatcgtag acgagctttt aggaaggcct ttcacaaccc   1080

ccgccccggt acgtatagtg tgaggctgcc aaacccccag tccacgatga ctatccgctt   1140

ccaaggagtc atctttctca ccgaaggact cattctacct aaaaacagca cagctggggg   1200

ctatgcggac cacatgtacg ggcgagagt cgccaagatc tcagtgaacc tgaaagagtt   1260
```

-continued

```
cctcctagca tcaatgaacc tgacatacgt gagcaagata ggaggcccca tcgccggtga   1320

gttgattgcg gacgggtcta aatcgcaagc cgcggagaac tggccaaatt gctggctgcc   1380

gctagataat aacgtgccct ccgctacacc atctgcatgg tggagatggg ctttaatgat   1440

gatgcagcca acggactcct gccggttttt taatcaccct aagcaaatga ccctgcaaga   1500

catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc ccccggaccc ccgatcatc accactacca ctgcgcaagg   1800

cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggacccca agggccagag   1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                              2286
```

```
<210> SEQ ID NO 12
<211> LENGTH: 216
<212> TYPE: PRT
<213> ORGANISM: Artificial Sequence
<220> FEATURE:
<223> OTHER INFORMATION: mut H 103 Y of VP2 of Chicken anaemia virus

<400> SEQUENCE: 12

Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys Tyr Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175
```

-continued

```
Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215


<210> SEQ ID NO 13
<211> LENGTH: 2286
<212> TYPE: DNA
<213> ORGANISM: artificial sequence
<220> FEATURE:
<223> OTHER INFORMATION: mut R 129 G of Chicken anaemia virus genome

<400> SEQUENCE: 13

cccccttga accccccct ggggggatt ccccccaga ccccccttt ataaagcact      60

caataaacgc agctaattcg ttcaccgcac aatcgctttc cgagtggtta ctattccatc    120

accattctag cctgtacaca aaaagtaaag atggacgaat cgctcgactt cgctcgcgat    180

tcgtcgaagg cggggggccg gaggcccccc ggtggccccc tccaaggagt ggagcgtgta    240

caggggggta cgtcatccgt acaggggggg tacgtcacaa gaaggcgttc ccgtacaggg    300

gggtacgtaa catgttcagg ggggtacgtc acaaccaatc aggagctgcc acgttgcgaa    360

agtgacgttt cgaaaatggg cggcgcaaga ctccctatat attgcgcgca cataccggtc    420

ggcagtaggt atacgcaagg cggtccgggt ggatgcacgg aaacggcgga caaccggccg    480

ctgggggcag tgaatcggcg cttagccgag aggggcaacc tgggcccagc ggagccgcgc    540

aggggcaagt aatttcaaat gaacgctcac caagaagata ctccaccagg accatcaacg    600

gtgttcaggc caccaacaag ttcacggccg ttggaaaccc ctcactgcag agagatccgg    660

attggtatcg ctggaattac agtcactcta tcgctgtgtg gctgcgcgaa tgctcgcgtt    720

cccacgctaa gatctgcaac tgcggacaat tcagaaaaca ctggtttcaa gaatgtgccg    780

gacttgagga ccgatcaacc caagcctccc tcgaagaagc gatcctgcga cccctcggag    840

tacagggtaa gcgagctaaa agaaagcttg attaccacta ctcccagccg accccgaacc    900

gcaagaaggt gtataagact gtaagatggc aagacgagct cgcagaccga gaggccgatt    960

ttacgccttc agaagaggac ggtggcacca cctcaagcga cttcgacgaa gatataaatt   1020

tcgacatcgg aggagacagc ggtatcgtag acgagctttt aggaaggcct ttcacaaccc   1080

ccgccccggt acgtatagtg tgaggctgcc aaaccccccag tccacgatga ctatccgctt   1140

ccaaggagtc atctttctca ccgaaggact cattctacct aaaaacagca cagctggggg   1200

ctatgcggac cacatgtacg ggcgagagt cgccaagatc tcagtgaacc tgaaagagtt   1260

cctcctagca tcaatgaacc tgacatacgt gagcaagata ggaggcccca tcgccggtga   1320

gttgattgcg gacgggtcta aatcgcaagc cgcggagaac tggccaaatt gctggctgcc   1380

gctagataat aacgtgccct ccgctacacc atctgcatgg tggagatggg ctttaatgat   1440

gatgcagcca acggactcct gccggttttt taatcaccct aagcaaatga ccctgcaaga   1500

catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc cccggaccc cccgatcatc accactacca ctgcgcaagg    1800
```

-continued

```
cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggacccca agggccagag   1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                              2286
```

```
<210> SEQ ID NO 14
<211> LENGTH: 216
<212> TYPE: PRT
<213> ORGANISM: Artificial Sequence
<220> FEATURE:
<223> OTHER INFORMATION: mut R129 G of VP2 of Chicken anaemia virus

<400> SEQUENCE: 14

Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Gly Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215


<210> SEQ ID NO 15
<211> LENGTH: 2286
<212> TYPE: DNA
<213> ORGANISM: Artificial Sequence
<220> FEATURE:
<223> OTHER INFORMATION: mut Q 131 P of Chicken anaemia virus genome
```

-continued

<400> SEQUENCE: 15

```
cccccccttga acccccccct ggggggggatt cccccccaga cccccccttt ataaagcact     60
caataaacgc agctaattcg ttcaccgcac aatcgctttc cgagtggtta ctattccatc    120
accattctag cctgtacaca aaaagtaaag atggacgaat cgctcgactt cgctcgcgat    180
tcgtcgaagg cggggggccg gaggcccccc ggtggccccc tccaaggagt ggagcgtgta    240
caggggggta cgtcatccgt acaggggggg tacgtcacaa gaaggcgttc ccgtacaggg    300
gggtacgtaa catgttcagg ggggtacgtc acaaccaatc aggagctgcc acgttgcgaa    360
agtgacgttt cgaaaatggg cggcgcaaga ctccctatat attgcgcgca cataccggtc    420
ggcagtaggt atacgcaagg cggtccgggt ggatgcacgg aaacggcgga caaccggccg    480
ctgggggcag tgaatcggcg cttagccgag aggggcaacc tgggcccagc ggagccgcgc    540
aggggcaagt aatttcaaat gaacgctcac caagaagata ctccaccagg accatcaacg    600
gtgttcaggc caccaacaag ttcacggccg ttggaaaccc ctcactgcag agagatccgg    660
attggtatcg ctggaattac agtcactcta tcgctgtgtg gctgcgcgaa tgctcgcgtt    720
cccacgctaa gatctgcaac tgcggacaat tcagaaaaca ctggtttcaa gaatgtgccg    780
gacttgagga ccgatcaacc caagcctccc tcgaagaagc gatcctgcga cccctccgag    840
taccgggtaa gcgagctaaa agaaagcttg attaccacta ctcccagccg accccgaacc    900
gcaagaaggt gtataagact gtaagatggc aagacgagct cgcagaccga gaggccgatt    960
ttacgccttc agaagaggac ggtggcacca cctcaagcga cttcgacgaa gatataaatt   1020
tcgacatcgg aggagacagc ggtatcgtag acgagctttt aggaaggcct ttcacaaccc   1080
ccgccccggt acgtatagtg tgaggctgcc aaaccccccag tccacgatga ctatccgctt   1140
ccaaggagtc atctttctca ccgaaggact cattctacct aaaaacagca cagctggggg   1200
ctatgcggac cacatgtacg gggcgagagt cgccaagatc tcagtgaacc tgaaagagtt   1260
cctcctagca tcaatgaacc tgacatacgt gagcaagata ggaggcccca tcgccggtga   1320
gttgattgcg gacgggtcta aatcgcaagc cgcggagaac tggccaaatt gctggctgcc   1380
gctagataat aacgtgccct ccgctacacc atctgcatgg tggagatggg ctttaatgat   1440
gatgcagcca acggactcct gccggttttt taatcaccct aagcaaatga ccctgcaaga   1500
catgggtcgg atgtttgggg gctggcatct gttccgacac attgaaaccc gctttcagct   1560
ccttgccact aagaatgagg gatccttcag ccccgtggcg agtcttctct cccagggaga   1620
gtacctcacg cgccgcgacg atgttaagta cagcagcgac caccagaacc ggtggcgaaa   1680
aggcgagcaa ccgatgacgg gggggattgc ttacgcgacc ggtaaaatga gactcgacga   1740
gcaacaatac cctgctatgc ccccggaccc cccgatcatc accactacca ctgcgcaagg   1800
cacgcaagtc cgctgcatga atagcacgca agcttggtgg tcgtgggaca catatatgag   1860
ctttgcaaca ctcacagcac tcggtgctca atggtctttt cctccagggc aacgttcagt   1920
ttctagacgg tccttcaacc atcacaaggc ccgaggagcc ggggacccca agggccagag   1980
gtggcacacg ctggtgccgc tcggcacaga gaccataacc gacagctaca tgagagcacc   2040
ggcatcagag ctggacacga atttcttcac gctttacgta gcgcaaggca ctaataaatc   2100
gcagcaatac aagttcggca cagcaacata cgcgctaaag gaacccgtaa tgaagagcga   2160
ttcatgggca gtggtgcgcg tccagtccgt ctggcaactg ggtaacaggc aaaggccata   2220
cccgtgggac gttaactggg ccaacagcac catgtactgg gggtcgcagc cctgaaaagg   2280
gggggg                                                              2286
```

<210> SEQ ID NO 16
<211> LENGTH: 216
<212> TYPE: PRT
<213> ORGANISM: Artificial Sequence
<220> FEATURE:
<223> OTHER INFORMATION: mut Q 131 P of VP2 of Chicken anaemia virus

<400> SEQUENCE: 16

```
Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Pro Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215
```

<210> SEQ ID NO 17
<211> LENGTH: 2286
<212> TYPE: DNA
<213> ORGANISM: Artificial Sequence
<220> FEATURE:
<223> OTHER INFORMATION: mut R/K/K 150/151/152 G/A/A of Chicken anaemia
      virus genome

<400> SEQUENCE: 17

```
cccccttga accccccct ggggggatt cccccccaga cccccccttt ataaagcact      60

caataaacgc agctaattcg ttcaccgcac aatcgctttc cgagtggtta ctattccatc    120

accattctag cctgtacaca aaaagtaaag atggacgaat cgctcgactt cgctcgcgat    180

tcgtcgaagg cgggggccg gaggcccccc ggtggccccc tccaaggagt ggagcgtgta     240

caggggggta cgtcatccgt acaggggggg tacgtcacaa gaaggcgttc ccgtacaggg    300

gggtacgtaa catgttcagg ggggtacgtc acaaccaatc aggagctgcc acgttgcgaa    360

agtgacgttt cgaaaatggg cggcgcaaga ctccctatat attgcgcgca cataccggtc    420

ggcagtaggt atacgcaagg cggtccgggt ggatgcacgg aaacggcgga caaccggccg    480
```

-continued

```
ctgggggcag tgaatcggcg cttagccgag aggggcaacc tgggcccagc ggagccgcgc    540

aggggcaagt aatttcaaat gaacgctcac caagaagata ctccaccagg accatcaacg    600

gtgttcaggc caccaacaag ttcacggccg ttggaaaccc ctcactgcag agagatccgg    660

attggtatcg ctggaattac agtcactcta tcgctgtgtg gctgcgcgaa tgctcgcgtt    720

cccacgctaa gatctgcaac tgcggacaat tcagaaaaca ctggtttcaa gaatgtgccg    780

gacttgagga ccgatcaacc caagcctccc tcgaagaagc gatcctgcga cccctccgag    840

tacagggtaa gcgagctaaa agaaagcttg attaccacta ctcccagccg accccgaacg    900

gcgcggcggt gtataagact gtaagatggc aagacgagct cgcagaccga gaggccgatt    960

ttacgccttc agaagaggac ggtggcacca cctcaagcga cttcgacgaa gatataaatt   1020

tcgacatcgg aggagacagc ggtatcgtag acgagctttt aggaaggcct ttcacaaccc   1080

ccgccccggt acgtatagtg tgaggctgcc aaaccccccag tccacgatga ctatccgctt  1140

ccaaggagtc atctttctca ccgaaggact cattctacct aaaaacagca cagctggggg   1200

ctatgcggac cacatgtacg gggcgagagt cgccaagatc tcagtgaacc tgaaagagtt   1260

cctcctagca tcaatgaacc tgacatacgt gagcaagata ggaggcccca tcgccggtga   1320

gttgattgcg gacgggtcta aatcgcaagc cgcggagaac tggccaaatt gctggctgcc   1380

gctagataat aacgtgccct ccgctacacc atctgcatgg tggagatggg ctttaatgat   1440

gatgcagcca acggactcct gccggttttt taatcaccct aagcaaatga ccctgcaaga   1500

catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc ccccggaccc cccgatcatc accactacca ctgcgcaagg   1800

cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggacccca agggccagag   1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                              2286
```

<210> SEQ ID NO 18
<211> LENGTH: 216
<212> TYPE: PRT
<213> ORGANISM: Artificial Sequence
<220> FEATURE:
<223> OTHER INFORMATION: mut R/K/K of VP2 of Chicken anaemia virus

<400> SEQUENCE: 18

```
Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30
```

-continued

```
Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Gly Ala Ala Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215
```

<210> SEQ ID NO 19
<211> LENGTH: 2286
<212> TYPE: DNA
<213> ORGANISM: Artificial Sequence
<220> FEATURE:
<223> OTHER INFORMATION: mut D/E 161/162 G/G of Chicken anaemia virus genome

<400> SEQUENCE: 19

```
ccccccttga acccccccct ggggggggatt cccccccaga cccccccttt ataaagcact      60

caataaacgc agctaattcg ttcaccgcac aatcgctttc cgagtggtta ctattccatc     120

accattctag cctgtacaca aaaagtaaag atggacgaat cgctcgactt cgctcgcgat     180

tcgtcgaagg cggggggccg gaggcccccc ggtggccccc tccaaggagt ggagcgtgta     240

caggggggta cgtcatccgt acaggggggg tacgtcacaa gaaggcgttc ccgtacaggg     300

gggtacgtaa catgttcagg ggggtacgtc acaaccaatc aggagctgcc acgttgcgaa     360

agtgacgttt cgaaaatggg cggcgcaaga ctccctatat attgcgcgca cataccggtc     420

ggcagtaggt atacgcaagg cggtccgggt ggatgcacgg aaacggcgga caaccggccg     480

ctgggggcag tgaatcggcg cttagccgag aggggcaacc tgggcccagc ggagccgcgc     540

aggggcaagt aatttcaaat gaacgctcac caagaagata ctccaccagg accatcaacg     600

gtgttcaggc caccaacaag ttcacggccg ttggaaaccc ctcactgcag agagatccgg     660

attggtatcg ctggaattac agtcactcta tcgctgtgtg gctgcgcgaa tgctcgcgtt     720

cccacgctaa gatctgcaac tgcggacaat tcagaaaaca ctggtttcaa gaatgtgccg     780

gacttgagga ccgatcaacc caagcctccc tcgaagaagc gatcctgcga cccctccgag     840

tacagggtaa gcgagctaaa agaaagcttg attaccacta ctcccagccg accccgaacc     900

gcaagaaggt gtataagact gtaagatggc aaggcgggct cgcagaccga gaggccgatt     960
```

-continued

```
ttacgccttc agaagaggac ggtggcacca cctcaagcga cttcgacgaa gatataaatt   1020

tcgacatcgg aggagacagc ggtatcgtag acgagctttt aggaaggcct ttcacaaccc   1080

ccgccccggt acgtatagtg tgaggctgcc aaaccccccag tccacgatga ctatccgctt   1140

ccaaggagtc atctttctca ccgaaggact cattctacct aaaaacagca cagctggggg   1200

ctatgcggac cacatgtacg gggcgagagt cgccaagatc tcagtgaacc tgaaagagtt   1260

cctcctagca tcaatgaacc tgacatacgt gagcaagata ggaggcccca tcgccggtga   1320

gttgattgcg gacgggtcta aatcgcaagc cgcggagaac tggccaaatt gctggctgcc   1380

gctagataat aacgtgccct ccgctacacc atctgcatgg tggagatggg ctttaatgat   1440

gatgcagcca acggactcct gccggttttt taatcaccct aagcaaatga ccctgcaaga   1500

catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc cccggaccc cccgatcatc accactacca ctgcgcaagg   1800

cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggacccca agggccagag   1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                               2286
```

```
<210> SEQ ID NO 20
<211> LENGTH: 216
<212> TYPE: PRT
<213> ORGANISM: Artificial Sequence
<220> FEATURE:
<223> OTHER INFORMATION: mut D/E 161/162 G/G of VP2 of Chicken anaemia
      virus

<400> SEQUENCE: 20

Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
```

-continued

```
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Gly Gly Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215
```

<210> SEQ ID NO 21
<211> LENGTH: 2286
<212> TYPE: DNA
<213> ORGANISM: Artificial Sequence
<220> FEATURE:
<223> OTHER INFORMATION: mut L 163 P of Chicken anaemia virus genome

<400> SEQUENCE: 21

```
cccccttga acccccccct ggggggggatt cccccccaga cccccccttt ataaagcact     60
caataaacgc agctaattcg ttcaccgcac aatcgctttc cgagtggtta ctattccatc    120
accattctag cctgtacaca aaaagtaaag atggacgaat cgctcgactt cgctcgcgat    180
tcgtcgaagg cggggggccg gaggcccccc ggtggccccc tccaaggagt ggagcgtgta    240
caggggggta cgtcatccgt acaggggggg tacgtcacaa gaaggcgttc ccgtacaggg    300
gggtacgtaa catgttcagg ggggtacgtc acaaccaatc aggagctgcc acgttgcgaa    360
agtgacgttt cgaaaatggg cggcgcaaga ctccctatat attgcgcgca cataccggtc    420
ggcagtaggt atacgcaagg cggtccgggt ggatgcacgg aaacggcgga caaccggccg    480
ctgggggcag tgaatcggcg cttagccgag aggggcaacc tgggcccagc ggagccgcgc    540
aggggcaagt aatttcaaat gaacgctcac caagaagata ctccaccagg accatcaacg    600
gtgttcaggc caccaacaag ttcacggccg ttggaaaccc ctcactgcag agagatccgg    660
attggtatcg ctggaattac agtcactcta tcgctgtgtg gctgcgcgaa tgctcgcgtt    720
cccacgctaa gatctgcaac tgcggacaat tcagaaaaca ctggtttcaa gaatgtgccg    780
gacttgagga ccgatcaacc caagcctccc tcgaagaagc gatcctgcga cccctccgag    840
tacagggtaa gcgagctaaa agaaagcttg attaccacta ctcccagccg accccgaacc    900
gcaagaaggt gtataagact gtaagatggc aagacgagcc cgcagaccga gaggccgatt    960
ttacgccttc agaagaggac ggtggcacca cctcaagcga cttcgacgaa gatataaatt   1020
tcgacatcgg aggagacagc ggtatcgtag acgagctttt aggaaggcct ttcacaaccc   1080
ccgccccggt acgtatagtg tgaggctgcc aaacccccag tccacgatga ctatccgctt   1140
ccaaggagtc atctttctca ccgaaggact cattctacct aaaaacagca cagctggggg   1200
ctatgcggac cacatgtacg gggcgagagt cgccaagatc tcagtgaacc tgaaagagtt   1260
cctcctagca tcaatgaacc tgacatacgt gagcaagata ggaggcccca tcgccggtga   1320
gttgattgcg gacgggtcta aatcgcaagc cgcggagaac tggccaaatt gctggctgcc   1380
gctagataat aacgtgccct ccgctacacc atctgcatgg tggagatggg ctttaatgat   1440
gatgcagcca acggactcct gccggttttt taatcaccct aagcaaatga ccctgcaaga   1500
```

-continued

```
catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc ccccggaccc cccgatcatc accactacca ctgcgcaagg   1800

cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggacccca agggccagag   1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                              2286
```

<210> SEQ ID NO 22
<211> LENGTH: 216
<212> TYPE: PRT
<213> ORGANISM: Artificial Sequence
<220> FEATURE:
<223> OTHER INFORMATION: mut L 163 P of VP2 of Chicken anaemia virus

<400> SEQUENCE: 22

```
Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Pro Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
```

210 215

<210> SEQ ID NO 23
<211> LENGTH: 2286
<212> TYPE: DNA
<213> ORGANISM: Artificial Sequence
<220> FEATURE:
<223> OTHER INFORMATION: mut D 169 G of Chicken anaemia virus genome

<400> SEQUENCE: 23

```
cccccttga acccccccct ggggggggatt cccccccaga cccccccttt ataaagcact     60
caataaacgc agctaattcg ttcaccgcac aatcgctttc cgagtggtta ctattccatc    120
accattctag cctgtacaca aaaagtaaag atggacgaat cgctcgactt cgctcgcgat    180
tcgtcgaagg cggggggccg gaggcccccc ggtggccccc tccaaggagt ggagcgtgta    240
caggggggta cgtcatccgt acaggggggg tacgtcacaa gaaggcgttc ccgtacaggg    300
gggtacgtaa catgttcagg ggggtacgtc acaaccaatc aggagctgcc acgttgcgaa    360
agtgacgttt cgaaaatggg cggcgcaaga ctccctatat attgcgcgca cataccggtc    420
ggcagtaggt atacgcaagg cggtccgggt ggatgcacgg aaacggcgga caaccggccg    480
ctgggggcag tgaatcggcg cttagccgag aggggcaacc tgggcccagc ggagccgcgc    540
aggggcaagt aatttcaaat gaacgctcac caagaagata ctccaccagg accatcaacg    600
gtgttcaggc caccaacaag ttcacggccg ttggaaaccc ctcactgcag agagatccgg    660
attggtatcg ctggaattac agtcactcta tcgctgtgtg gctgcgcgaa tgctcgcgtt    720
cccacgctaa gatctgcaac tgcggacaat tcagaaaaca ctggtttcaa gaatgtgccg    780
gacttgagga ccgatcaacc caagcctccc tcgaagaagc gatcctgcga cccctccgag    840
tacagggtaa gcgagctaaa agaaagcttg attaccacta ctcccagccg accccgaacc    900
gcaagaaggt gtataagact gtaagatggc aagacgagct cgcagaccga gaggccggtt    960
ttacgccttc agaagaggac ggtggcacca cctcaagcga cttcgacgaa gatataaatt   1020
tcgacatcgg aggagacagc ggtatcgtag acgagctttt aggaaggcct ttcacaaccc   1080
ccgccccggt acgtatagtg tgaggctgcc aaaccccccag tccacgatga ctatccgctt   1140
ccaaggagtc atctttctca ccgaaggact cattctacct aaaaacagca cagctggggg   1200
ctatgcggac cacatgtacg gggcgagagt cgccaagatc tcagtgaacc tgaaagagtt   1260
cctcctagca tcaatgaacc tgacatacgt gagcaagata ggaggcccca tcgccggtga   1320
gttgattgcg gacgggtcta aatcgcaagc cgcggagaac tggccaaatt gctggctgcc   1380
gctagataat aacgtgccct ccgctacacc atctgcatgg tggagatggg ctttaatgat   1440
gatgcagcca acggactcct gccggttttt taatcaccct aagcaaatga ccctgcaaga   1500
catgggtcgg atgtttgggg gctggcatct gttccgacac attgaaaccc gctttcagct   1560
ccttgccact aagaatgagg gatccttcag ccccgtggcg agtcttctct cccagggaga   1620
gtacctcacg cgccgcgacg atgttaagta cagcagcgac caccagaacc ggtggcgaaa   1680
aggcgagcaa ccgatgacgg gggggattgc ttacgcgacc ggtaaaatga gactcgacga   1740
gcaacaatac cctgctatgc ccccggaccc ccccgatcatc accactacca ctgcgcaagg   1800
cacgcaagtc cgctgcatga atagcacgca agcttggtgg tcgtgggaca catatatgag   1860
ctttgcaaca ctcacagcac tcggtgctca atggtctttt cctccagggc aacgttcagt   1920
ttctagacgg tccttcaacc atcacaaggc ccgaggagcc ggggacccca agggccagag   1980
gtggcacacg ctggtgccgc tcggcacaga gaccataacc gacagctaca tgagagcacc   2040
```

-continued

```
ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                              2286


<210> SEQ ID NO 24
<211> LENGTH: 216
<212> TYPE: PRT
<213> ORGANISM: Artificial Sequence
<220> FEATURE:
<223> OTHER INFORMATION: mut D 169 G of VP2 of Chicken anaemia virus

<400> SEQUENCE: 24

Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Gly Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215


<210> SEQ ID NO 25
<211> LENGTH: 2286
<212> TYPE: DNA
<213> ORGANISM: Artificial Sequence
<220> FEATURE:
<223> OTHER INFORMATION: mut K 102 E of Chicken anaemia virus genome

<400> SEQUENCE: 25

cccccttga accccccct gggggggatt cccccccaga cccccccttt ataaagcact     60

caataaacgc agctaattcg ttcaccgcac aatcgctttc cgagtggtta ctattccatc    120

accattctag cctgtacaca aaaagtaaag atggacgaat cgctcgactt cgctcgcgat    180
```

-continued

```
tcgtcgaagg cggggggccg gaggcccccc ggtggccccc tccaaggagt ggagcgtgta    240

caggggggta cgtcatccgt acaggggggg tacgtcacaa gaaggcgttc ccgtacaggg    300

gggtacgtaa catgttcagg ggggtacgtc acaaccaatc aggagctgcc acgttgcgaa    360

agtgacgttt cgaaaatggg cggcgcaaga ctccctatat attgcgcgca cataccggtc    420

ggcagtaggt atacgcaagg cggtccgggt ggatgcacgg aaacggcgga caaccggccg    480

ctgggggcag tgaatcggcg cttagccgag aggggcaacc tgggcccagc ggagccgcgc    540

aggggcaagt aatttcaaat gaacgctcac caagaagata ctccaccagg accatcaacg    600

gtgttcaggc caccaacaag ttcacggccg ttggaaaccc ctcactgcag agagatccgg    660

attggtatcg ctggaattac agtcactcta tcgctgtgtg gctgcgcgaa tgctcgcgtt    720

cccacgctaa gatctgcaac tgcggacaat tcagagaaca ctggtttcaa gaatgtgccg    780

gacttgagga ccgatcaacc caagcctccc tcgaagaagc gatcctgcga cccctccgag    840

tacagggtaa gcgagctaaa agaaagcttg attaccacta ctcccagccg accccgaacc    900

gcaagaaggt gtataagact gtaagatggc aagacgagct cgcagaccga gaggccgatt    960

ttacgccttc agaagaggac ggtggcacca cctcaagcga cttcgacgaa gatataaatt   1020

tcgacatcgg aggagacagc ggtatcgtag acgagctttt aggaaggcct ttcacaaccc   1080

ccgccccggt acgtatagtg tgaggctgcc aaacccccag tccacgatga ctatccgctt   1140

ccaaggagtc atctttctca ccgaaggact cattctacct aaaaacagca cagctggggg   1200

ctatgcggac cacatgtacg gggcgagagt cgccaagatc tcagtgaacc tgaaagagtt   1260

cctcctagca tcaatgaacc tgacatacgt gagcaagata ggaggcccca tcgccggtga   1320

gttgattgcg gacgggtcta aatcgcaagc cgcggagaac tggccaaatt gctggctgcc   1380

gctagataat aacgtgccct ccgctacacc atctgcatgg tggagatggg ctttaatgat   1440

gatgcagcca acggactcct gccggttttt taatcaccct aagcaaatga ccctgcaaga   1500

catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc ccccggaccc cccgatcatc accactacca ctgcgcaagg   1800

cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggacccca agggccagag   1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                              2286
```

<210> SEQ ID NO 26
<211> LENGTH: 216
<212> TYPE: PRT
<213> ORGANISM: Artificial Sequence
<220> FEATURE:
<223> OTHER INFORMATION: mut K 102 E of VP2 of Chicken anaemia virus -continued

<400> SEQUENCE: 26

```
Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80

Ala Val Trp Leu Arg Glu Cys Ser Arg Ser His Ala Lys Ile Cys Asn
                85                  90                  95

Cys Gly Gln Phe Arg Glu His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215
```

<210> SEQ ID NO 27
<211> LENGTH: 2286
<212> TYPE: DNA
<213> ORGANISM: Artificial Sequence
<220> FEATURE:
<223> OTHER INFORMATION: mut E 186 G of Chicken anaemia virus genome

<400> SEQUENCE: 27

```
cccccttga acccccccct ggggggggatt cccccccaga cccccccttt ataaagcact     60

caataaacgc agctaattcg ttcaccgcac aatcgctttc cgagtggtta ctattccatc    120

accattctag cctgtacaca aaaagtaaag atggacgaat cgctcgactt cgctcgcgat    180

tcgtcgaagg cggggggccg gaggcccccc ggtggccccc tccaaggagt ggagcgtgta    240

caggggggta cgtcatccgt acaggggggg tacgtcacaa gaaggcgttc ccgtacaggg    300

gggtacgtaa catgttcagg ggggtacgtc acaaccaatc aggagctgcc acgttgcgaa    360

agtgacgttt cgaaaatggg cggcgcaaga ctccctatat attgcgcgca cataccggtc    420

ggcagtaggt atacgcaagg cggtccgggt ggatgcacgg aaacggcgga caaccggccg    480

ctgggggcag tgaatcggcg cttagccgag aggggcaacc tgggcccagc ggagccgcgc    540

aggggcaagt aatttcaaat gaacgctcac caagaagata ctccaccagg accatcaacg    600

gtgttcaggc caccaacaag ttcacggccg ttggaaaccc ctcactgcag agagatccgg    660

attggtatcg ctggaattac agtcactcta tcgctgtgtg gctgcgcgaa tgctcgcgtt    720
```

-continued

```
cccacgctaa gatctgcaac tgcggacaat tcagaaaaca ctggtttcaa gaatgtgccg    780

gacttgagga ccgatcaacc caagcctccc tcgaagaagc gatcctgcga cccctccgag    840

tacagggtaa gcgagctaaa agaaagcttg attaccacta ctcccagccg accccgaacc    900

gcaagaaggt gtataagact gtaagatggc aagacgagct cgcagaccga gaggccgatt    960

ttacgccttc agaagaggac ggtggcacca cctcaagcga cttcgacgga gatataaatt   1020

tcgacatcgg aggagacagc ggtatcgtag acgagctttt aggaaggcct ttcacaaccc   1080

ccgccccggt acgtatagtg tgaggctgcc aaaccccag tccacgatga ctatccgctt   1140

ccaaggagtc atctttctca ccgaaggact cattctacct aaaaacagca cagctggggg   1200

ctatgcggac cacatgtacg gggcgagagt cgccaagatc tcagtgaacc tgaaagagtt   1260

cctcctagca tcaatgaacc tgacatacgt gagcaagata ggaggcccca tcgccggtga   1320

gttgattgcg gacgggtcta aatcgcaagc cgcggagaac tggccaaatt gctggctgcc   1380

gctagataat aacgtgccct ccgctacacc atctgcatgg tggagatggg ctttaatgat   1440

gatgcagcca acggactcct gccggttttt taatcaccct aagcaaatga ccctgcaaga   1500

catgggtcgg atgtttgggg gctggcatct gttccgacac attgaaaccc gctttcagct   1560

ccttgccact aagaatgagg gatccttcag ccccgtggcg agtcttctct cccagggaga   1620

gtacctcacg cgccgcgacg atgttaagta cagcagcgac caccagaacc ggtggcgaaa   1680

aggcgagcaa ccgatgacgg gggggattgc ttacgcgacc ggtaaaatga gactcgacga   1740

gcaacaatac cctgctatgc ccccggaccc cccgatcatc accactacca ctgcgcaagg   1800

cacgcaagtc cgctgcatga atagcacgca agcttggtgg tcgtgggaca catatatgag   1860

ctttgcaaca ctcacagcac tcggtgctca atggtctttt cctccagggc aacgttcagt   1920

ttctagacgg tccttcaacc atcacaaggc ccgaggagcc ggggacccca agggccagag   1980

gtggcacacg ctggtgccgc tcggcacaga gaccataacc gacagctaca tgagagcacc   2040

ggcatcagag ctggacacga atttcttcac gctttacgta gcgcaaggca ctaataaatc   2100

gcagcaatac aagttcggca cagcaacata cgcgctaaag gaacccgtaa tgaagagcga   2160

ttcatgggca gtggtgcgcg tccagtccgt ctggcaactg ggtaacaggc aaaggccata   2220

cccgtgggac gttaactggg ccaacagcac catgtactgg gggtcgcagc cctgaaaagg   2280

gggggg                                                               2286
```

<210> SEQ ID NO 28
<211> LENGTH: 216
<212> TYPE: PRT
<213> ORGANISM: Artificial Sequence
<220> FEATURE:
<223> OTHER INFORMATION: mut E 186 G of VP2 of Chicken anaemia virus

<400> SEQUENCE: 28

```
Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Ser His Ser Ile
65                  70                  75                  80
```

-continued

```
Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Gly Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215
```

<210> SEQ ID NO 29
<211> LENGTH: 30
<212> TYPE: DNA
<213> ORGANISM: Artificial Sequence
<220> FEATURE:
<223> OTHER INFORMATION: mut C 86 R +oligo

<400> SEQUENCE: 29
ctgcgcgaac gctcgcgttc ccacgctaag 30

<210> SEQ ID NO 30
<211> LENGTH: 30
<212> TYPE: DNA
<213> ORGANISM: Artificial Sequence
<220> FEATURE:
<223> OTHER INFORMATION: mut C 86 R -oligo

<400> SEQUENCE: 30
aacgcgagcg ttcgcgcagc cacacagcga 30

<210> SEQ ID NO 31
<211> LENGTH: 20
<212> TYPE: DNA
<213> ORGANISM: Artificial Sequence
<220> FEATURE:
<223> OTHER INFORMATION: mut C95 S +oligo

<400> SEQUENCE: 31
cgctaagatc agcaactgcg 20

<210> SEQ ID NO 32
<211> LENGTH: 22
<212> TYPE: DNA
<213> ORGANISM: Artificial Sequence
<220> FEATURE:
<223> OTHER INFORMATION: mut C 95 S -oligo

<400> SEQUENCE: 32
cgcagttgct gatcttagcg tg 22

<210> SEQ ID NO 33
<211> LENGTH: 21
<212> TYPE: DNA

-continued

<213> ORGANISM: Artificial Sequence
<220> FEATURE:
<223> OTHER INFORMATION: mut C 97 S +oligo

<400> SEQUENCE: 33
atctgcaaca gcggacaatt c 21

<210> SEQ ID NO 34
<211> LENGTH: 24
<212> TYPE: DNA
<213> ORGANISM: Artificial Sequence
<220> FEATURE:
<223> OTHER INFORMATION: mut C 97 S -oligo

<400> SEQUENCE: 34
attgtccgct gttgcagatc ttag 24

<210> SEQ ID NO 35
<211> LENGTH: 25
<212> TYPE: DNA
<213> ORGANISM: Artificial Sequence
<220> FEATURE:
<223> OTHER INFORMATION: mut R 101 G +oligo

<400> SEQUENCE: 35
ctgcggacaa ttcggaaaac actgg 25

<210> SEQ ID NO 36
<211> LENGTH: 24
<212> TYPE: DNA
<213> ORGANISM: Artificial Sequence
<220> FEATURE:
<223> OTHER INFORMATION: mut R 101 G -oligo

<400> SEQUENCE: 36
cagtgttttc cgaattgtcc gcag 24

<210> SEQ ID NO 37
<211> LENGTH: 32
<212> TYPE: DNA
<213> ORGANISM: Artificial Sequence
<220> FEATURE:
<223> OTHER INFORMATION: mut H 103 Y +oligo

<400> SEQUENCE: 37
cagaaaatac tggtttcaag aatgtgccgg ac 32

<210> SEQ ID NO 38
<211> LENGTH: 29
<212> TYPE: DNA
<213> ORGANISM: Artificial Sequence
<220> FEATURE:
<223> OTHER INFORMATION: mut H 103 Y -oligo

<400> SEQUENCE: 38
gaaaccagta ttttctgaat tgtccgcag 29

<210> SEQ ID NO 39
<211> LENGTH: 23
<212> TYPE: DNA
<213> ORGANISM: Artificial Sequence
<220> FEATURE:
<223> OTHER INFORMATION: mut R 129 G +oligo

<400> SEQUENCE: 39
ctgcgacccc tcggagtaca ggg 23

-continued

<210> SEQ ID NO 40
<211> LENGTH: 29
<212> TYPE: DNA
<213> ORGANISM: Artificial Sequence
<220> FEATURE:
<223> OTHER INFORMATION: mut R 129 G -oligo

<400> SEQUENCE: 40
ccctgtactc cgaggggtcg caggatcgc 29

<210> SEQ ID NO 41
<211> LENGTH: 26
<212> TYPE: DNA
<213> ORGANISM: Artificial Sequence
<220> FEATURE:
<223> OTHER INFORMATION: mut Q 131 P +oligo

<400> SEQUENCE: 41
cgagtaccgg gtaagcgagc taaaag 26

<210> SEQ ID NO 42
<211> LENGTH: 21
<212> TYPE: DNA
<213> ORGANISM: Artificial Sequence
<220> FEATURE:
<223> OTHER INFORMATION: mut Q 131 P -oligo

<400> SEQUENCE: 42
cgcttacccg gtactcggag g 21

<210> SEQ ID NO 43
<211> LENGTH: 24
<212> TYPE: DNA
<213> ORGANISM: Artificial Sequence
<220> FEATURE:
<223> OTHER INFORMATION: mut R/K/K 150/151/152 G/A/A +oligo

<400> SEQUENCE: 43
ccgaacggcg cggcggtgta taag 24

<210> SEQ ID NO 44
<211> LENGTH: 25
<212> TYPE: DNA
<213> ORGANISM: Artificial Sequence
<220> FEATURE:
<223> OTHER INFORMATION: mut R/K/K 150/151/152 G/A/A -oligo

<400> SEQUENCE: 44
atacaccgcc gcgccgttcg ggtc 25

<210> SEQ ID NO 45
<211> LENGTH: 27
<212> TYPE: DNA
<213> ORGANISM: Artificial Sequence
<220> FEATURE:
<223> OTHER INFORMATION: mut D/E 161/162 G/G +oligo

<400> SEQUENCE: 45
taagatggca aggcgggctc gcagacc 27

<210> SEQ ID NO 46
<211> LENGTH: 20
<212> TYPE: DNA
<213> ORGANISM: Artificial Sequence
<220> FEATURE:

-continued

<223> OTHER INFORMATION: mut D/E 161/162 G/G

<400> SEQUENCE: 46
tgcgagcccg ccttgccatc 20

<210> SEQ ID NO 47
<211> LENGTH: 21
<212> TYPE: DNA
<213> ORGANISM: Artificial Sequence
<220> FEATURE:
<223> OTHER INFORMATION: mut L 163 P +oligo

<400> SEQUENCE: 47
gacgagcccg cagaccgaga g 21

<210> SEQ ID NO 48
<211> LENGTH: 24
<212> TYPE: DNA
<213> ORGANISM: Artificial Sequence
<220> FEATURE:
<223> OTHER INFORMATION: mut L 163 P -oligo

<400> SEQUENCE: 48
ggcctctcgg tctgcgggct cgtc 24

<210> SEQ ID NO 49
<211> LENGTH: 24
<212> TYPE: DNA
<213> ORGANISM: Artificial Sequence
<220> FEATURE:
<223> OTHER INFORMATION: mut D 169 G +oligo

<400> SEQUENCE: 49
gagaggccgg ttttacgcct tcag 24

<210> SEQ ID NO 50
<211> LENGTH: 22
<212> TYPE: DNA
<213> ORGANISM: Artificial Sequence
<220> FEATURE:
<223> OTHER INFORMATION: mut D 169 G -oligo

<400> SEQUENCE: 50
gcgtaaaacc ggcctctcgg tc 22

<210> SEQ ID NO 51
<211> LENGTH: 29
<212> TYPE: DNA
<213> ORGANISM: Artificial Sequence
<220> FEATURE:
<223> OTHER INFORMATION: mut K 102 E +oligo

<400> SEQUENCE: 51
ctgcggacaa ttcagagaac actggtttc 29

<210> SEQ ID NO 52
<211> LENGTH: 29
<212> TYPE: DNA
<213> ORGANISM: Artificial Sequence
<220> FEATURE:
<223> OTHER INFORMATION: mut K 102 E -oligo

<400> SEQUENCE: 52
gaaaccagtg ttctctgaat tgtccgcag 29

-continued

<210> SEQ ID NO 53
<211> LENGTH: 26
<212> TYPE: DNA
<213> ORGANISM: Artificial Sequence
<220> FEATURE:
<223> OTHER INFORMATION: mut E 186 G +oligo

<400> SEQUENCE: 53
gcgacttcga cggagatata aatttc 26

<210> SEQ ID NO 54
<211> LENGTH: 22
<212> TYPE: DNA
<213> ORGANISM: Artificial Sequence
<220> FEATURE:
<223> OTHER INFORMATION: mut E 186 G -oligo

<400> SEQUENCE: 54
tttatatctc cgtcgaagtc gc 22

<210> SEQ ID NO 55
<211> LENGTH: 25
<212> TYPE: DNA
<213> ORGANISM: Artificial Sequence
<220> FEATURE:
<223> OTHER INFORMATION: CAV.1 primer

<400> SEQUENCE: 55
ctatcgaatt ccgagtggtt actat 25

<210> SEQ ID NO 56
<211> LENGTH: 20
<212> TYPE: DNA
<213> ORGANISM: Artificial Sequence
<220> FEATURE:
<223> OTHER INFORMATION: CAV.10 primer

<400> SEQUENCE: 56
tgctcacgta tgtcaggttc 20

<210> SEQ ID NO 57
<211> LENGTH: 20
<212> TYPE: DNA
<213> ORGANISM: Artificial Sequence
<220> FEATURE:
<223> OTHER INFORMATION: CAV.2 primer

<400> SEQUENCE: 57
gcggagccgc gcaggggcaa 20

<210> SEQ ID NO 58
<211> LENGTH: 26
<212> TYPE: DNA
<213> ORGANISM: Artificial Sequence
<220> FEATURE:
<223> OTHER INFORMATION: CAV 19 oligo

<400> SEQUENCE: 58
cggtccggga ggatgcacgg aaacgg 26

<210> SEQ ID NO 59
<211> LENGTH: 25
<212> TYPE: DNA
<213> ORGANISM: Artificial Sequence
<220> FEATURE:
<223> OTHER INFORMATION: CAV 20 oligo -continued

<400> SEQUENCE: 59
gtgcatcctc ccgaccgcct tgcgt 25

<210> SEQ ID NO 60
<211> LENGTH: 26
<212> TYPE: DNA
<213> ORGANISM: Artificial Sequence
<220> FEATURE:
<223> OTHER INFORMATION: CAV 21 oligo

<400> SEQUENCE: 60
cggtccgggt ggatggacgg aaacgg 26

<210> SEQ ID NO 61
<211> LENGTH: 26
<212> TYPE: DNA
<213> ORGANISM: Artificial Sequence
<220> FEATURE:
<223> OTHER INFORMATION: CAV 22 oligo

<400> SEQUENCE: 61
gtccatccac ccggaccgcc ttgcgt 26

<210> SEQ ID NO 62
<211> LENGTH: 25
<212> TYPE: DNA
<213> ORGANISM: Artificial Sequence
<220> FEATURE:
<223> OTHER INFORMATION: CAV 1 oligo

<400> SEQUENCE: 62
ctatcgaatt ccgagtggtt actat 25

<210> SEQ ID NO 63
<211> LENGTH: 30
<212> TYPE: DNA
<213> ORGANISM: Artificial Sequence
<220> FEATURE:
<223> OTHER INFORMATION: CAV 11 oligo

<400> SEQUENCE: 63
agctcgtctt gccatcttac agtcttatac 30

<210> SEQ ID NO 64
<211> LENGTH: 9
<212> TYPE: PRT
<213> ORGANISM: Artificial Sequence
<220> FEATURE:
<223> OTHER INFORMATION: Chicken anaemia virus- signature motif CAV VP2
PTP

<400> SEQUENCE: 64

Ile Cys Asn Cys Gly Gln Phe Arg Lys
1 5

<210> SEQ ID NO 65
<211> LENGTH: 34
<212> TYPE: DNA
<213> ORGANISM: Artificial Sequence
<220> FEATURE:
<223> OTHER INFORMATION: CAV.1 primer

<400> SEQUENCE: 65
cggtccggat ccatgcacgg aaacggcgga caac 34

-continued

<210> SEQ ID NO 66
<211> LENGTH: 33
<212> TYPE: DNA
<213> ORGANISM: Artificial Sequence
<220> FEATURE:
<223> OTHER INFORMATION: CAV.2 primer

<400> SEQUENCE: 66
ggtttggaat tctcacacta tacgtaccgg ggc 33

<210> SEQ ID NO 67
<211> LENGTH: 31
<212> TYPE: DNA
<213> ORGANISM: Artificial Sequence
<220> FEATURE:
<223> OTHER INFORMATION: TLMV.1 primer

<400> SEQUENCE: 67
ttggatccat gagcagcttt ctaacaccat c 31

<210> SEQ ID NO 68
<211> LENGTH: 33
<212> TYPE: DNA
<213> ORGANISM: Artificial Sequence
<220> FEATURE:
<223> OTHER INFORMATION: TLMV.2 primer

<400> SEQUENCE: 68
ggcgaattct tacccatcgt cttcttcgaa atc 33

<210> SEQ ID NO 69
<211> LENGTH: 10
<212> TYPE: PRT
<213> ORGANISM: Artificial sequence
<220> FEATURE:
<223> OTHER INFORMATION: consensus signature motif
<220> FEATURE:
<221> NAME/KEY: MOD_RES
<222> LOCATION: (1)
<223> OTHER INFORMATION: Ile or Val
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (10)
<223> OTHER INFORMATION: Ser or Thr

<400> SEQUENCE: 69

```
Xaa His Cys Xaa Ala Gly Xaa Gly Arg Xaa
1               5                   10
```

<210> SEQ ID NO 70
<211> LENGTH: 21
<212> TYPE: PRT
<213> ORGANISM: Artificial sequence
<220> FEATURE:
<223> OTHER INFORMATION: consensus signature motif
<220> FEATURE:
<221> NAME/KEY: MOD_RES
<222> LOCATION: (2)..(8)
<223> OTHER INFORMATION: Variable amino acid
<220> FEATURE:
<221> NAME/KEY: MOD_RES
<222> LOCATION: (10)..(12)
<223> OTHER INFORMATION: Variable amino acid -continued

```
<220> FEATURE:
<221> NAME/KEY: MOD_RES
<222> LOCATION: (14)
<223> OTHER INFORMATION: Variable amino acid
<220> FEATURE:
<221> NAME/KEY: MOD_RES
<222> LOCATION: (16)..(20)
<223> OTHER INFORMATION: Variable amino acid

<400> SEQUENCE: 70

Trp Xaa Xaa Xaa Xaa Xaa Xaa Xaa His Xaa Xaa Xaa Cys Xaa Cys Xaa
1               5                   10                  15

Xaa Xaa Xaa Xaa His
            20


<210> SEQ ID NO 71
<211> LENGTH: 9
<212> TYPE: PRT
<213> ORGANISM: Artificial sequence
<220> FEATURE:
<223> OTHER INFORMATION: synthetic peptide

<400> SEQUENCE: 71

Glu Asn Asp Tyr Ile Asn Ala Ser Leu
1               5
```

The invention claimed is:

1. A method for imparting or conferring immunity to circovirus infection in an animal comprising administering to the animal an effective amount of a circovirus vaccine, wherein the vaccine comprises an isolated nucleic acid molecule derived or obtained from a circovirus genome, the nucleic acid molecule including at least a portion of a coding region for viral protein 2 (VP2) of at least 20 nucleotides in length having a mutation therein, wherein the mutation is present in a nucleic acid region encoding amino acid residue 87, 95, 97, 101, 102, 103, 129, 131, 150, 151, 152, or 161 to 170 as set out in SEQ ID NO: 2; or the vaccine comprises an isolated attenuated circovirus capable of cellular replication and having a mutation in viral nucleic acid encoding viral protein 2 (VP2), wherein the mutation is present in a nucleic acid region encoding amino acid residue 87, 95, 97, 101, 102, 103, 129, 131, 150, 151, 152, or 161 to 170 as set out in SEQ ID NO: 2.

2. The method according to claim 1 wherein the animal is a bird.

3. The method according to claim 2 wherein the bird is a chicken.

4. The method according to claim 1 wherein the vaccine is administered parenterally, intramuscularly, subcutaneously, orally, intranasally, or in ovo route.

5. The method according to claim 4 wherein the animal is a bird and the route of administration of the vaccine is by mucosal administration, aerosol administration or via drinking water.

6. The method according to claim 5 wherein the bird is a chicken.

7. The method according to claim 1 wherein the vaccine is administered in a dosage range from 1 to 100 million $TCID_{50}$.

8. The method according to claim 7 wherein the vaccine is administered in a dosage range of about 1000 $TCID_{50}$.

9. A method of producing a circovirus vaccine comprising:

(a) inoculating an isolated nucleic acid molecule derived or obtained from a circovirus genome into the yolk sac of an embryonated egg, wherein the nucleic acid molecule includes at least a portion of a coding region for viral protein 2 (VP2) of at least 20 nucleotides in length having a mutation therein, wherein the mutation is present in a nucleic acid region encoding amino acid residue 87, 95, 97, 101. 102, 103, 129, 131, 150, 151, 152, or 161 to 170 as set out in SEQ ID NO: 2;

(b) allowing circovirus to replicate from the isolated nucleic acid; and (c) harvesting the circovirus from the egg.

10. The method according to claim 9, wherein the isolated nucleic acid molecule being derived or obtained from Chicken anaemia virus (CAV), a TT virus (TTV) or other similar virus expressing a VP2 protein.

11. The method according to claim 10, wherein the isolated nucleic acid molecule being derived or obtained from Chicken anaemia virus (CAV).

12. The method according to claim 9, wherein the mutation is present in a region of nucleic acid encoding the signature motif of VP2.

13. The method according to claim 12, wherein the mutation alters viral PTPase activity, PTPase motifs, acidic alpha helical regions or basic beta sheet regions.

14. The method according to claim 9, wherein the sites targeted for mutagenesis within CAV VP2 are selected from the group consisting of 86, 95, 97, 101, 103 and 169.

15. The method according to claim 9, wherein the mutations are selected from the group consisting of mut C86 R, mut C 95 S, mut C 97 S, mut R 101 G, mut K 102 E, mut H 103 Y, mut R 129 G, mut Q 131 P, mut R/K/K 150/151/152 G/A/A, mut D/E 161/162 G/G, mut L 163 P, mut D 169 G, mut E 186 G, and combinations thereof.

16. The method according to claim 15 wherein the mutation comprises mut D 169 G.

17. The method according to claim 9 wherein the circovirus has a nucleic acid sequence selected from the group consisting of sequence no.'s 3, 5, 7, 9, 11, 13, 15, 17, 19, 21, 23, 25, and 27.

18. An isolated attenuated circovirus capable of cellular replication and having a mutation in viral nucleic acid encoding viral protein 2 (VP2), wherein the mutation is present in a nucleic acid region encoding amino acid residue 87, 95, 97, 101, 102, 103, 129, 131, 150, 151, 152, or 161 to 170 as set out in SEQ ID NO: 2.

19. The isolated attenuated circovirus according to claim 18 wherein the circovirus being derived or obtained from Chicken anaemia virus (CAV), a TT virus (TTV) or other similar virus expressing a VP2 protein.

20. The isolated attenuated circovirus according to claim 19, wherein the circovirus is derived or obtained from Chicken anaemia virus (CAV).

21. The isolated attenuated circovirus according to claim 20 wherein the mutation is present in a region of nucleic acid encoding the signature motif of VP2.

22. The isolated attenuated circovirus according to claim 21 wherein the mutation alters viral PTPase activity, PTPase motifs, acidic alpha helical regions or basic beta sheet regions.

23. The isolated attenuated circovirus according to claim 22, wherein the sites targeted for mutagenesis within CAV VP2 are nucleic acid regions encoding amino acid residues selected from the group consisting of 87, 95, 97, 101, 103 and 169.

24. The isolated attenuated circovirus according to claim 23 wherein the mutations are selected from the group consisting of mut C87 R, mut C 95 S, mut C 97 S, mut R 101 G, mut K 102 E, mut H 103 Y, mut R 129 G, mut Q 131 P, mut R/K/K 150/151/152 G/A/A, mut D/E 161/162 G/G, mut L 163 P, mut D 169 G, and combinations thereof.

25. The isolated attenuated circovirus according to claim 24 comprising mut D 169 G.

26. The isolated attenuated circovirus according to claim 25 having a nucleic acid sequence selected from the group consisting of SEQ ID NOS: 3, 5, 7, 9, 11, 13, 15, 17, 19, 21, 23, and 25.

27. A circovirus vaccine composition comprising an attenuated circovirus according to claim 26 together with a suitable carrier or diluent.

28. An isolated nucleic acid molecule derived or obtained from a circovirus genome, the nucleic acid molecule including at least a portion of a coding region for viral protein 2 (VP2) of at least 20 nucleotides in length having a mutation therein, wherein the mutation is present in a nucleic acid region encoding amino acid residue 87, 95, 97, 101, 102, 103, 129, 131, 150, 151, 152, or 161 to 170 as set out in SEQ ID NO:2.

29. The isolated nucleic acid molecule according to claim 28, wherein the circovirus being derived or obtained from Chicken anaemia virus (CAV), a TT virus (TTV) or other similar virus expressing a VP2 protein.

30. The isolated nucleic acid molecule according to claim 29, wherein the circovirus being derived or obtained from Chicken anaemia virus (CAV).

31. The isolated nucleic acid molecule according to claim 30 wherein the mutation is present in a region of nucleic acid encoding the signature motif of VP2.

32. The isolated nucleic acid molecule according to claim 31, wherein the mutation alters viral PTPase activity, PTPase motifs, acidic alpha helical regions or basic beta sheet regions.

33. The isolated nucleic acid molecule according to claim 32, wherein the sites targeted for mutagenesis within CAV VP2 are nucleic acid regions encoding amino acid residues selected from the group consisting of 87, 95, 97, 101,103 and 169.

34. The isolated nucleic acid molecule according to claim 33, wherein the mutations are selected from the group consisting of mut C 87 R, mut C 95 S, mut C 97 S, mut R 101 G, mut K 102 E, mut H 103 Y, mut R 129 G, mut Q 131 P, mut R/K/K 150/151/152 G/A/A, mut D/E 161/162 G/G, mut L 163 P, mut D 169 G, and combinations thereof.

35. The isolated nucleic acid molecule according to claim 34 comprising mut D 169 G.

36. The isolated nucleic acid molecule according to claim 35 comprising a sequence selected from the group consisting of SEQ ID NOS: 1, 3, 5, 7, 9, 11, 13, 15, 17, 19,21,23,and 25.

37. A vaccine composition comprising an isolated nucleic acid molecule according to claim 28 together with an acceptable carrier or diluent.

* * * * *

UNITED STATES PATENT AND TRADEMARK OFFICE

CERTIFICATE OF CORRECTION

PATENT NO. : 7,442,378 B2
APPLICATION NO. : 10/480565
DATED : October 28, 2008
INVENTOR(S) : Glenn F. Browning et al.

It is certified that error appears in the above-identified patent and that said Letters Patent is hereby corrected as shown below:

The paragraph in column 5, line 4 should read as follows:

In one preferred form, a mutation is present in the region of nucleic acid encoding the key residues in the signature motif of VP2. Such mutations should modify the role of the PTPase during viral infection. More preferably, sites targeted for mutagenesis within CAV VP2 are 87, 95, 97, 101, 103, and 169. Residue 87 is normally C and was mutated to R (mut C 87 R), and the other demonstrative mutations were mut C 95 S, mut C 97 S, mut R 101 G and mut H 103 Y. The mutations mut C 95 S and mut C 97 S remove the cysteine residues predicted to be essential to PTPase activity and to be the catalytic cysteines involved in the formation of the cysteinyl-phosphate intermediate formed during catalysis. The mutation mut R 101 G removes the basic, charged residues predicted to be essential to PTPase activity and to be involved in the coordination of the phosphotyrosine substrate to the catalytic cysteine residues. Residues 103 and 87 flank the predicted signature motif and are highly conserved across TT and CAV viruses.

The paragraph in column 5, line 38 should read as follows:

Preferably, CAV constructs are selected from SEQ ID NO:s 1, 3, 5, 7, 9, 11, 13, 15, 17, 19, 21, 23, 25, or 27.

The paragraph in column 7, line 29 should read as follows:

Preferably, the isolated nucleic acid molecule is selected from SEQ ID NO:s 1, 3, 5, 7, 9, 11, 13, 15, 17, 39, 21, 23, 25, or 27.

The paragraph in column 7, line 57 should read as follows:

Preferably, the isolated VP2 molecule includes the amino acid sequences selected from SEQ ID NO:s 2, 4, 6, 8, 10, 12, 14, 16, 18, 20, 22, 24, 26, or 28.

Signed and Sealed this

Fourteenth Day of December, 2010

David J. Kappos
*Director of the United States Patent and Trademark Office*

Figure 2:
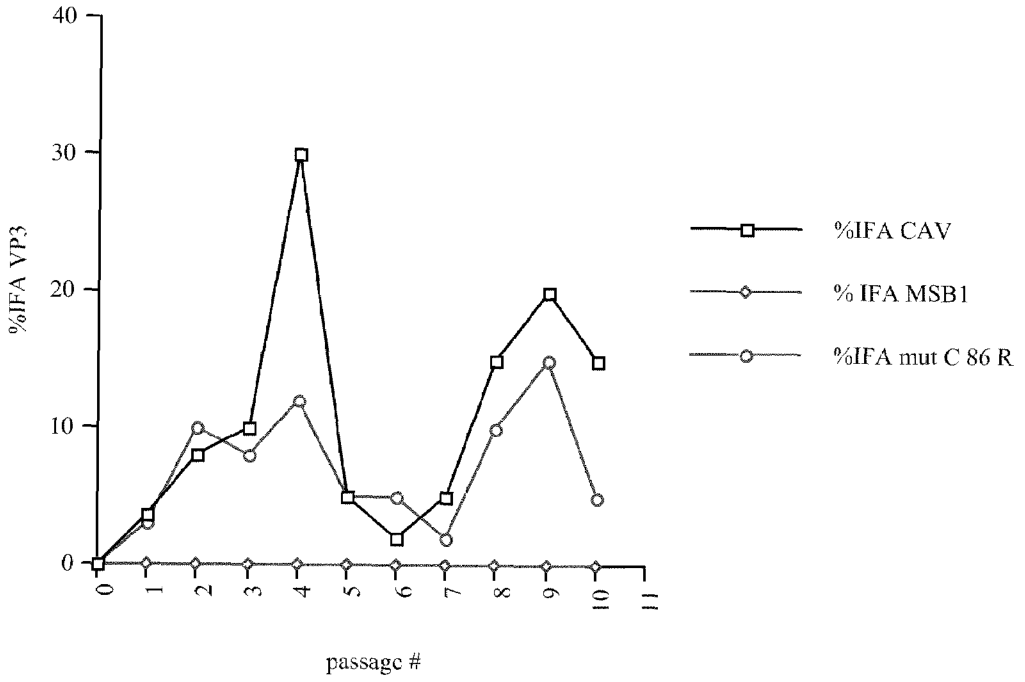
FIG. 2 shows transfection of mut C86 R into MSB1 cells.
Figure 3:
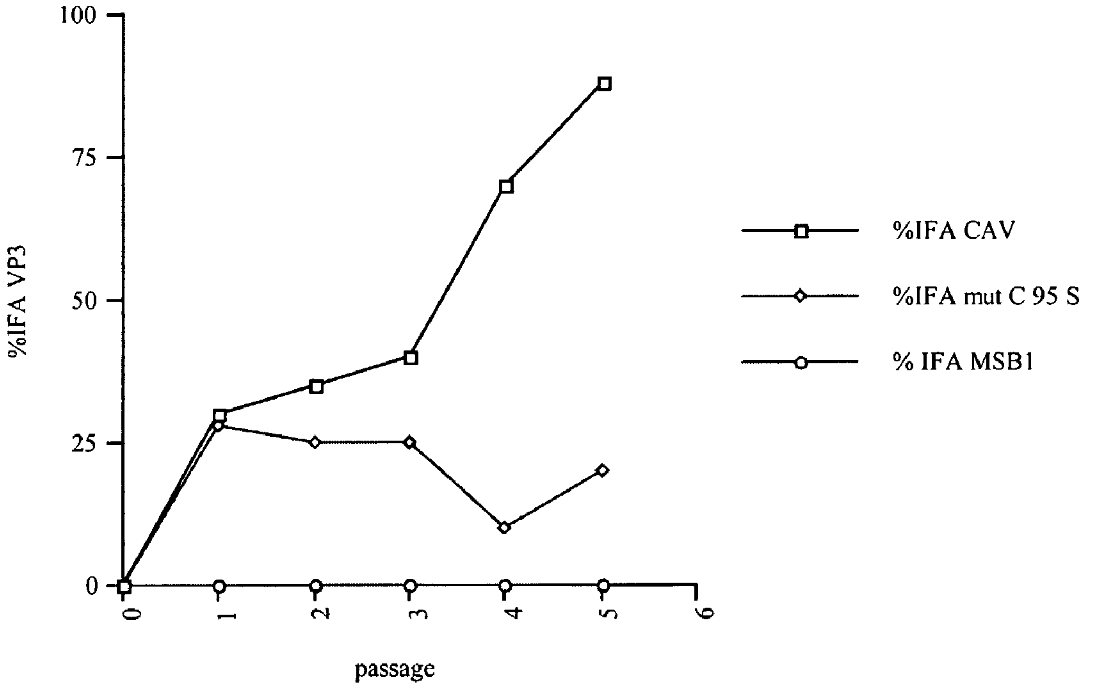
FIG. 3 shows transfection of mut C 95 S into MSB1 cells.
Figure 4:
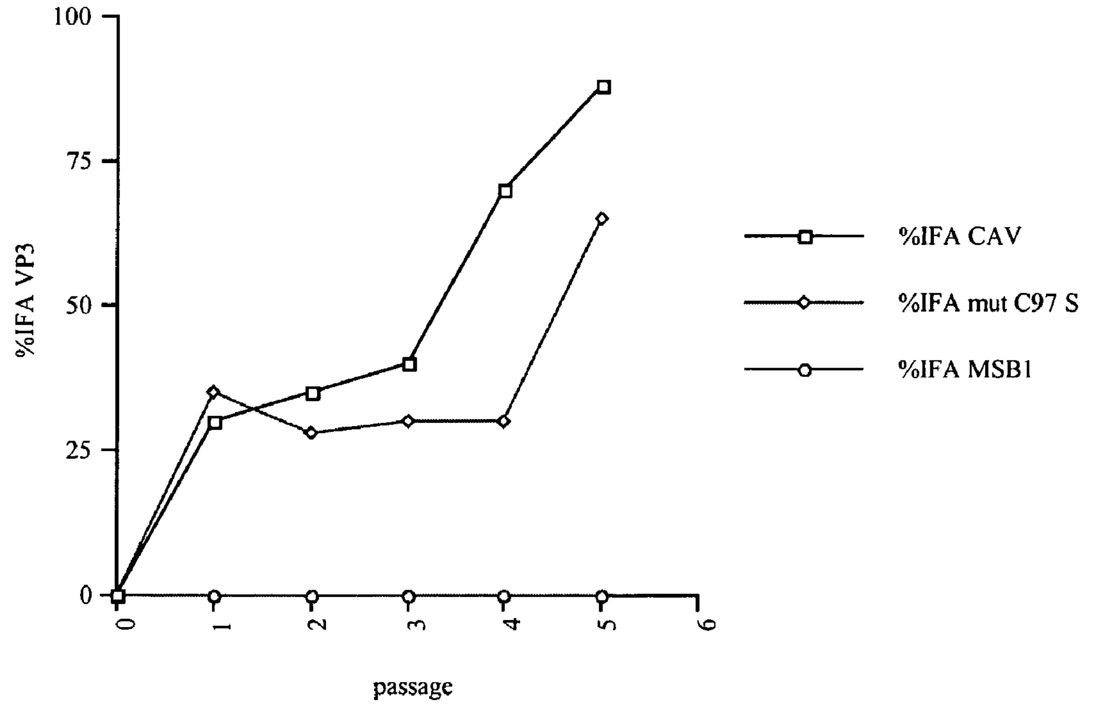
FIG. 4 shows transfection of mut C 97 S into MSB1 cells.
Figure 5:
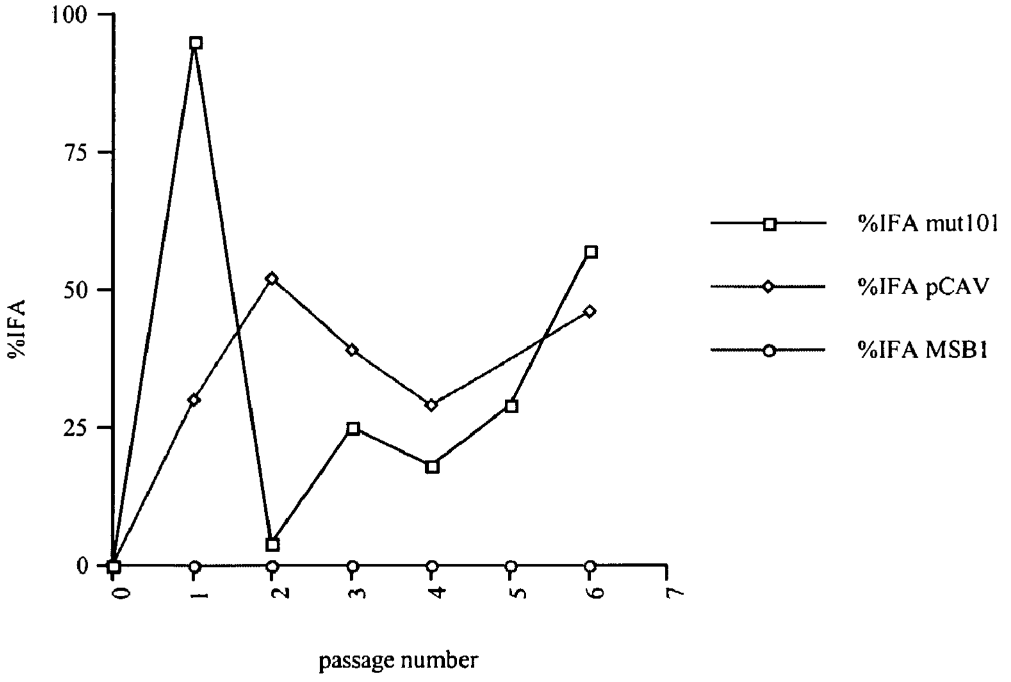
FIG. 5 shows transfection of mut R 101 G into MSB1 cells.
Figure 6:
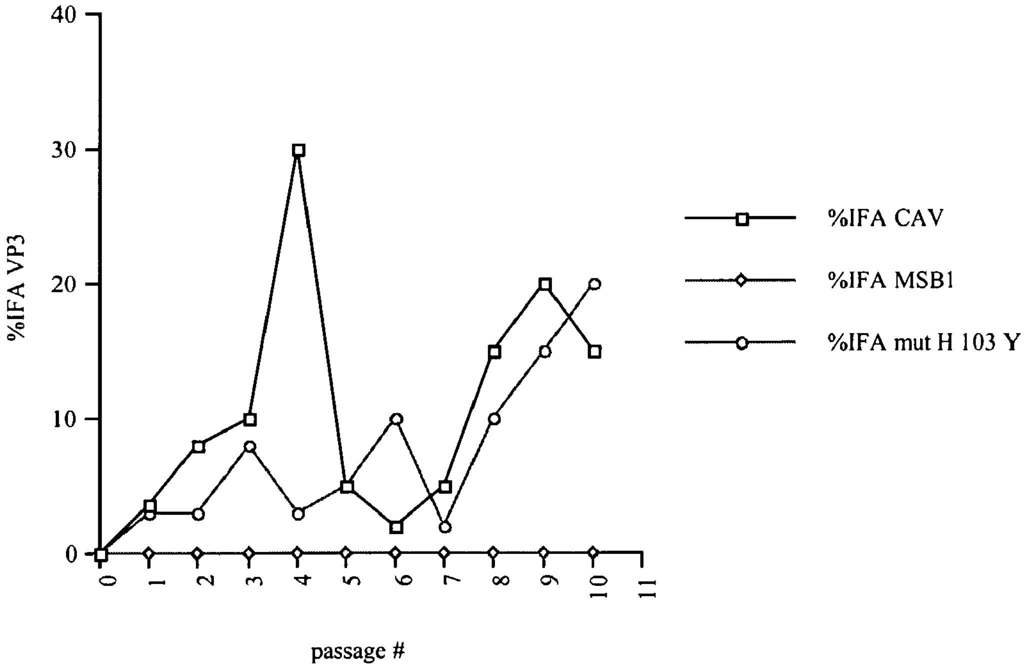
FIG. 6 shows transfection of mut H103 Y into MSB1 cells.
Figure 7:
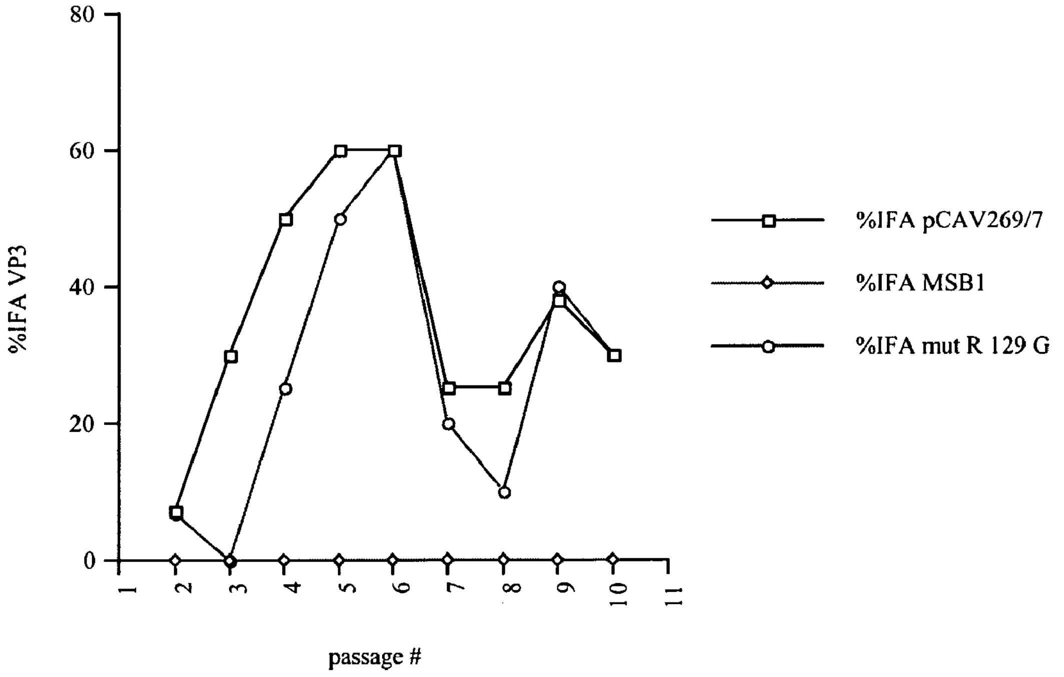
FIG. 7 shows transfection of mut R129 G into MSB1 cells.
Figure 8:
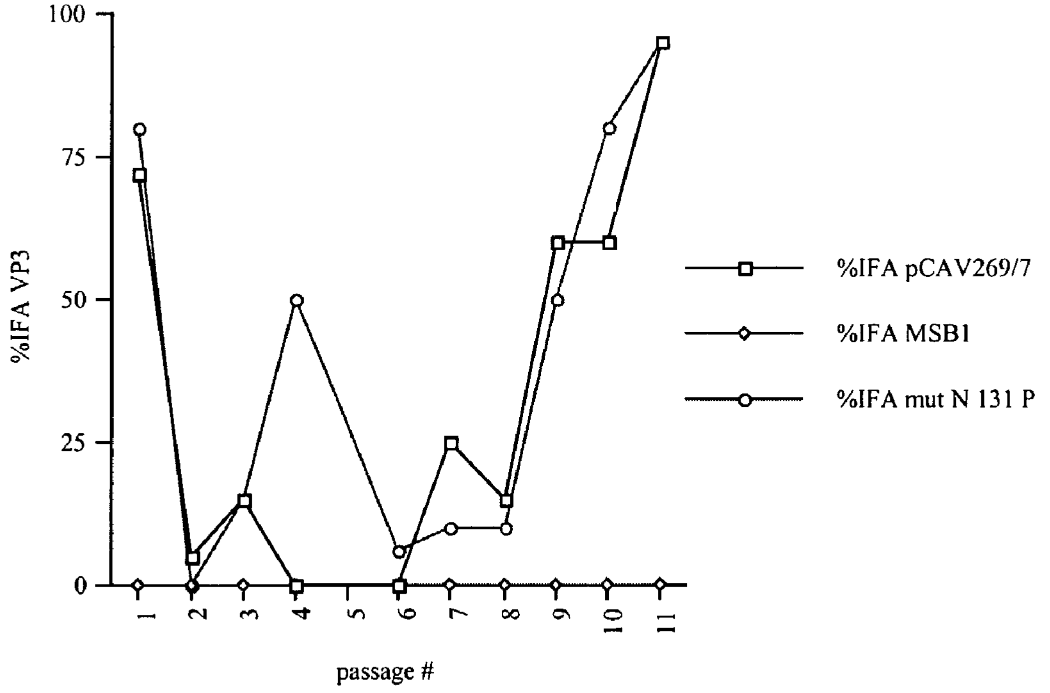
FIG. 8 shows transfection of mut Q 131 P into MSB1 cells.
Figure 9:
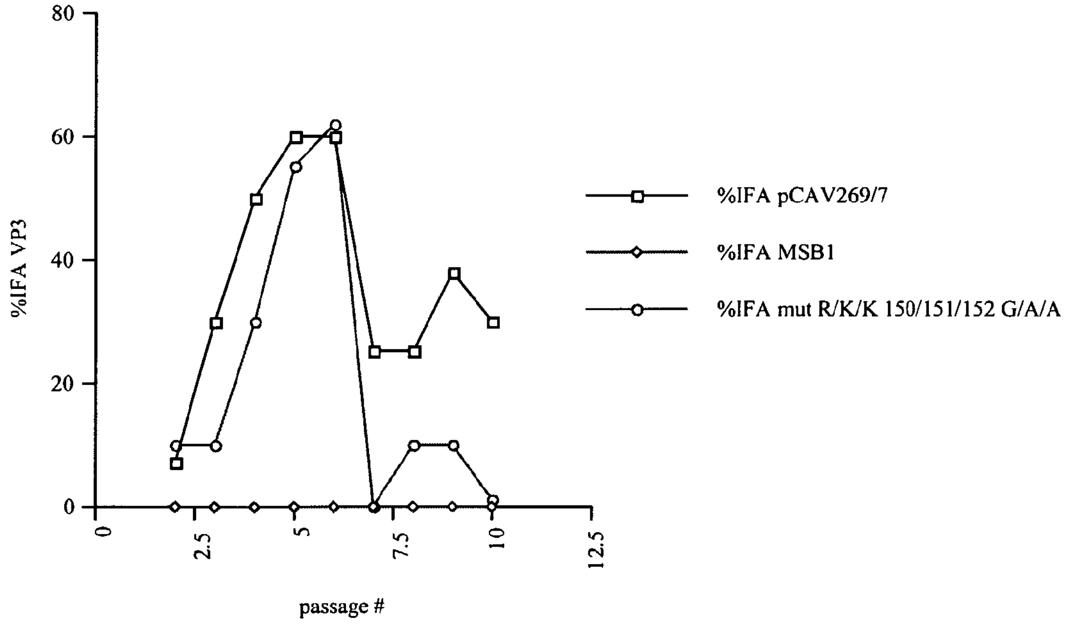
FIG. 9 shows transfection of mut R/K/K 150/151/152 G/A/A into MSB1 cells.
Figure 10:
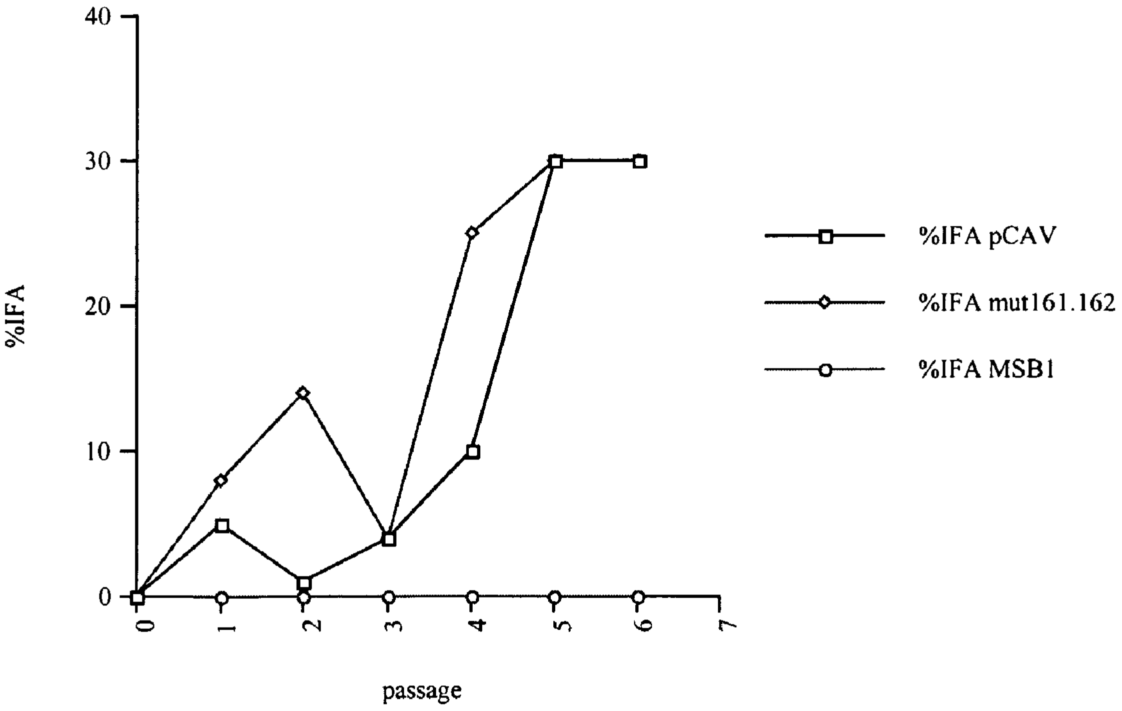
FIG. 10 shows transfection of mut D/E 161/162 G/G into MSB1 cells.
Figure 11:
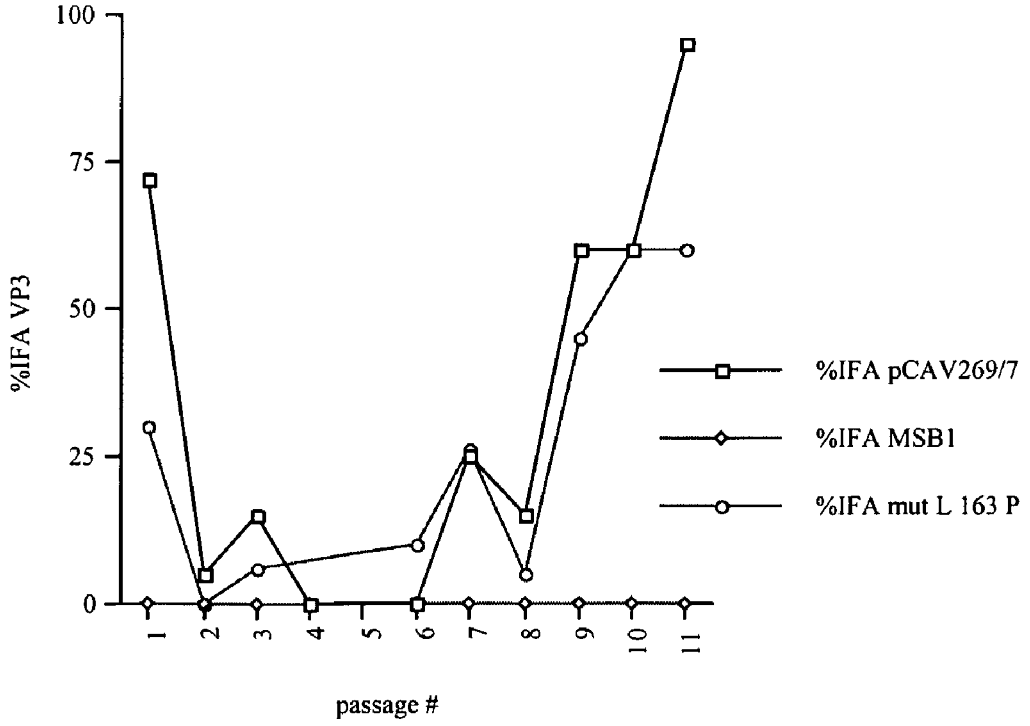
FIG. 11 shows transfection of mut L 163 P into MSB1 cells.
Figure 12:
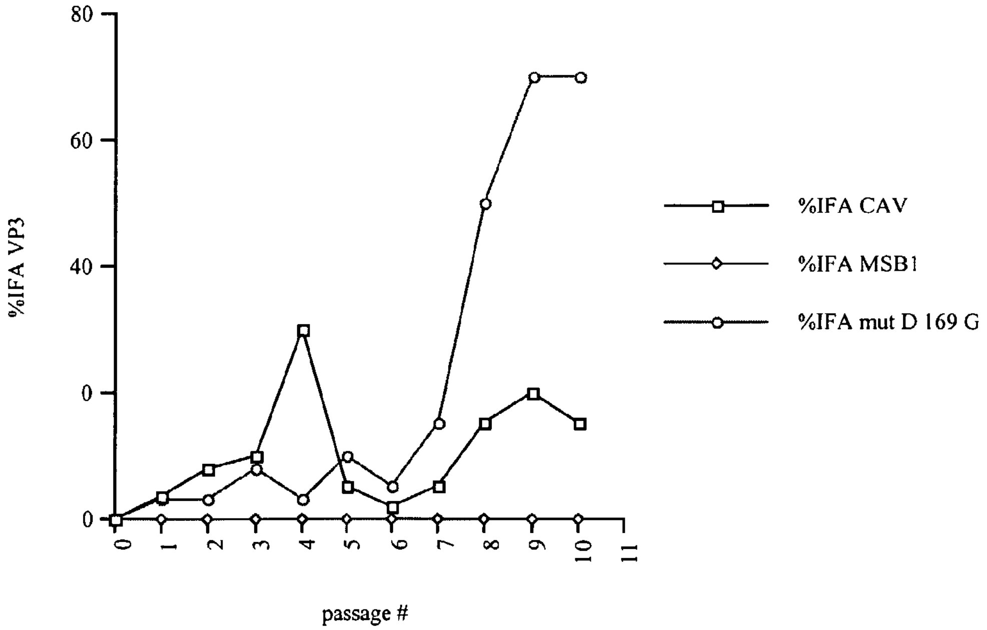
FIG. 12 shows transfection of mut DI 69 G into MSB1 cells.

The paragraph in column 8, line 51 should read as follows:

FIG. 2 shows transfection of mut C 87 R into MSB1 cells.

The paragraph in column 9, line 55 should read as follows:

Studies described later (EXPERIMENTAL PROCEDURES--VP2) have established PTPase activity and predicted key residues in the signature motif have been identified by comparison to known PTPase signature motifs. These residues have formed the basis for the design of a mutagenesis strategy in an infectious full genome clone of CAV. Mutations can be designed to modify the role of the PTPase during infection based on an understanding of their effect on PTPase catalysis in vitro. Sites targeted for mutagenesis within CAV VP2 to demonstrate the applicability of this strategy were ~~86~~ 87, 95, 97, 101, and 103. Residue ~~86~~ 87 is normally C and was mutated to ~~S~~ R (mut C ~~86 S~~ 87 R), and the other demonstrative mutations were mut C 95 S, mut C 97 S, mut R 101 G, and mut H 103 Y. The mutations mut C 95 S and mut C 97 S remove the cysteine residues predicted to be essential to PTPase activity and to be the catalytic cysteines involved in the formation of the cysteinyl-phosphate intermediate formed during catalysis. The mutations mut R 101 G removes the basic, charged residues predicted to be essential to PTPase activity and to be involved in the coordination of the phosphotyrosine substrate to the catalytic cysteine residues. Residues 103 and ~~86~~ 87 flank the predicted signature motif and are highly conserved across TT and CAV viruses.

The paragraph in column 10, line 10 should read as follows:

VP2 protein structural predictions were made using software available through the ANGIS interface (WebANGIS, Australian National Genomic Information Service). A region of high degree secondary structure was identified towards the carboxyl-terminal end of VP2. Chou-Fasman plots of the region predict an acidic region consisting of α-helix, followed by a basic region consisting of α-helix and β-sheet, then a second acidic region of α-helix. The secondary structure is further subdivided by a series of proline residues. There are two predicted regions of amphipathic α-helix from residues 128 to 143 and amphipathic β-sheet from residues 151 to 158 (FIG. 1). It is predicted that the high degree of secondary structure correlates to a functional protein domain. The predictions for secondary structure allow the introduction of mutations designed to disrupt the structural organization of the region thereby modifying the function of this region. To demonstrate the effect of mutation within the region of predicted basic amphipathic alpha-helix mut R 129 G and mut R/K/K 150/151/152 G/A/A have been constructed to neutralize the polar basic charge distribution in the secondary structure. The mut Q 131 P has also been introduced into the alpha helix in this region to break the helix. An identical approach was employed to disrupt the region of acidic alpha helix with the introduction of mut L 163 P. In the region of acidic alpha helix mut D/E 161/162 G/G and mut D 169 G constructs were made with the objective of neutralizing the acidic charge distribution. The mutated nucleic sequences of the CAV genome and VP2 amino acid sequences are listed in SEQ ID NO:s 1 to 28.

The table in column 10, line 10 should read as follows:

Table 1. Primers (SEQ ID NOS 29-54, left to right, in order of appearance) incorporating base changes encoding directed mutations within CAV VP2 sequence. The numbering of mutations is based on VP2 amino acid sequence. Mutated residues are indicated.

| mutation introduced into CAV VP2 | + sense oligonucleotide | - sense oligonucleotide |
|---|---|---|
| mut C 87 R | ctgcgcgaaCgctcgc gttcccacgctaag | aacgcgagcGttcgcg cagccacacagcga |
| mut C 95 S | cgctaagatcAgcaact gcg | cgcagttgcTgatctta gcgtg |
| mut C 97 S | atctgcaacAgcggac aattc | attgtccgcTgttgcag atcttag |
| mut R 101 G | ctgcggacaattcGga aaacactgg | cagtgttttcCgaatt gtccgcag |
| mut H 103 Y | cagaaaaTactggtttc aagaatgtgccggac | gaaaccagtAttttct gaattgtccgcag |
| mut R 129 G | ctgcgacccctcGgag tacaggg | ccctgtactcCgaggg gtcgcaggatcgc |
| mut Q131 P | cgagtacCgggtaagc gagctaaaag | cgcttacccGgtactc ggagg |
| mut R/K/K 150/151/152 G/A/A | ccgaacGgcGCgGCg gtgtataag | atacaccGCcGCgcCg ttcggggtc |
| mut D/E 161/162 G/G | taagatggcaagGcg Ggctcgcagacc | tgcgagcCcgCcttgc catc |
| mut L 163 P | gacgagcCcgcagacc gagag | ggcctctcggtctgcg Ggctcgtc |
| mut D 169 G | gagaggccgGttttac gccttcag | gcgtaaaaCcggcctc tcggtc |
| mut K 102 E | ctgcggacaattcagaGa acactggtttc | gaaaccagtgttCtct gaattgtccgcag |
| mut E 186 G | gcgacttcgacgGaga tataaatttc | tttatatctCcgtcgaag tcgc |

The description in column 12, lines 24-26, should be corrected to read as follows:

Methods for mutagenesis of all other mutants except for mut C 87 R and mut H 103 Y were as described for mut C 95 S and mut C 97 S.

The description in column 53, SEQ ID NO: 3 at numeric identifier <223> should read as follows:

<210> 3
<211> 2286
<212> DNA
<213> Artificial Sequence

<220>
<223> Description of Artificial Sequence: Synthetic
mut C 87 R of Chicken anaemia virus <400> 3
cccccttga acccccccct gggggggatt ccccccaga ccccccttt ataaagcact 60
caataaacgc agctaattcg ttcaccgcac aatcgctttc cgagtggtta ctattccatc 120
accattctag cctgtacaca aaaagtaaag atggacgaat cgctcgactt cgctcgcgat 180
tcgtcgaagg cgggggccg gaggcccccc ggtggccccc tccaaggagt ggagcgtgta 240
caggggggta cgtcatccgt acagggggg tacgtcacaa gaaggcgttc ccgtacaggg 300
gggtacgtaa catgttcagg ggggtacgtc acaaccaatc aggagctgcc acgttgcgaa 360
agtgacgttt cgaaaatggg cggcgcaaga ctccctatat attgcgcgca cataccggtc 420
ggcagtaggt atacgcaagg cggtccgggt ggatgcacgg aaacggcgga caaccggccg 480
ctgggggcag tgaatcggcg cttagccgag aggggcaacc tgggcccagc ggagccgcgc 540
aggggcaagt aatttcaaat gaacgctcac caagaagata ctccaccagg accatcaacg 600
gtgttcaggc caccaacaag ttcacggccg ttggaaaccc ctcactgcag agagatccgg 660
attggtatcg ctggaattac agtcactcta tcgctgtgtg gctgcgcgaa cgctcgcgtt 720
cccacgctaa gatctgcaac tgcggacaat tcagaaaaca ctggtttcaa gaatgtgccg 780
gacttgagga ccgatcaacc caagcctccc tcgaagaagc gatcctgcga cccctccgag 840
tacagggtaa gcgagctaaa agaaagcttg attaccacta ctcccagccg accccgaacc 900
gcaagaaggt gtataagact gtaagatggc aagacgagct cgcagaccga gaggccgatt 960
ttacgccttc agaagaggac ggtggcacca cctcaagcga cttcgacgaa gatataaatt 1020
tcgacatcgg aggagacagc ggtatcgtag acgagctttt aggaaggcct ttcacaaccc 1080
ccgcccccggt acgtatagtg tgaggctgcc aaacccccag tccacgatga ctatccgctt 1140
ccaaggagtc atctttctca ccgaaggact cattctacct aaaaacagca cagctggggg 1200
ctatgcggac cacatgtacg gggcgagagt cgccaagatc tcagtgaacc tgaaagagtt 1260
cctcctagca tcaatgaacc tgacatacgt gagcaagata ggaggcccca tcgccggtga 1320
gttgattgcg gacgggtcta aatcgcaagc cgcggagaac tggccaaatt gctggctgcc 1380
gctagataat aacgtgccct ccgctacacc atctgcatgg tggagatggg ctttaatgat 1440
gatgcagcca acggactcct gccggttttt taatcaccct aagcaaatga ccctgcaaga 1500
catgggtcgg atgtttgggg gctggcatct gttccgacac attgaaaccc gctttcagct 1560
ccttgccact aagaatgagg gatccttcag ccccgtggcg agtcttctct cccagggaga 1620
gtacctcacg cgccgcgacg atgttaagta cagcagcgac caccagaacc ggtggcgaaa 1680
aggcgagcaa ccgatgacgg gggggattgc ttacgcgacc ggtaaaatga gactcgacga 1740
gcaacaatac cctgctatgc cccccggaccc cccgatcatc accactacca ctgcgcaagg 1800
cacgcaagtc cgctgcatga atagcacgca agcttggtgg tcgtgggaca catatatgag 1860
ctttgcaaca ctcacagcac tcggtgctca atggtctttt cctccagggc aacgttcagt 1920
ttctagacgg tccttcaacc atcacaaggc ccgaggagcc ggggacccca agggccagag 1980
gtggcacacg ctggtgccgc tcggcacaga gaccataacc gacagctaca tgagagcacc 2040
ggcatcagag ctggacacga atttcttcac gctttacgta gcgcaaggca ctaataaatc 2100
gcagcaatac aagttcggca cagcaacata cgcgctaaag gaacccgtaa tgaagagcga 2160
ttcatgggca gtggtgcgcg tccagtccgt ctggcaactg ggtaacaggc aaaggccata 2220
cccgtgggac gttaactggg ccaacagcac catgtactgg gggtcgcagc cctgaaaagg 2280
gggggg 2286

The description in column 53, SEQ ID NO: 4 at numeric identifier <223> should read as follows:

<210> 4
<211> 216
<212> PRT
<213> Artificial Sequence

<220>
<223> Description of Artificial Sequence: Synthetic
mut C 87 R of Chicken anaemia virus

<400> 4

Met His Gly Asn Gly Gly Gln Pro Ala Ala Gly Gly Ser Glu Ser Ala
1 5 10 15

Leu Ser Arg Glu Gly Gln Pro Gly Pro Ser Gly Ala Ala Gln Gly Gln
20 25 30

Val Ile Ser Asn Glu Arg Ser Pro Arg Arg Tyr Ser Thr Arg Thr Ile
35 40 45

Asn Gly Val Gln Ala Thr Asn Lys Phe Thr Ala Val Gly Asn Pro Ser
50 55 60

Leu Gln Arg Asp Pro Asp Trp Tyr Arg Trp Asn Tyr Ser His Ser Ile
65 70 75 80

Ala Val Trp Leu Arg Glu Arg Ser Arg Ser His Ala Lys Ile Cys Asn
85 90 95

Cys Gly Gln Phe Arg Lys His Trp Phe Gln Glu Cys Ala Gly Leu Glu
100 105 110

Asp Arg Ser Thr Gln Ala Ser Leu Glu Glu Ala Ile Leu Arg Pro Leu
115 120 125

Arg Val Gln Gly Lys Arg Ala Lys Arg Lys Leu Asp Tyr His Tyr Ser
130 135 140

Gln Pro Thr Pro Asn Arg Lys Lys Val Tyr Lys Thr Val Arg Trp Gln
145 150 155 160

Asp Glu Leu Ala Asp Arg Glu Ala Asp Phe Thr Pro Ser Glu Glu Asp
165 170 175

Gly Gly Thr Thr Ser Ser Asp Phe Asp Glu Asp Ile Asn Phe Asp Ile
180 185 190

Gly Gly Asp Ser Gly Ile Val Asp Glu Leu Leu Gly Arg Pro Phe Thr
195 200 205

Thr Pro Ala Pro Val Arg Ile Val
210 215

In column 113, line 30; claim 1 should read as follows:

1. A method of inducing an immune response to circovirus infection in an animal comprising administering to the animal an effective amount of an isolated nucleic acid molecule derived or obtained from a circovirus genome, the nucleic acid molecule including at least a portion of a coding region for viral protein 2 (VP2) of at least 20 nucleotides in length having a mutation therein, wherein the mutation is present in a nucleic acid region encoding amino acid residue 87, 95, 97, 101, 102, 103, 129, 131, 150, 151, 152, or 161 to 170 as set out in SEQ ID NO: 2; or an isolated attenuated circovirus capable of cellular replication and having a mutation in viral nucleic acid encoding viral protein 2 (VP2), wherein the mutation is present in a nucleic acid region encoding amino acid residue 87, 95, 97, 101, 102, 103, 129, 131, 150, 151, 152, or 161 to 170 as set out in SEQ ID NO: 2.

In column 113, line 51; claim 4 should read as follows:

4. The method according to claim 1 wherein the isolated nucleic acid or isolated, attenuated circovirus is administered parenterally, intramuscularly, subcutaneously orally, intranasally, or *in ovo* route.

In column 113, line 55; claim 5 should read as follows:

5. The method according to claim 4 wherein the animal is a bird and the route of administration is by mucosal administration, aerosol administration or via drinking water.

In column 113, line 60; claim 7 should read as follows:

7. The method according to claim 1 wherein the isolated, attenuated circovirus is administered in a dosage range from 1 to 100 million $TCID_{50}$.

In column 113, line 62; claim 8 should read as follows:

8. The method according to claim 7 wherein the isolated, attenuated circovirus is administered in a dosage of about 1000 $TCID_{50}$.

In column 113, line 65; claim 9 should read as follows:

9. A method of producing an isolated, attenuated circovirus comprising:

(a) inoculating an isolated nucleic acid molecule derived or obtained from a circovirus genome into the yolk sac of an embryonated egg, wherein the nucleic acid molecule includes at least a portion of a coding region for viral protein 2 (VP2) of at least 20 nucleotides in length having a mutation therein, wherein the mutation is present in a nucleic acid region encoding amino acid residue 87, 95, 97, 101, 102, 103, 129, 131, 150, 151, 152, or 161 to 170 as set out in SEQ ID NO: 2;

(b) allowing circovirus to replicate from the isolated nucleic acid; and (c) harvesting the circovirus from the egg.

In column 114, line 54; claim 14 “86” should be replaced with --87--.

In column 114, line 57; claim 15 “C86” should be replaced with --C87--.

In column 114, line 66; claim 17 should be replaced with --SEQ ID NO:s--.

In column 115, line 28; claim 27, “vaccine” should be deleted.

In column 116, claim 35; line 36 should read as follows:

--of SEQ ID NOS: 3, 5, 7, 9, 11, 13, 15, 17, 19, 21, 23, and 25.--